United States Patent
Zhang et al.

(10) Patent No.: US 11,142,535 B2
(45) Date of Patent: Oct. 12, 2021

(54) HETEROCYCLIC COMPOUND AS SYK INHIBITOR AND/OR SYK-HDAC DUAL INHIBITOR

(71) Applicant: Hangzhou Innogate Pharma Co., Ltd., Zhejiang (CN)

(72) Inventors: Hancheng Zhang, Zhejiang (CN); Shifeng Liu, Zhejiang (CN); Xiangyang Ye, Zhejiang (CN); Wenting Chen, Zhejiang (CN)

(73) Assignee: Hangzhou Innogate Pharma Co., Ltd., Zhejiang (CN)

( * ) Notice: Subject to any disclaimer, the term of this patent is extended or adjusted under 35 U.S.C. 154(b) by 0 days.

(21) Appl. No.: 16/468,902

(22) PCT Filed: Dec. 12, 2017

(86) PCT No.: PCT/CN2017/115755
§ 371 (c)(1),
(2) Date: Jun. 12, 2019

(87) PCT Pub. No.: WO2018/108083
PCT Pub. Date: Jun. 21, 2018

(65) Prior Publication Data
US 2020/0079795 A1    Mar. 12, 2020

(30) Foreign Application Priority Data

Dec. 12, 2016 (CN) .......................... 201611141394.8

(51) Int. Cl.
*C07D 519/00* (2006.01)
*C07D 487/04* (2006.01)

(52) U.S. Cl.
CPC ......... *C07D 519/00* (2013.01); *C07D 487/04* (2013.01)

(58) Field of Classification Search
CPC .................................................. C07D 487/04
See application file for complete search history.

(56) References Cited

U.S. PATENT DOCUMENTS

2013/0338142 A1* 12/2013 Blomgren ............... A61P 35/00
514/211.05

FOREIGN PATENT DOCUMENTS

| WO | 2009102468 A1 | 8/2009 | |
| WO | WO2009/102468 | * 8/2009 | .......... C07D 487/04 |
| WO | 2016197987 A1 | 12/2016 | |
| WO | WO2016/197987 | * 12/2016 | .......... C07D 487/04 |
| WO | 201810883 A1 | 1/2018 | |

OTHER PUBLICATIONS

Wolff, M.E., "Burger's Medicinal Chemistry", pp. 975-977 (1996)
Bankeretal., "Modern Pharmaceuticals", p. 596 (1997).*
Pinedo et al. (2000).*
McMahon et al. (2000).*
Vippagunta et al. (2001).*
International Search Report dated Feb. 26, 2018 in International Patent Application No. PCT/CN2017/115755.

* cited by examiner

*Primary Examiner* — Paul V Ward
(74) *Attorney, Agent, or Firm* — Ice Miller LLP

(57) ABSTRACT

A heterocyclic compound as a Syk inhibitor and/or a Syk-HDAC dual inhibitor, or pharmaceutically acceptable salts, prodrugs, deuterated derivatives, hydrates, and solvates thereof are provided. Specifically, a compound of formula (I) is provided, which has dual inhibitory activity for Syk and/or Syk-HDAC.

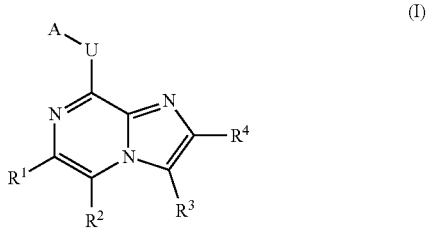

10 Claims, No Drawings

HETEROCYCLIC COMPOUND AS SYK INHIBITOR AND/OR SYK-HDAC DUAL INHIBITOR

CROSS-REFERENCE TO RELATED APPLICATION

This application is a Section 371 of International Application No. PCT/CN2017/115755, filed Dec. 12, 2017, which was published in the Chinese language on Jun. 21, 2018, under International Publication No. WO 2018/108083 A1, which claims priority under 35 U.S.C. § 119(b) to Chinese Application No. 201611141394.8, filed Dec. 12, 2016, the disclosures of which are incorporated herein by reference in their entirety.

FIELD OF THE INVENTION

The present invention provides a novel class of heterocyclic compounds, the synthesis and use thereof, for example, as Syk (Spleen tyrosine kinase) inhibitors and/or Syk-HDAC (Histone deacetylase) dual inhibitors.

BACKGROUND OF THE INVENTION

Syk is a non-receptor protein tyrosine kinase which is expressed in a variety of cells especially in various hematopoietic cells. It is expressed in monocytes, macrophages, mast cells, basophils, eosinophils, neutrophils, immature T cells, CD4 effector T cells, B cells, natural killer cells, dendritic cells, platelets and red blood cells. In addition, expression of Syk is detected also in fibroblasts, osteoclasts, endothelial cells, and nerve cells. Syk also presents in various tissues such as epithelial cells of the lung, kidney, and cardiomyocytes. In 1991, Taniguchi et al, isolated a protein kinase with a molecular weight of 72 kDa from the cDNA of pig spleen, and named it Syk. Syk contains 629 amino acid residues and consists of two tandem Src homodomains (N—SH2 and C—SH2) at the N-terminus and a kinase domain at the C-terminal. It shares a part of common structure with the protein kinase (ZAP-70), which is also a cytoplasmic protein kinase. Syk is activated by binding of the SH2 region to a tyrosine-dependent immunoreceptor tyrosinebased activation motifs (ITAM).

Spleen tyrosine kinase is involved in the signal transduction process of many cells, and has attracted extensive attention as a cell signal transduction factor, especially an immune signal transduction factor. Recent studies have shown that Syk plays a key role in inhibiting cell division and proliferation, and its overactivation can promote malignant cell proliferation and inhibit apoptosis, especially in B cells. Syk also affects the secretion of certain cytokines, and plays a key role in the production of cytokines in T cells and monocytes, bone resorption in osteoclasts, and phagocytosis of macrophages. Syk also affects the maturation and activation of immune cells and is closely related to allergic and antibody-mediated autoimmune diseases. Since Syk is located in the upstream of the cellular signaling pathway, treatments targeting to Syk are more advantageous than drugs that inhibit single downstream pathway. Therefore, Syk has been used as a potential therapeutic target for a variety of diseases, such as chronic inflammatory diseases such as rheumatoid arthritis, allergic diseases (allergic rhinitis and asthma), multiple sclerosis, and immune diseases (rheumatoid arthritis), multiple tumors (breast, stomach, rectal, pancreatic, liver, B-cell lymphoma, chronic lymphocytic leukemia, non-Hawkings lymphoma, etc.), atherosclerosis (coronary heart disease and cerebral arterial thrombosis), gastrointestinal disorders, idiopathic thrombocytopenic purpura, Wiskott-Aldrich syndrome, and systemic lupus erythematosus.

HDAC is a class of proteases that play an important role in the structural modification of chromosomes and the regulation of gene expression. HDAC deacetylates the lysine side chain at the amino terminus of histones, and histone acetylation is in a dynamic equilibrium with histone deacetylation, which is regulated by histone acetyltransferase (HAT) and histone deacetylase. The acetylation of hi stones reverses the acetylation of lysine residues of HAT and restores the positive charge of lysine residues, which facilitates the dissociation of DNA and histone octamers, and the relaxation of nucleosome structures, thus making various Transcription factors and co-transcription factors bind specifically to the DNA binding site and activate transcription of the gene. Due to the overexpression of HDAC in tumor cells, the deacetylation of histones is enhanced. By restoring the positive charge of histones and increasing the gravitation between DNA and histones, the relaxed nucleosomes become very tight, which is not conducive to specific Gene expression, including some tumor suppressor genes.

HDAC inhibitors can regulate the expression and stability of apoptosis and differentiation-related proteins by increasing histone acetylation in specific regions of chromatin, induce tumor cell cycle arrest and apoptosis, promote tumor cell autophagy, and inhibit the formation of tumor angiogenesis, promotes the immunogenicity of tumor cells. HDAC inhibitors not only become a target for therapy for tumors, but also play a role in neurological diseases, inflammation, and promotion of autoimmunity.

Preclinical and clinical studies have shown that HDAC inhibitors can also effectively synergistically inhibit tumor growth when combined with other anti-tumor compounds. HDAC is responsible for removing acetyl groups on histones, which shows significant effects on gene expression, oncoprotein stability, cell migration, protein catabolism, and cell cycle regulation.

Study of Hagiwara, K. et al. on 2015 published in *Apoptosis* confirmed that the combination of the Syk inhibitor 8406 and the HDAC inhibitor vorinostat has synergistically potentiating effects on killing mantle cell lymphoma cells.

In summary, Syk inhibitors or Syk-HDAC dual inhibitors would be able to used in a variety of cancers and other treatments for the disease.

SUMMARY OF THE INVENTION

The object of the present invention is to provide a structurally novel Syk inhibitors or Syk-HDAC dual inhibitors, and the preparation method and application thereof In the first aspect of the present invention, a compound of formula (I), or the pharmaceutically acceptable salts, prodrugs, deuterated derivatives, hydrates, or solvates thereof is provided:

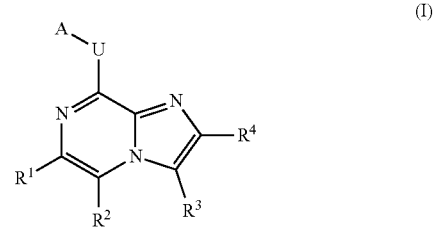

wherein in the formula (1),

R$^1$ is aryl, heteroaryl or 6-membered monocyclic heterocyclyl (including saturated and unsaturated); aryl, heteroaryl or monocyclic heterocyclyl herein may be optionally and independently substituted by 1-3 substituents each independently selected from the group consisting of: halogen, C$_{1-4}$ alkyl, C$_{1-4}$ halogenated alkyl, C$_{2-4}$ alkenyl, C$_{2-4}$ alkynyl, C$_{3-8}$ cycloalkyl, 3- to 8-membered heterocyclyl, aryl, heteroaryl, CN, NO$_2$, OR$^8$, SR$^8$, NR$^8$R$^9$, C(O)R$^8$, C(O)OR$^8$, C(O)NR$^8$R$^9$, S(O)$_2$R$^8$ or R$^7$.

R$^2$, R$^3$ and R$^4$ are hydrogen;

U is selected from NR$^5$; where R$^5$ is hydrogen;

A selected from the group consisting of formula (II) or formula (III):

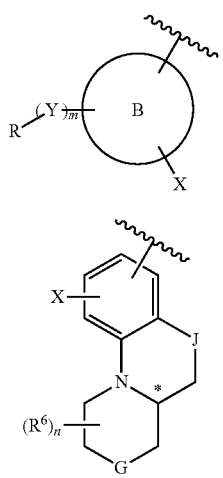

(II)

(III)

wherein:

"~~" refers to the connection point of formula (II) or formula (III) to U of the formula (I):

"*" indicates a chiral center;

B is a monocyclic aryl or bicyclic aryl group, or a monocyclic heteroaryl or bicyclic heteroaryl group, and at least one ring of the bicyclic aryl or bicyclic heteroaryl is aromatic, and the other ring is aromatic, saturated or partially saturated ring;

Y is 3- to 12-membered monocyclic or polycyclic heterocyclic ring; wherein said heterocyclic ring contains 1-4 heteroatoms each independently selected from N, O and S;

m is 0 or 1;

each X is independently hydrogen, halogen, C$_{1-4}$ alkyl, C$_{3-6}$ cycloalkyl, 3- to 6-membered heterocyclyl, CN, OR$^8$, SR$^8$, NR$^8$R$^9$, C(O)R$^8$, C(O)OR$^8$, C(O)NR$^8$R$^9$, or S(O)$_2$R$^8$;

R is hydrogen, —(CH$_2$)$_p$—V—(CH$_2$)$_q$C(O)NH(OH), —V$^1$—(CH$_2$)$_p$, —V$^2$—V—(CH$_2$), C(O)NH(OH);

R$^7$ is hydrogen, —(CH$_2$)$_p$—V—(CH$_2$)$_q$C(O)NH(OH), —V$^1$—(CH$_2$), —V$^2$—V—(CH$_2$)$_q$C(O)NH(OH), C(O)NH(OCH$_3$),

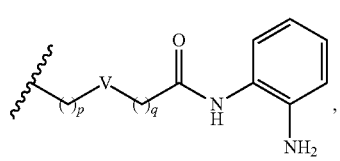

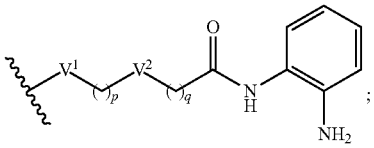

J is O;

G is NR$^{10}$;

n is 0, 1, 2, or 3;

each R$^6$ is hydrogen, or two R$^6$ connecting to the same carbon atom form carbonyl group (=O);

R$^8$ and R$^9$ are each independently hydrogen, C$_{1-4}$ alkyl, C$_{1-4}$ halogenated alkyl, C$_{2-4}$ alkenyl, C$_{2-4}$ alkynyl, C$_{3-8}$ cycloalkyl, 3- to 8-membered heterocyclyl, aryl, or heteroaryl; or R$^8$ and R$^9$ together with the nitrogen atom to which they are attached form a 3- to 9-metacyclic ring comprising 1-2 N atom and 0, 1 or 2 heteroatoms selected from O or S;

R$^{10}$ is C$_{2-8}$alkyl, C$_{1-8}$ haloalkyl, C$_{2-8}$ alkenyl, C$_{2-8}$ alkynyl, C$_{3-8}$ cycloalkyl, 3- to 12-membered heterocyclyl (optionally comprising 1-2 heteroatoms selected from O, N, or S), aryl, heteroaryl, C(O)R$^8$, C(O)OR$^8$, C(O)NR$^8$R$^9$, S(O)$_2$R$^8$ or (CH$_2$)—V—(CH$_2$)$_q$C(O)NH(OH), wherein R$^8$ is not hydrogen, and the R$^8$ in C(O)R$^8$ is not methyl;

V is a divalent group, each of p and q is independently an integer from 0 to 10, and the V is selected from the group consisting of bond, O, S, NR$^{11}$, OC(O), OC(O)O, NHC(O), NHC(O)NH, NHC(O)O, OC(O)NH, NHS(O)$_2$, C(O), C(O)O, C(O)NH, S(O), S(O)$_2$, S(O)$_2$NH, or NHS(O)$_2$NH, CH=CH, C=C, CR$^{12}$R$^{13}$, C$_{3-8}$ cycloalkyl, 3- to 12-member heterocyclyl, aryl or heteroaryl

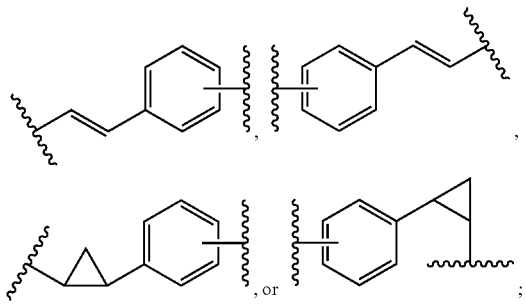

with the prerequisite that V, p and q together form a chemically stable group;

V$^1$ and V$^2$ are divalent groups selected from the group consisting of bond, O, S, NR$^{11}$, or C(O)N171_, with the prerequisite that the group formed by V, V$^1$, V$^2$, p and q is chemically stable group;

R$^{11}$ is hydrogen, C$_{1-4}$ alkyl, cycloalkyl, 3- to 8-membered heterocyclyl, aryl, heteroaryl, C(O)R$^8$ or S(O)$_2$R$^8$;

R$^{12}$ and R$^{13}$ are each independently hydrogen, halogen, C$_{1-4}$ alkyl, C$_{3-6}$ cycloalkyl, alkenyl, C$_{2-4}$ alkynyl, 3- to 8-membered heterocyclic, OR$^8$, SR$^8$, NR$^8$R$^9$, CN, C(O)R$^8$, C(O)OR$^8$, C(O)NR$^8$R$^9$, OC(O)R$^8$, NR$^8$C(O)R$^9$, or S(O)$_2$R$^8$, or R$^{12}$ and R$^{13}$ together with the carbon atoms to which they are attached form 3-8 membered cyclic structure containing 0, 1 or 2 heteroatoms selected from N, O, or S;

with the prerequisite that when the formula (II) is

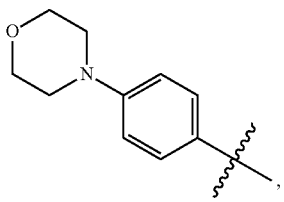 [SMILES: *c1ccc(N2CCOCC2)cc1 ; ","]

then the R¹ is

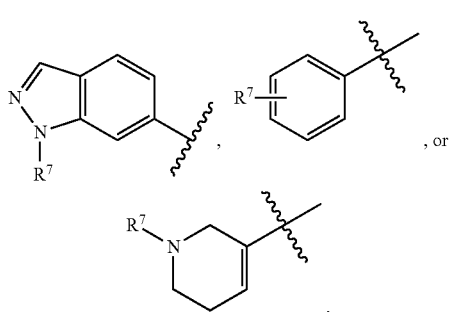

herein R⁷ is other than hydrogen, and the definitions of V, V¹, V², p and q in R⁷ must ensure that the formed R¹ group is a stable chemical structure;

another proviso is that when R¹ does not comprise structural unit

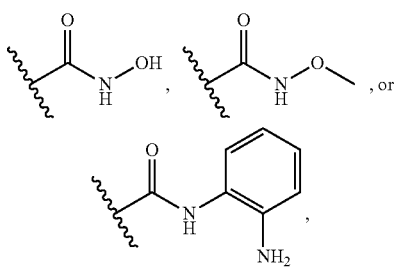

than A is of formula (IIa) or formula (IIIa), wherein R comprises structural unit

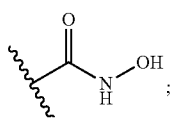

(IIa)

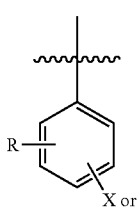

(IIIa)

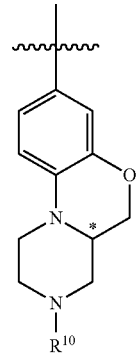

wherein each of the alkyl, alkenyl, alkynyl, cycloalkyl heterocyclyl, aryl and heteroaryl are each optionally and independently substituted by 1-3 substituents each independently selected from the group consisting of halogen, $C_{1-4}$ alkyl, $C_{1-4}$ halogenated alkyl, $C_{2-4}$ alkenyl, $C_{2-4}$ alkynyl, $C_{3-8}$ cycloalkyl, 3- to 8-heterocyclyl, aryl heteroaryl, CN, $NO_2$, $OR^8$, $SR^8$, $NR^8R^9$, C (O) $R^8$, $C(O)OR^8$, $C(O)NR^8R^9$ or $S(O)_2R^8$;

unless otherwise specified, the above aryl group is aryl group having 6 to 12 carbon atoms; and the heteroaryl group is 5- to 15-membered heteroaryl group.

In another preferred embodiment, the R¹ is

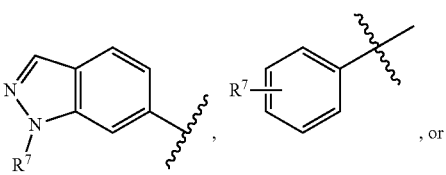

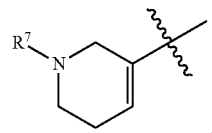

wherein the R⁷ is as defined above.

In another preferred embodiment, Y is a 4- to 12-membered monocyclic or polycyclic heterocycle having 1-4 heteroatoms each independently selected from N, O or S.

In another preferred embodiment, Y is a 4- to 10-membered monocyclic or polycyclic heterocycle having 1-3 heteroatoms each independently selected from N, O or S.

In another preferred embodiment, B is phenyl; Y is 6-membered monocyclic heterocyclic ring having 1-2 heteroatoms each independently being N, O or S, or Y is absent (m is 0).

In another preferred embodiment, formula (II) is a structure selected from the group consisting of:

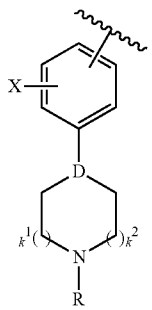

where D is N or CH;
$k^1$ and $k^2$ are each independently 0, 1, 2, or 3;
X is hydrogen, halogen, $C_{1-4}$ alkyl, CN, or $OR^5$;
R is hydrogen, $—(CH_2)_p—V—(CH_2)_qC(O)NH(OH)$, $—V^1—(CH_2)_p—V^2—V—(CH_2)_2C(O)NH(OH)$.

In another preferred embodiment, the formula (II) is a structure selected from the group consisting of:

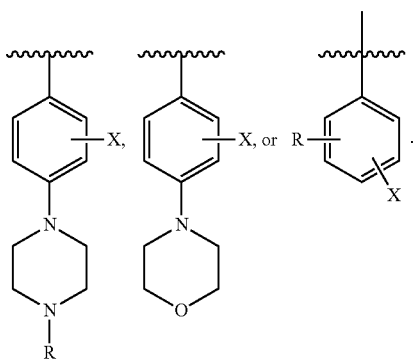

wherein X is hydrogen, halogen, $C_{1-4}$ alkyl, CN, or $OR^5$;
R is as described above.

In another preferred embodiment, the formula (III) is a structure selected from the group consisting of:

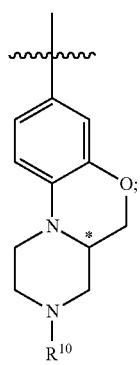

wherein $R^{10}$ is $C_{2-8}$ alkyl, $C_{1-8}$ halogenated alkyl, $C_{2-8}$ alkenyl, $C_{2-8}$ alkynyl, $C_{3-8}$ cycloalkyl, 6-membered heterocyclyl (optionally comprising 1-2 heteroatoms selected from O, N, S), aryl, heteroaryl, $C(O)R^8$, $C(O)OR^8$, $C(O)NR^8R^9$, $S(O)_2R^8$, wherein $R^8$ is selected from the group consisting of $C_{1-4}$ alkyl, $C_{1-4}$ haloalkyl, $C_{2-4}$ alkenyl, $C_{2-4}$ alkynyl, $C_{3-8}$ cycloalkyl, 3- to 8-membered heterocyclyl, aryl, or heteroaryl; wherein $R^8$ in $C(O)R^8$ is other than methyl; or $R^8$ and $R^9$ together with the nitrogen atom to which they are attached form a 3- to 9-membered ring comprising 1-2 N atom and 0, 1 or 2 hetero atoms selected from O or S.

In another preferred embodiment, R is $—(CH_2)_p—V—(CH_2)_qC(O)NH(OH)$ or $—V^1—(CH_2)_p—, —V^2—V—(CH_2)_qC(O)NH(OH)$; wherein V is bond, O, $NR^{11}$, CH=CH, aryl, heteroaryl, OC(O), NHC(O), C(O), $S(O)_2$; each is independently hydrogen or $C_{1-4}$ alkyl; p is 0, 1, 2, 3, or 4; q is 0, 1, 2, 3, 4, 5, 6, 7, or 8; $V^1$ and $V^2$ are each independently selected from $NR^{11}$, O, S, or bond; with the proviso that the group formed by V, $V^1$, and $V^2$, p and q together is a stable chemical structure.

In another preferred embodiment, each of $R^1$, $R^2$, $R^3$, $R^4$, U, A are the corresponding groups in compounds of the specific formula (I) prepared in the examples, respectively.

In another preferred embodiment, the formula (I) is selected from the group consisting of

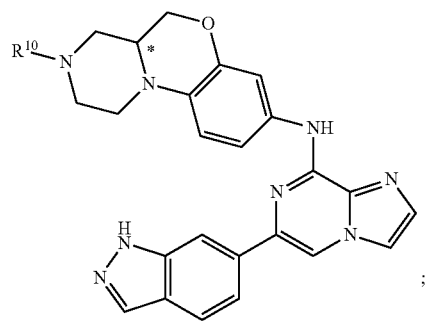

wherein $R^{10}$ is $C_{2-8}$ alkyl, $C_{1-8}$ haloalkyl, $C_{3-8}$ cycloalkyl, unsubstituted or $C_{1-4}$ alkyl substituted 6-membered heterocyclyl (optionally containing 1-2 heteroatoms selected from O, or N), $C(O)R^8$, or $S(O)_2R^8$; $R^8$ is $C_{14}$ alkyl or $C_{1-4}$ haloalkyl; wherein the $R^8$ in $C(O)R^8$ is other than methyl.

In another preferred embodiment, the $R^{10}$ is selected from the group consisting of ethyl, haloethyl cyclopropyl, phenyl, 6-heterocyclyl unsubstituted or substituted by $C_{1-4}$ alkyl (optionally containing 1-2 heteroatoms selected from O or N), 5-6 membered heteroaryl unsubstituted or substituted by $C_{1-4}$ alkyl (optionally containing 1-2 hetero atoms selected from O or N), $C(O)R^8$, $S(O)_2R^8$; wherein $R^8$ is $C_{1-4}$ alkyl or $C_{1-4}$ halogenated alkyl; wherein the $R^8$ in $C(O)R^8$ is other than methyl.

In another preferred embodiment, formula (I) is a structure selected from the group consisting of:

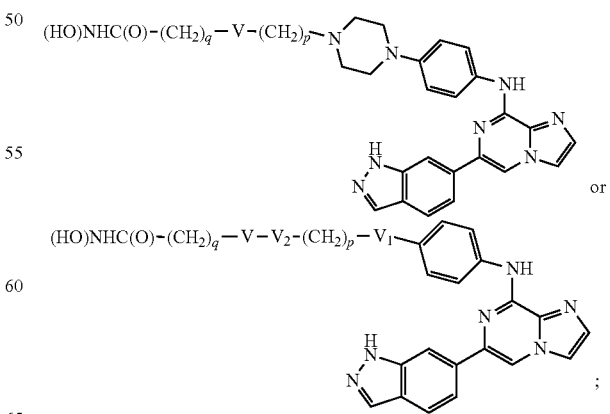

wherein V, $V^1$, $V^2$, p, and q are as defined above.

In another preferred embodiment, the formula (I) compound is a structure selected from the group consisting of:

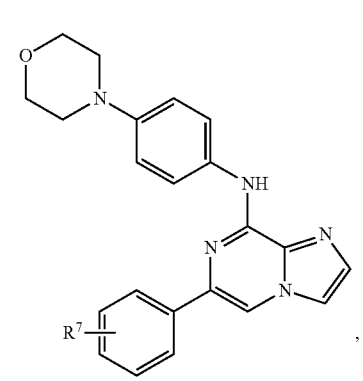

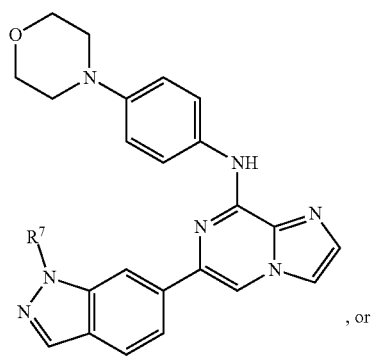
, or

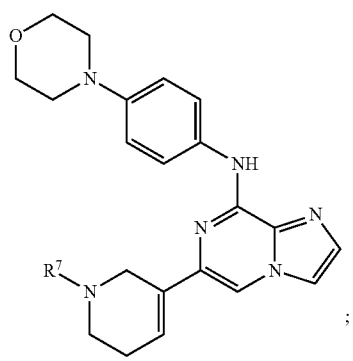
;

wherein $R^7$ is —$(CH_2)_p$—V—$(CH_2)_4C(O)NH(OH)$ or —$V^1$—$(CH_2)_p$—$V^2$—V—$(CH_2)_qC(O)NH(OH)$; wherein V is bond, O, $NR^{11}$, aryl, heteroaryl, OC(O), NHC(O), C(O), $S(O)_2$; each $R^{11}$ is independently hydrogen or $C_{1-4}$ alkyl; p is 0, 1, 2, 3, or 4; q is 0, 1, 2, 3, 4, 5, 6, 7, or 8; $V^1$ and $V^2$ are each independently selected from $NR^{11}$, O, S, or bond; with the proviso that the group formed by V, $V^1$, and $V^2$, p and q together is a stable chemical structure.

In another preferred embodiment, the compound is selected from the following group:

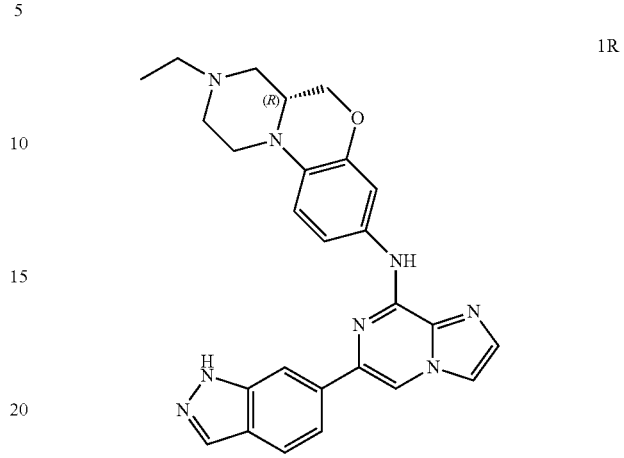
1R

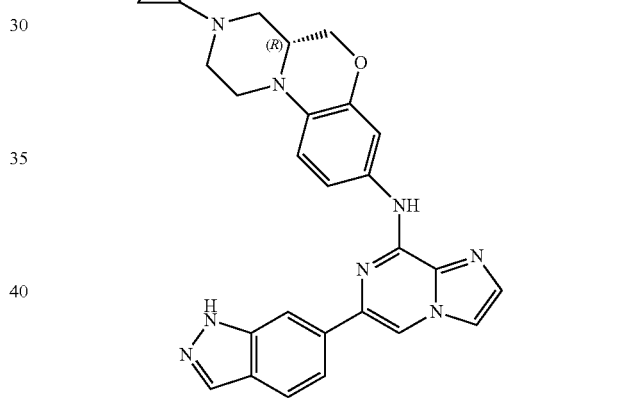
2R

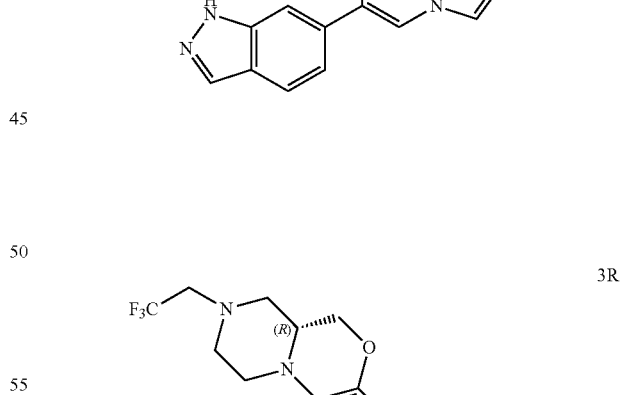
3R

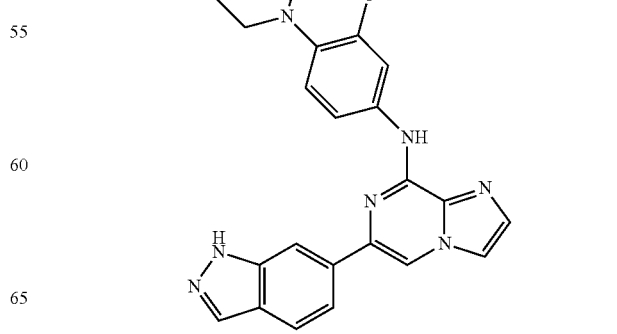

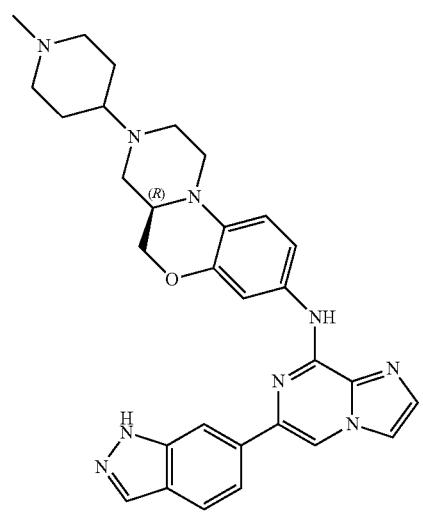
4R
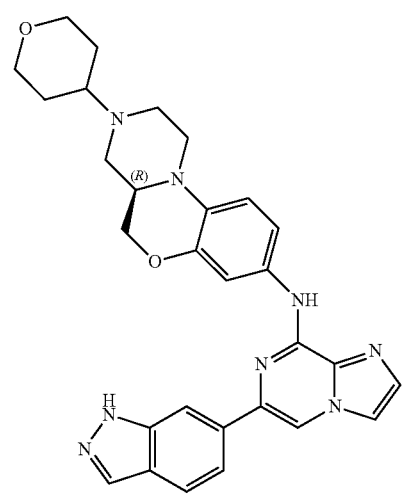
5R
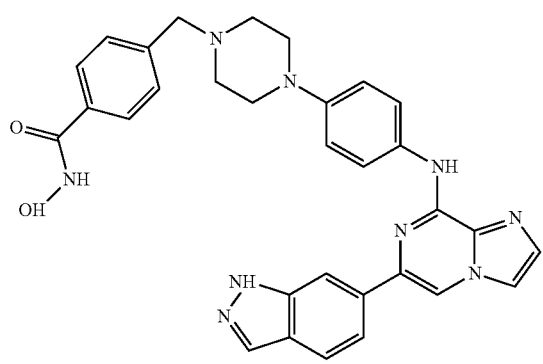
6
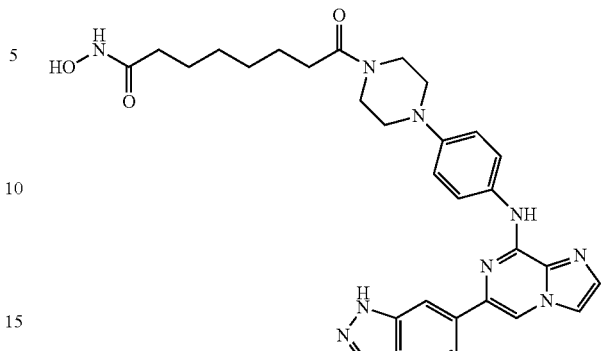
7
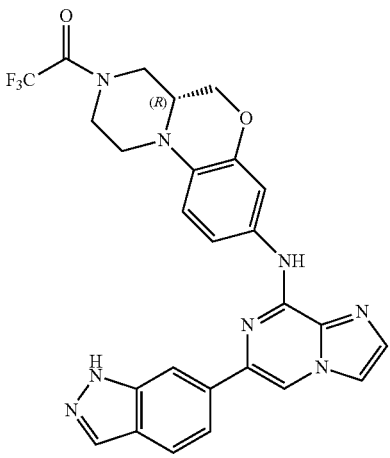
8R
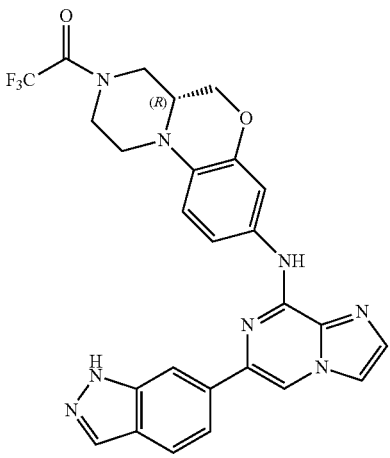
9R
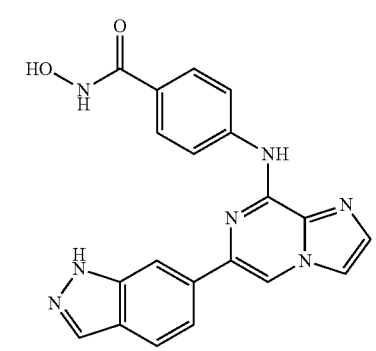
10

11
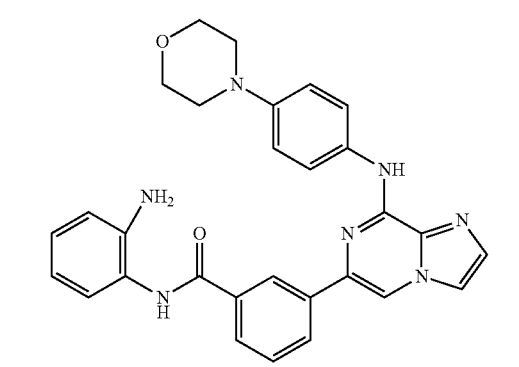
12
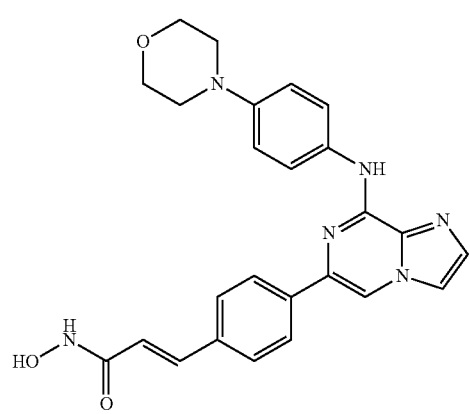
13
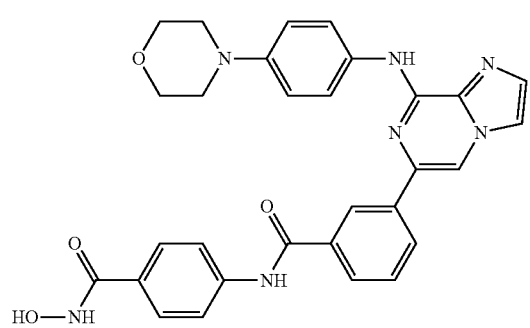
14
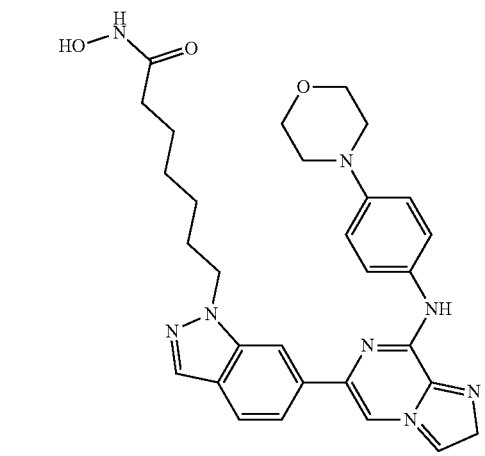
15
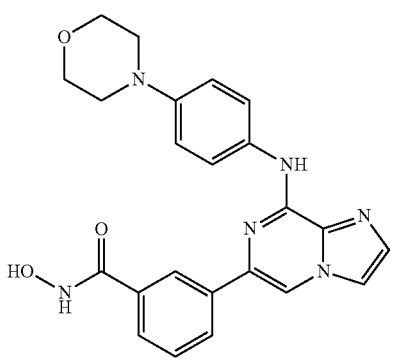
16
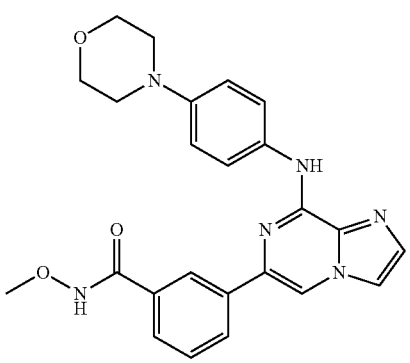
17
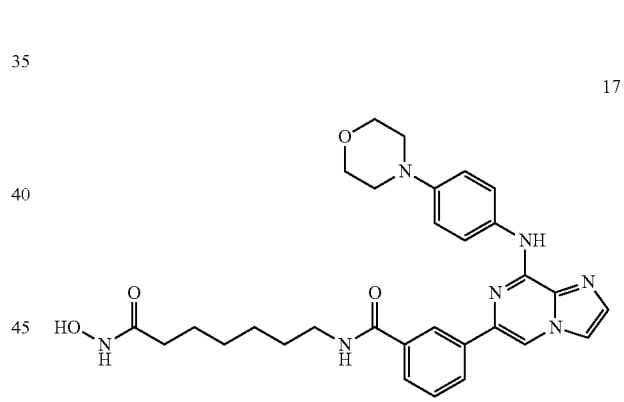
18
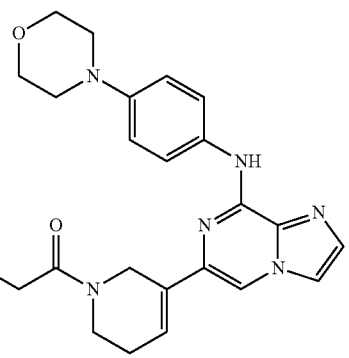

19
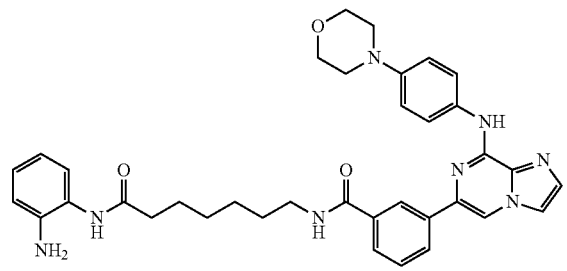
20
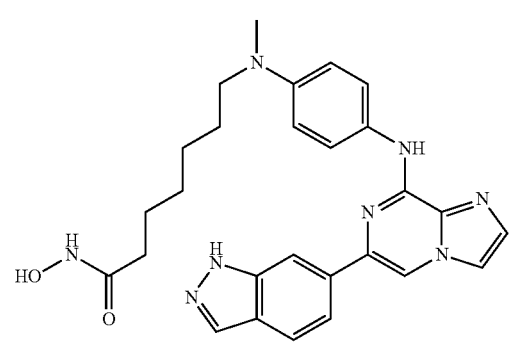
21
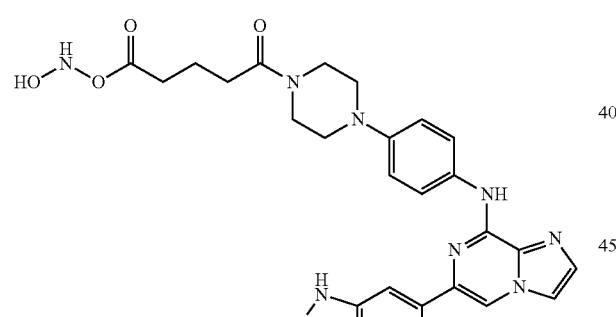
22
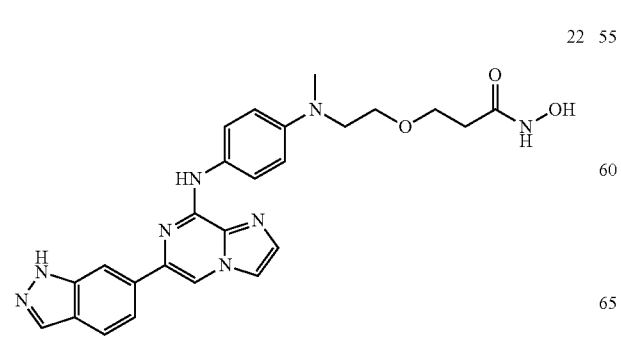
23
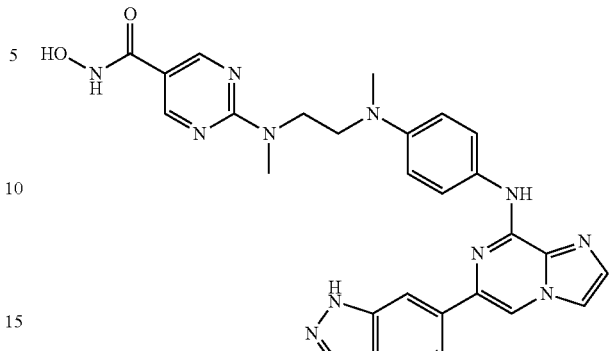
24
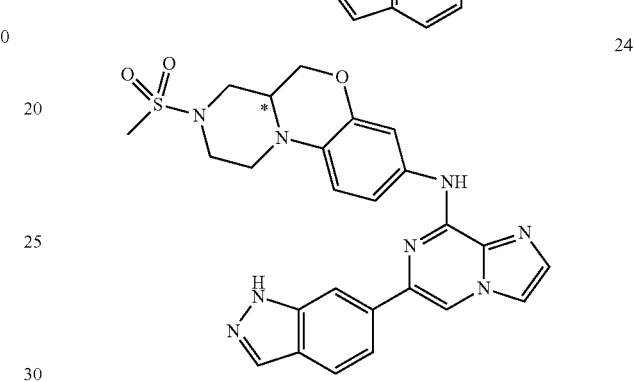
25
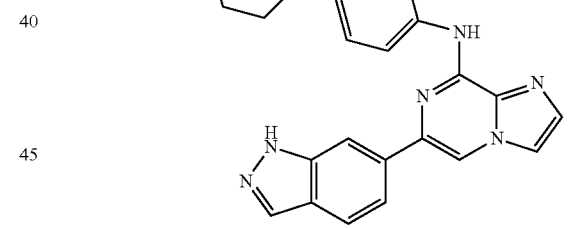
26
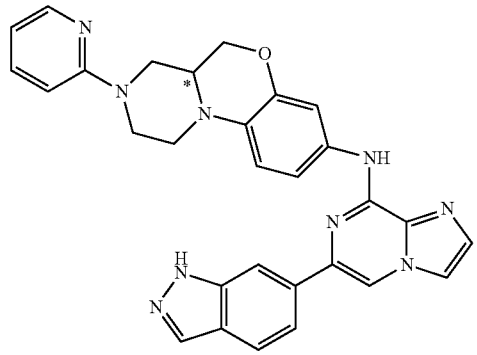

27

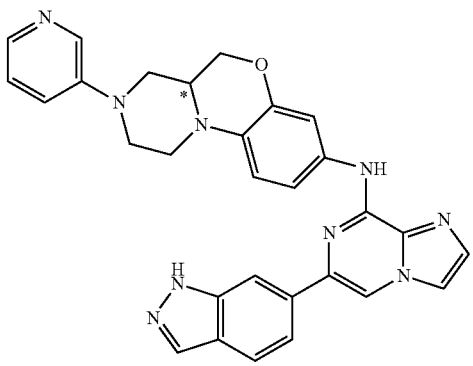

28

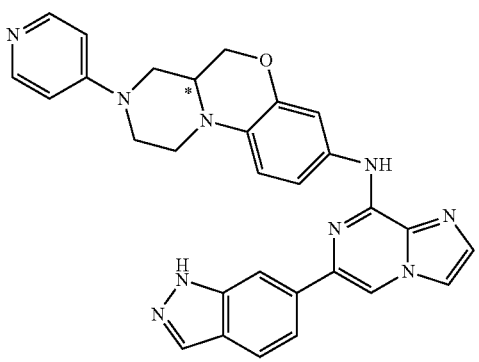

29

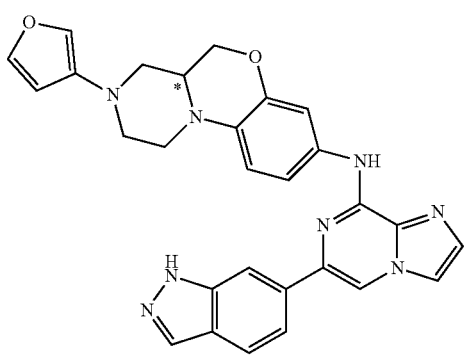

30

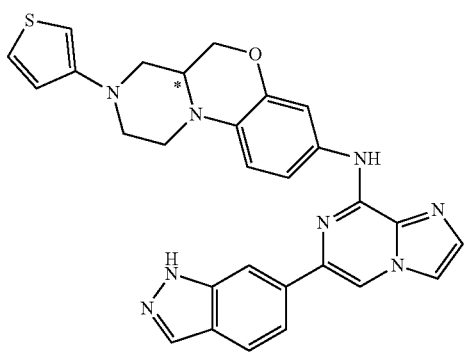

31

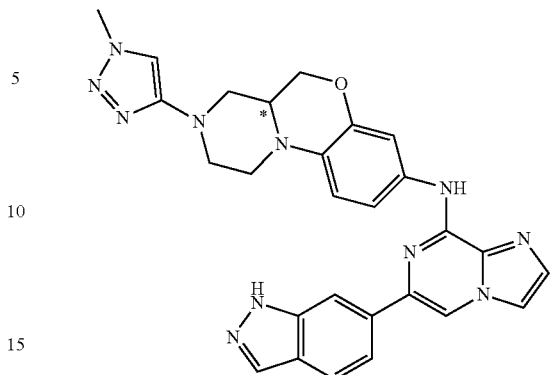

In the second aspect of the present invention, a use of compound of formula (I) according to the first aspect of the invention, or optical isomers, pharmaceutically acceptable salts, prodrugs, deuterated derivatives, hydrates, or solvates thereof is provided, wherein in:

(a) preparation of medicine for treating diseases associated with Syk and/or HDAC kinase activity or expression amount;

(b) preparation of Syk and/or HDAC kinase targeting inhibitor; and/or (c) in vitro non-therapeutic inhibition of Syk and/or HDAC kinase activity;

In another preferred embodiment, the formula (I) compound is used to treat diseases associated with Syk and/or HDAC kinase activity or expression amount.

In another preferred embodiment, a method of treating a disease associated with Syk and/or HDAC kinase activity or expression amount is provided, comprising the steps: administering a therapeutically effective amount of a compound of formula (I) to a subject in need.

In the third aspect of the present invention, a pharmaceutical composition is provided, which comprises: (i) therapeutically effective amount of formula (I) compound of the first aspect of the invention, or optical isomers, pharmaceutically acceptable salts, prodrugs, deuterated derivatives, hydrates, or solvates thereof, and (ii) pharmaceutically acceptable carrier.

In the fourth aspect of the present invention, the preparation method of compound of the first aspect of the present invention is provided, which comprises the following steps:

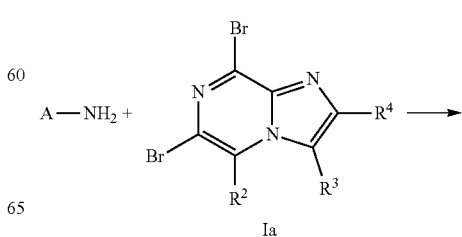

Ia

-continued

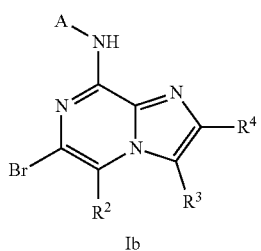
Ib (1) an inert solvent, compound Ia reacts with A—NH$_2$ so as to provide compound Ib;

(2) In an inert solvent, compound Ib reacts with compound R$^1$13(OH)$_2$ to obtain formula I compound;

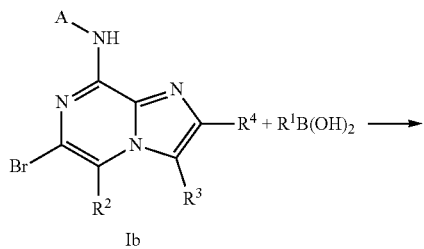

(3) The C(O)NH(OH) group in A or R$^1$ in the compound of formula (I) is prepared from the corresponding carboxylic ester. The carboxylic ester Ic or Id is hydrolyzed, and the resulting acid is further reacted with a tetrahydropyran protected hydroxylamine, and finally the tetrahydropyran protecting group is deprotected to give a hydroxyamide Ie or If. The general scheme is as follows:

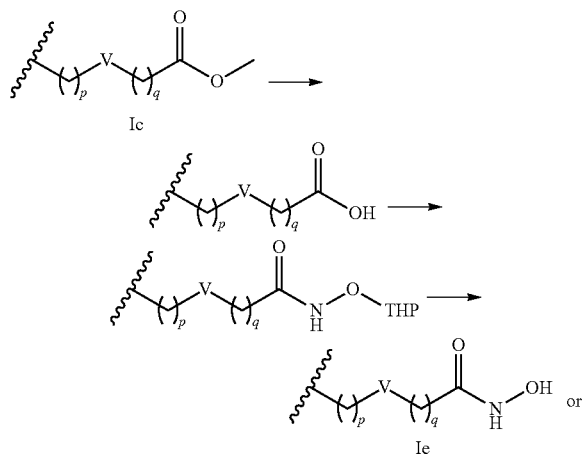

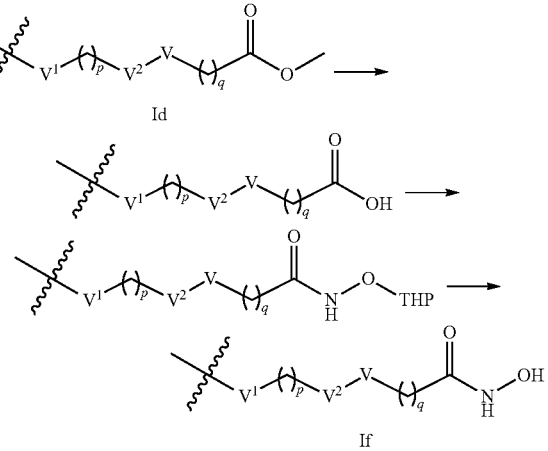

In the above formulas, the groups are defined as above.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

After long-term and intensive research, the inventors have unexpectedly discovered a class of heterocyclic compounds having Syk (spleen tyrosine kinase) inhibitory activity or Syk-HDAC dual inhibitory activity, thus being able to used in the preparation of pharmaceutical compositions for treating diseases associated with the activity or expression amount of Syk and or HDAC. The present invention is completed on this basis.

Terminology

Unless otherwise stated, "or" as used herein has the same meaning as "and/or" (refers to "or" and "and").

Unless otherwise specified, among all compounds of the present invention, each chiral carbon atom (chiral center) may optionally be in the R configuration or the S configuration, or a mixture of the R configuration and the S configuration.

As used herein, the term "alkyl", alone or as part of another substituent, refers to a straight (ie, unbranched) or branched saturated hydrocarbon group containing only carbon atoms, or a combination of straight and branched chains. When the alkyl group has a carbon number limitation (e.g., $C_{1-10}$), it means that the alkyl group has 1 to 10 carbon atoms. For example, $C_{1-8}$ alkyl refers to an alkyl group containing from I to 8 carbon atoms, including methyl, ethyl, propyl, isopropyl, butyl, isobutyl, sec-butyl, tent-butyl, or the like. Group.

As used herein, the term "alkenyl", when used alone or as part of another substituent, refers to a straight or branched, carbon chain group having at least one carbon-carbon double bond. Alkenyl groups can be substituted or unsubstituted. When the alkenyl group has a carbon number limit (e.g., $C_{2-8}$), it means that the alkenyl group has 2-8 carbon atoms. For example, $C_{2-8}$ alkenyl refers to alkenyl groups having 2-8 carbon atoms, including ethenyl, propenyl, 1,2-butenyl, 2,3-butenyl, butadienyl, or the like.

As used herein, the term "alkynyl", when used alone or as part of another substituent, refers to an aliphatic hydrocarbon group having at least one carbon-carbon triple bond. The alkynyl group can be straight or branched, or a combination thereof. When the alkynyl group has a carbon number limitation (e.g., C$_{2-8}$ alkynyl group), it means that the alkynyl group has 2 to 8 carbon atoms. For example, the term "C$_{2-8}$ alkynyl" refers to a straight or branched alkynyl group having 2-8 carbon atoms, including ethynyl, propynyl, isopropynyl, butynyl, isobutynyl, secondary Butynyl, tert-butynyl, or the like.

As used herein, when used alone or as part of another substituent, the term "cycloalkyl" refers to a unit ring having a saturated or partially saturated ring, a bicyclic or polycyclic (fused ring, bridged or spiro) ring system. When a certain cycloalkyl group has a carbon number limitation (e.g., C$_{3-10}$), it means that the cycloalkyl group has 3 to 10 carbon atoms. In some preferred embodiments, the term "C$_{3-8}$ cycloalkyl" refers to a saturated or partially saturated monocyclic or bicyclic alkyl group having from 3 to 8 carbon atoms, including cyclopropyl, cyclobutyl, cyclopentyl, cycloheptyl, or the like. "Spirocycloalkyl" refers to a bicyclic or polycyclic group that shares a. carbon atom (called a spiro atom) between the monocyclic rings. These may contain one or more double bonds, but none of the rings have fully conjugated π electrons system. "Fused cycloalkyl" means an all-carbon bicyclic or polycyclic group in which each ring of the system shares an adjacent pair of carbon atoms with other rings in the system, wherein one or more of the rings may contain one or more double bond, but none of the rings have a fully conjugated ,a-electron system. "Bridged cycloalkyl" refers to an all-carbon polycyclic group in which two rings share two carbon atoms that are not directly bonded, which may contain one or more double bonds, but none of the rings have a fully conjugated pi-electron system. The atoms contained in the cycloalkyl group are all carbon atoms. Some examples of cycloalkyl groups are as follows, and the present invention is not limited to the following cycloalkyl groups.

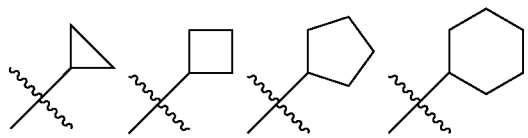

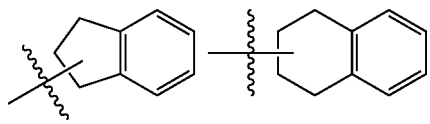

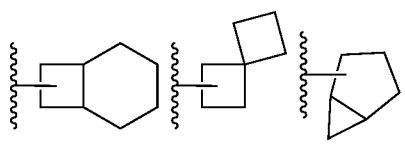

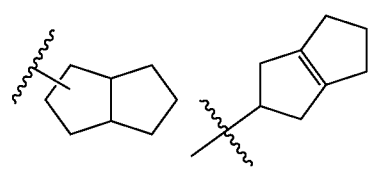

-continued

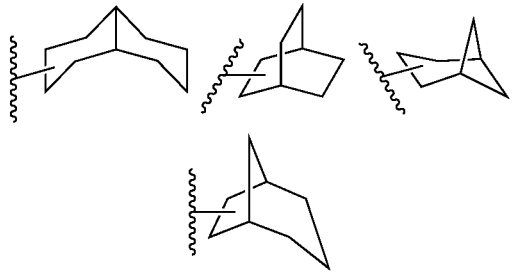

Unless otherwise stated, the following terms used in the specification and claims have the following meanings. "Aryl" means an all-carbon monocyclic or fused polycyclic (ie, a ring that shares a pair of adjacent carbon atoms) groups having a conjugated π-electron system, such as phenyl and naphthyl. The aryl ring may be fused to other cyclic groups (including saturated and unsaturated rings), but may not contain heteroatoms such as nitrogen, oxygen, or sulfur, while the point of attachment to the parent must be on the ring of carbon atoms of conjugated pi-electron system. The aryl group can be substituted or unsubstituted. The following are some examples of aryl groups, and the present invention is not limited to the aryl groups described below.

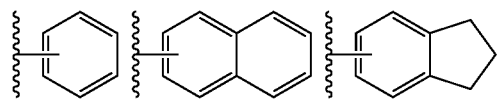

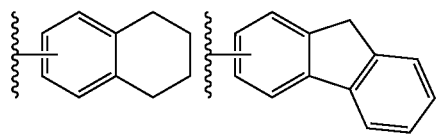

"Heteroaryl" refers to a heteroaromatic group containing one to more heteroatoms. The heteroatoms referred to herein include oxygen, sulfur, and nitrogen. For example, furyl thienyl, pyridyl, pyrazolyl, pyrrolyl, N-alkylpyrrolyl, pyrimidirryl, pyrazinyl, imidazolyl, tetrazolyl, and the like. The heteroaryl ring may be fused to an aryl, heterocyclic or cycloalkyl ring wherein the ring to which the parent structure is attached is a heteroaryl ring. The heteroaryl group can be optionally substituted or unsubstituted. The following are some examples of heteroaryl groups, and the present invention is not limited to the following heteroaryl groups. Among them, the last three heteroaryl groups are tricyclic heteroaryl groups, which are the focus of the present invention.

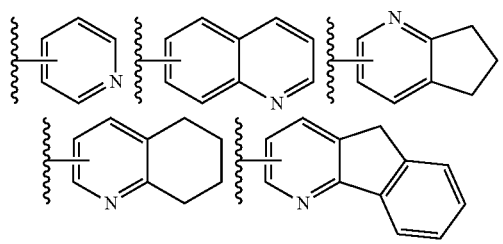

-continued

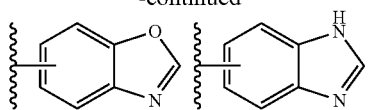

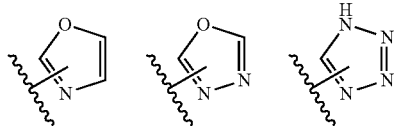

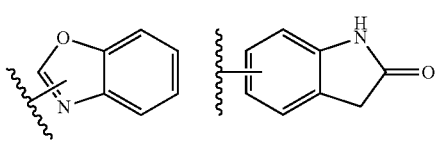

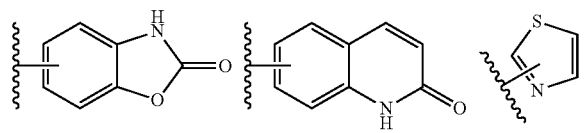

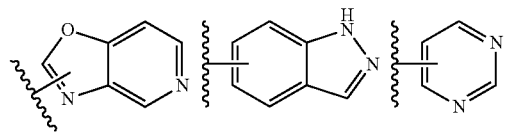

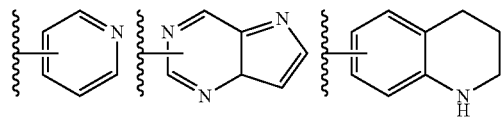

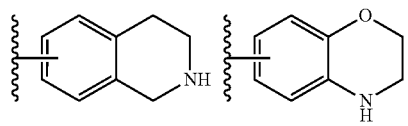

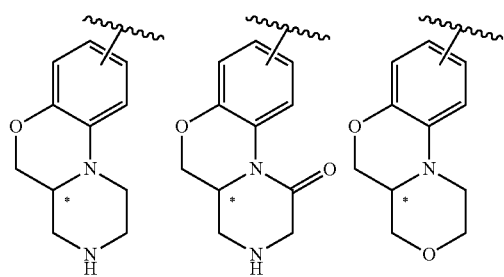

groups include pyrrolidinyl, piperidinyl, piperazinyl, morpholinyl, thiomorpholinyl, homopiperazinyl. Polycyclic heterocyclic group refers to a heterocyclic group including a spiro ring, a fused ring, and a bridged ring. "Spirocyclic heterocyclyl" refers to a polycyclic heterocyclic group in which each ring of the system shares an atom (referred to as a spiro atom) with other rings in the system, wherein one or more of the ring atoms is selected from the group consisting of nitrogen and oxygen. Or sulfur, the remaining ring atoms are carbon. "Fused ring heterocyclyl" refers to a polycyclic heterocyclic group in which each ring of the system shares an adjacent pair of atoms with other rings in the system, and one or more rings may contain one or more double bonds, but none One ring has a fully conjugated pi-electron system, and wherein one or more ring atoms are selected from nitrogen, oxygen or sulfur, and the remaining ring atoms are carbon. "Bridged heterocyclyl" refers to a polycyclic heterocyclic group in which any two rings share two atoms which are not directly bonded, these may contain one or more double bonds, but none of the rings have a fully conjugated pi-electron system And wherein one or more of the ring atoms are selected. from nitrogen, oxygen or sulfur, and the remaining ring atoms are carbon. If a heterocyclic group has both a saturated ring and an aromatic ring (for example, the saturated ring and the aromatic ring are fused together), the point attached to the parent must be on the saturated ring. Note: When the point attached to the parent is on the aromatic ring, it is called a heteroaryl group and is not called a heterocyclic group. Some examples of the heterocyclic group are as follows, and the present invention is not limited to the following heterocyclic group.

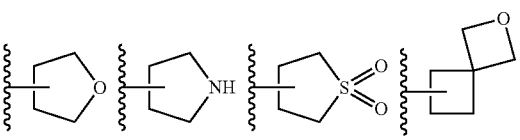

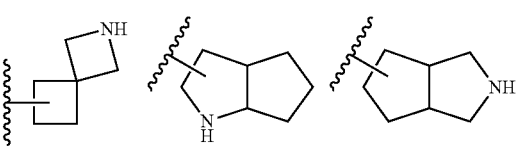

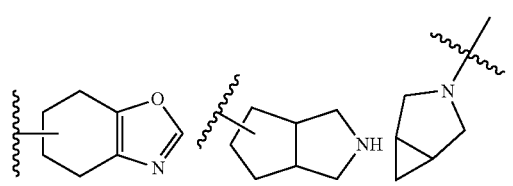

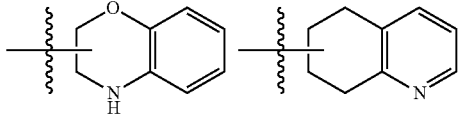

"Heterocyclyl" means a saturated or partially unsaturated monocyclic or polycyclic cyclic hydrocarbon substituent wherein one or more of the ring atoms are selected from nitrogen, oxygen or sulfur and the remaining ring atoms are carbon, Non-limiting examples of monocyclic heterocyclic

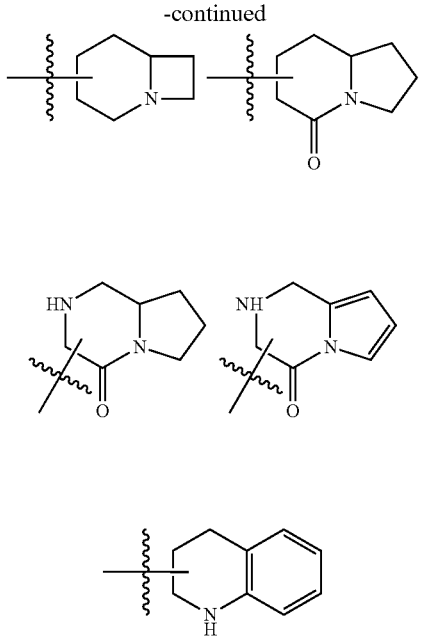

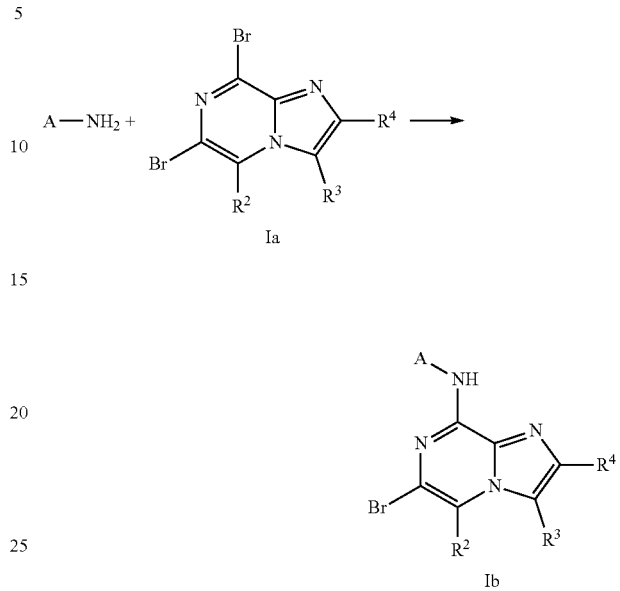

General Synthetic Method of Compounds

The compound of the formula (I) of the present invention can be prepared by the following method:

(1) in an inert solvent, reacting formula Ia compound with A—NH$_2$ so as to provide compound Ib;

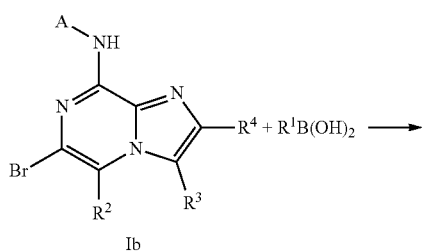

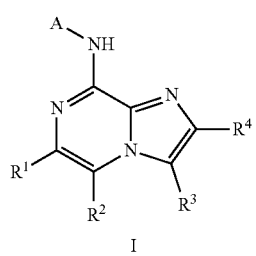

(2) In an inert solvent, reacting compound Ib and R$^1$B(OH)$_2$ compound to obtain formula I compound;

In the above formulas, the groups are defined as above. The reagents and conditions for each step may be selected from those conventional in the art for carrying out such preparation methods. After the structure of the compound of the present invention is disclosed, the above selection may be carried out by those skilled in the art based on the knowledge in the art.

More specifically, the compound of the formula I of the present invention can be obtained by the following method, As used herein, the term "halogen", when used alone or as part of another substituent, refers to F, Cl, Br, and I.

As used herein, the term "substituted" (when with or without "optionally") means that one or more hydrogen atoms on a particular group are replaced by a particular substituent. Particular substituents are the substituents described above in the corresponding paragraphs, or the substituents which appear in the examples. Unless otherwise stated, an optionally substituted group may have a substituent selected from a particular group at any substitutable position of the group, and the substituents may be the same or different at each position. A cyclic substituent, such as a heterocyclic group, may be attached to another ring, such as a cycloalkyl group, to form a spirobicyclic ring system, i.e., the two rings have a common carbon atom. Those skilled in the art will appreciate that the combinations of substituents contemplated by the present invention are those that are stable or chemically achievable. The substituents are, for example but not limited to, C$_{1-8}$ alkyl, C$_{2-8}$ alkenyl, C$_{3-8}$ cycloalkyl, 3- to 12-membered heterocyclic, aryl, Heteroaryl, halogen, hydroxy, carboxy (—COOH), C$_{1-8}$ aldehyde, C$_{2-10}$ acyl, C$_{2-10}$ ester, amino.

For convenience and in accordance with conventional understanding, the term "optionally substituted" or "optionally substituted" applies only to sites which are capable of being substituted by a substituent, and does not include those which are not chemically achievable.

As used herein, unless otherwise specified, the term "pharmaceutically acceptable salt" refers to a salt that is suitable for contact with the tissue of a subject (eg, a human) without causing unpleasant side effects. In some embodiments, a pharmaceutically acceptable salt of a compound of the invention includes a salt (eg, a potassium salt, a sodium salt, a magnesium salt, a calcium salt) of a compound of the invention having an acidic group or is basic A salt of a compound of the invention (e.g., a sulfate, a. hydrochloride, a phosphate, a nitrate, a carbonate).

however, the conditions of the method, such as the reactant, the solvent, the base, the amount of the compound used, the reaction temperature, the reaction time, are not limited to the explanation below. The compounds of the invention may also be easily prepared by optionally combine various synthetic methods described in this specification or known in the art, such a combination can be easily performed by one of ordinary skill in the art of the present invention.

In the production method of the present invention, each reaction is usually carried out in an inert solvent, and the reaction temperature is usually −20 to 150° C. (preferably 0 to 120° C.). The reaction time of each step is usually 0.5 to 48 h, preferably 2 to 12 h.

General synthesis method:

Scheme A describes the general synthesis method of the compounds A9-1 and A9-2:

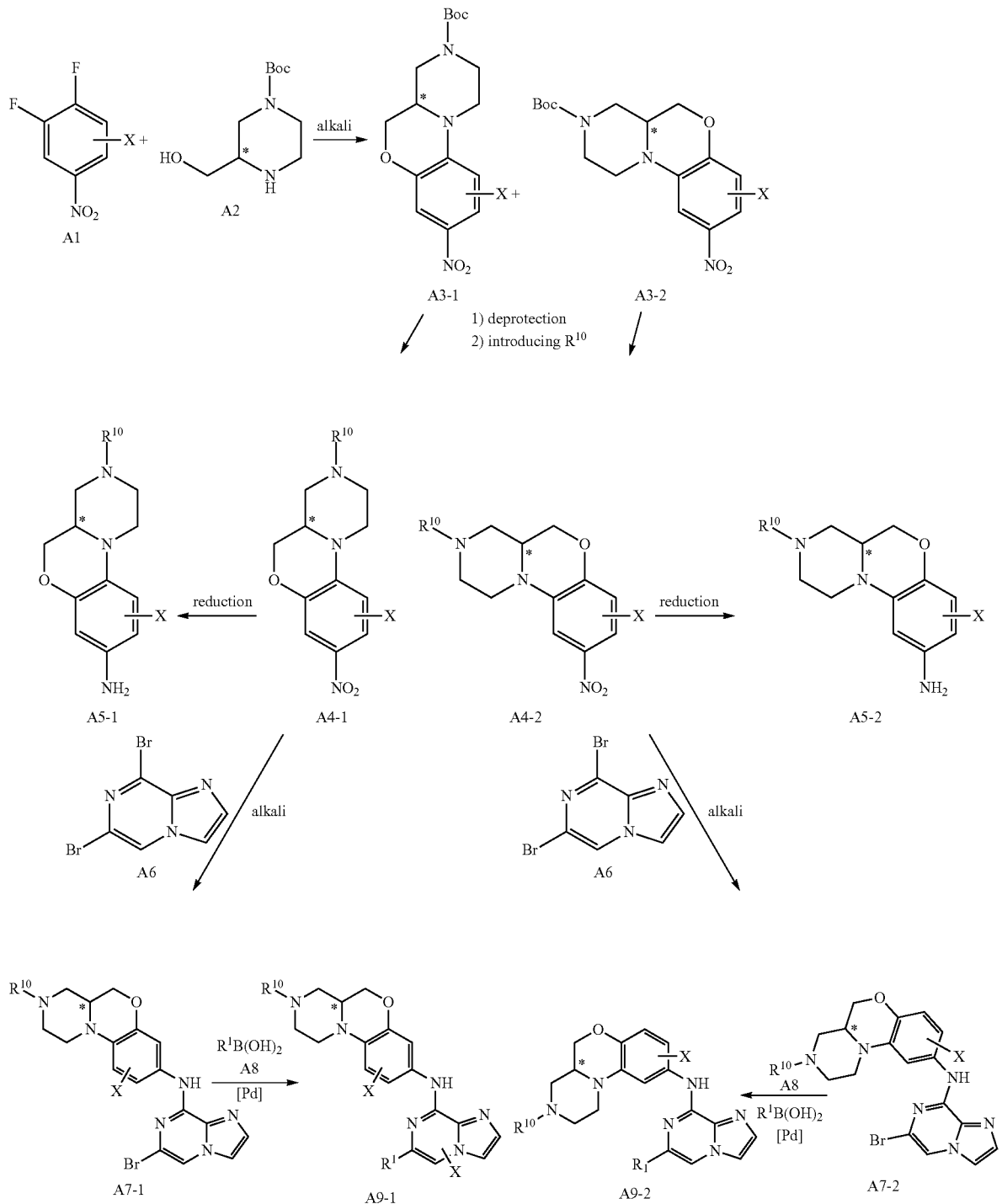

Scheme B describes the general synthesis method of the compound B4:
Scheme B
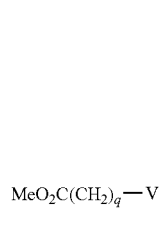 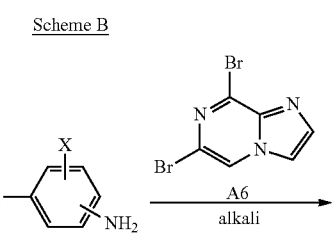 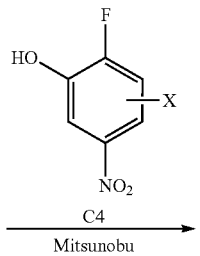
B1
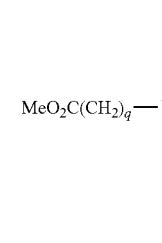 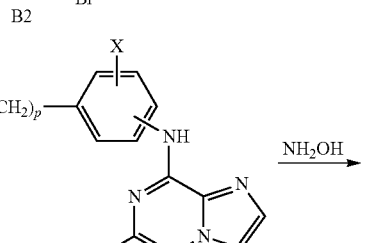
B2
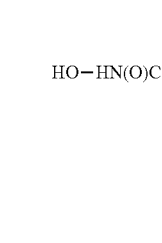 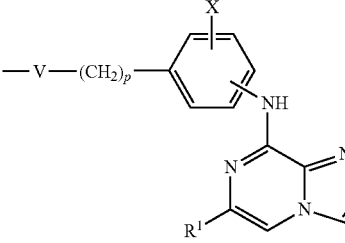
B3
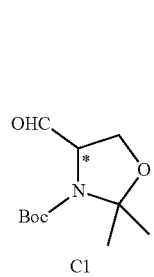 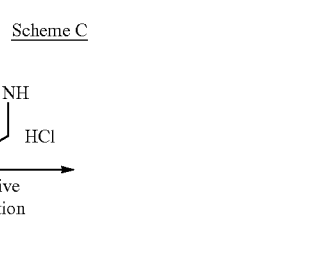
B4
Scheme C describes the general synthesis method of the compound C9:
Scheme C
 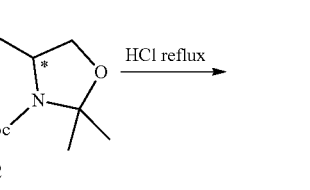
C1
C2
-continued
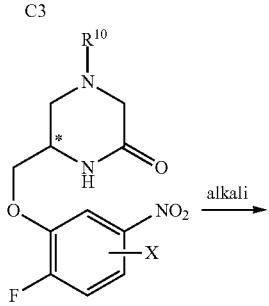
C3
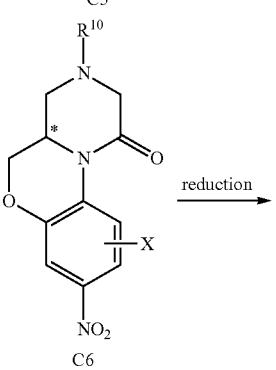
C5
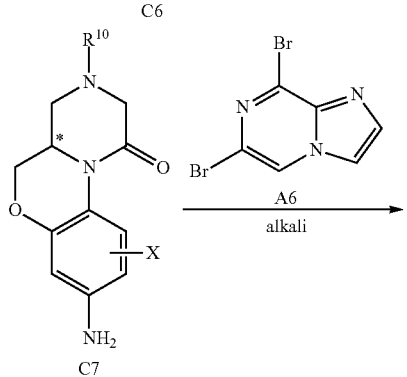
C6
C7
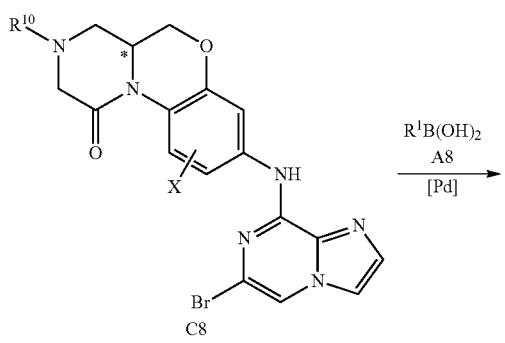
C8

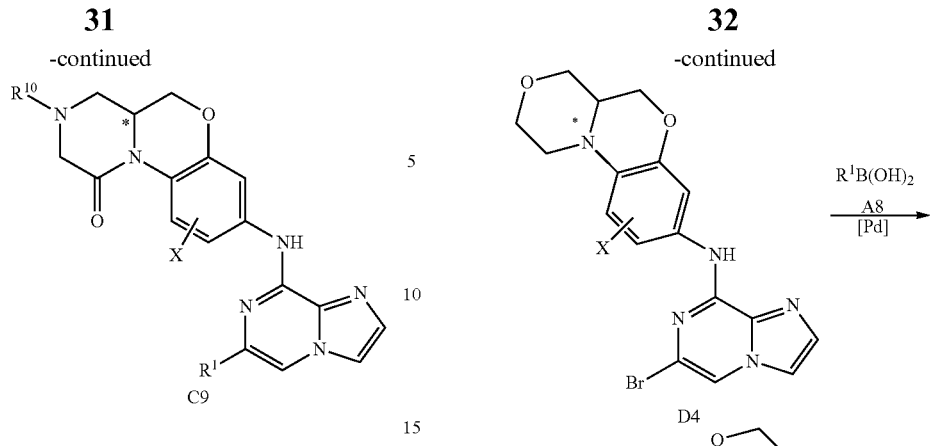

Scheme D describes the general synthesis method of the compound D5:

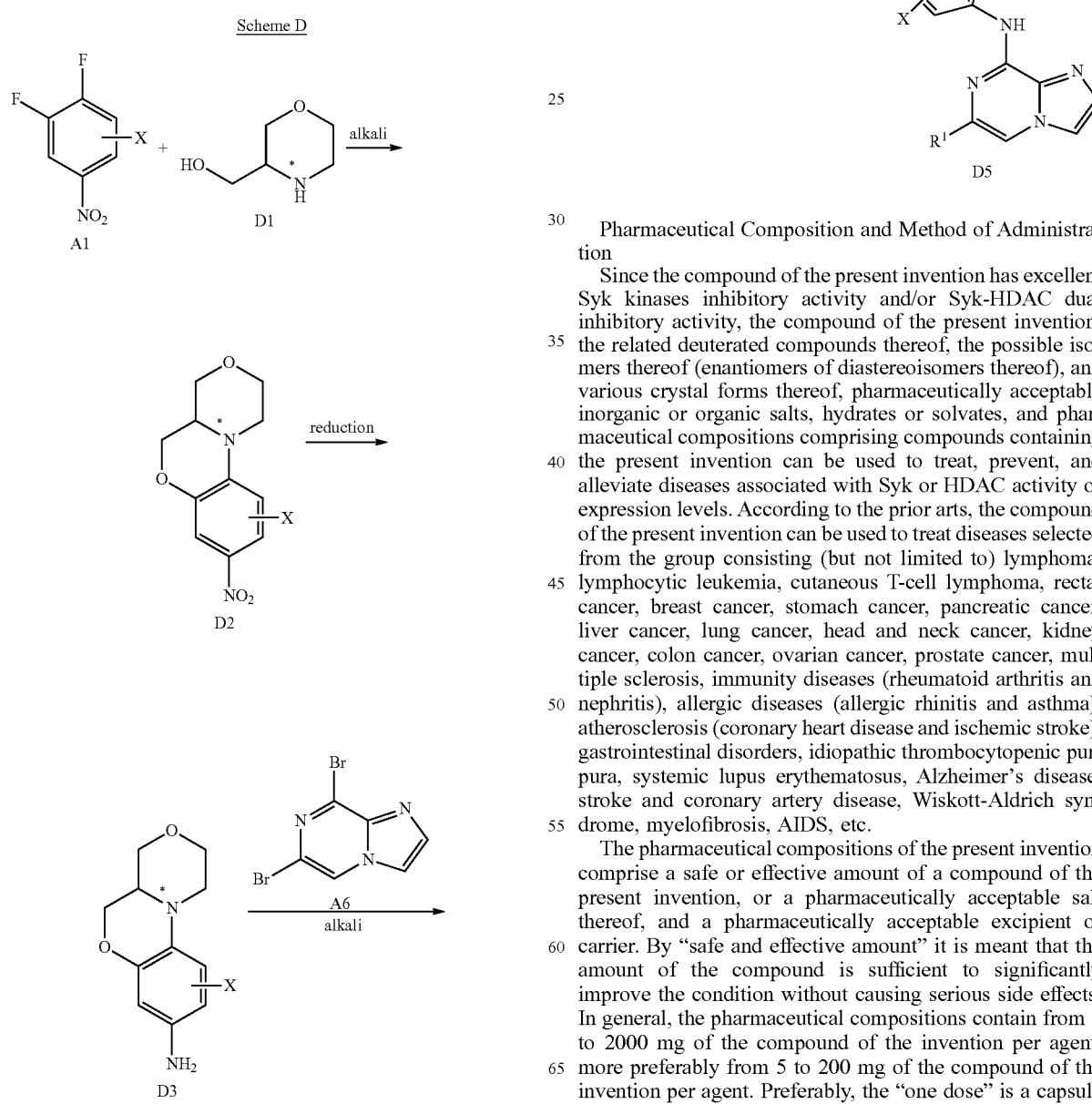

Pharmaceutical Composition and Method of Administration

Since the compound of the present invention has excellent Syk kinases inhibitory activity and/or Syk-HDAC dual inhibitory activity, the compound of the present invention, the related deuterated compounds thereof, the possible isomers thereof (enantiomers of diastereoisomers thereof), and various crystal forms thereof, pharmaceutically acceptable inorganic or organic salts, hydrates or solvates, and pharmaceutical compositions comprising compounds containing the present invention can be used to treat, prevent, and alleviate diseases associated with Syk or HDAC activity or expression levels. According to the prior arts, the compound of the present invention can be used to treat diseases selected from the group consisting (but not limited to) lymphoma, lymphocytic leukemia, cutaneous T-cell lymphoma, rectal cancer, breast cancer, stomach cancer, pancreatic cancer, liver cancer, lung cancer, head and neck cancer, kidney cancer, colon cancer, ovarian cancer, prostate cancer, multiple sclerosis, immunity diseases (rheumatoid arthritis and nephritis), allergic diseases (allergic rhinitis and asthma), atherosclerosis (coronary heart disease and ischemic stroke), gastrointestinal disorders, idiopathic thrombocytopenic purpura, systemic lupus erythematosus, Alzheimer's disease, stroke and coronary artery disease, Wiskott-Aldrich syndrome, myelofibrosis, AIDS, etc.

The pharmaceutical compositions of the present invention comprise a safe or effective amount of a compound of the present invention, or a pharmaceutically acceptable salt thereof, and a pharmaceutically acceptable excipient or carrier. By "safe and effective amount" it is meant that the amount of the compound is sufficient to significantly improve the condition without causing serious side effects. In general, the pharmaceutical compositions contain from 1 to 2000 mg of the compound of the invention per agent, more preferably from 5 to 200 mg of the compound of the invention per agent. Preferably, the "one dose" is a capsule or tablet.

"Pharmaceutically acceptable carrier" means: one or more compatible solid or liquid fillers or gel materials which are suitable for human use and which must be of sufficient purity and of sufficiently low toxicity. By "compatibility" it is meant herein that the components of the composition are capable of intermingling with the compounds of the invention and with each other without significantly reducing the efficacy of the compound.

Examples of pharmaceutically acceptable carriers are cellulose and its derivatives (such as sodium carboxymethylcellulose, sodium ethylcellulose, cellulose acetate, etc.), gelatin, talc, solid lubricants (such as stearic acid). , magnesium stearate), calcium sulfate, vegetable oils such as soybean oil, sesame oil, peanut oil, olive oil, etc.), polyols (such as propylene glycol, glycerin, mannitol, sorbitol, etc.), emulsifiers (such as Tween®), run Wet agents (such as sodium lauryl sulfate), colorants, flavoring agents, stabilizers, antioxidants, preservatives, pyrogen-free water, and the like.

The mode of administration of the compound or pharmaceutical composition of the present invention is not particularly limited, and representative modes of administration include, but are not limited to, oral, intratumoral, rectal, parenteral (intravenous, intramuscular or subcutaneous), and topical administration.

Solid dosage forms for oral administration include capsules, tablets, pills, powders, and granules. In these solid dosage forms, the active compound is mixed with at least one conventional inert excipient (or carrier), such as sodium citrate or dicalcium phosphate, or mixed with: (a) a filler or compatibilizer, for example, Starch, lactose, sucrose, glucose, mannitol and silicic acid; (b) a binder such as hydroxymethylcellulose, alginate, gelatin polyvinylpyrrolidone, sucrose, and acacia; (c) a humectant such as glycerin; (d) a disintegrant, for example, Agar, calcium carbonate, potato starch or tapioca starch, alginic acid. certain complex silicates, and sodium carbonate; (e) a slow solvent such as paraffin; (f) an absorption accelerator, for example, a quaternary amine compound; (g) Wetting agents such as cetyl alcohol and glyceryl monostearate; (h) an adsorbent, for example, kaolin; and (i) a lubricant such as talc, calcium stearate, magnesium stearate, solid polyethylene glycol, sodium lauryl sulfate, or a mixture thereof. In capsules, tablets and pills, the dosage form may also contain a buffer.

Solid dosage forms such as tablets, dragees, capsules, pills, and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric and waxy materials. If necessary, the active compound may also be in microencapsulated form with one or more of the above-mentioned excipients.

Liquid dosage forms for oral administration include pharmaceutically acceptable emulsions, solutions, suspensions, syrups or elixirs. In addition to the active compound, the liquid dosage form may contain inert diluents conventionally employed in the art, such as water or other solvents, solubilizers and emulsifiers for example ethanol, isopropanol, ethyl carbonate ethyl acetate, propylene glycol, 1,3-butanediol, dimethylformamide and oils, especially cottonseed oil, peanut oil, corn germ oil, olive oil, castor oil and sesame oil or a mixture of these substances.

In addition to these inert diluents, the compositions may contain adjuvants such as wetting agents, emulsifying and suspending agents, sweetening agents, flavoring agents and perfumes.

In addition to the active compound, the suspension may contain suspending agents, for example, ethoxylated isostearyl alcohol, polyoxyethylene sorbitol and sorbitan esters, microcrystalline cellulose, aluminum methoxide and agar or mixtures of these and the like.

Compositions for parenteral injection may comprise a physiologically acceptable sterile aqueous or nonaqueous solution, dispersion, suspension or emulsion, and a sterile powder for reconstitution into a sterile injectable solution or dispersion. Suitable aqueous and nonaqueous vehicles, diluents, solvents or vehicles include water, ethanol, polyols, and suitable mixtures thereof.

Dosage forms for the compounds of the invention for topical administration include ointments, powders, patches, propellants and inhalants. The active ingredient is admixed under sterile conditions with a physiologically acceptable carrier and any preservatives, buffers, or, if necessary. propellants.

The compounds of the invention may be administered alone or in combination with oilier pharmaceutically acceptable compounds.

When a pharmaceutical composition is used, a safe and effective amount of a compound of the invention is administered to a mammal (e.g., a human) in need of treatment wherein the dosage is a pharmaceutically effective dosage, for a 60 kg body weight. The dose to be administered is usually from 1 to 2000 mg, preferably from 5 to 500 mg. Of course, specific doses should also consider factors such as the route of administration, the health of the patient, etc., which are within the skill of the skilled physician.

The main advantages of the present invention are:

1. Provided a compound of formula I.

2. Provided a novel Syk kinase inhibitor and/or Syk-HDAC dual inhibitor and the preparation and use thereof. The inhibitor can inhibit the activities of Syk and HDAC kinases at very low concentrations.

3. Provided a pharmaceutical composition for the treatment of diseases associated with the activity of Syk or HDAC kinase.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Example 1

Preparation of Compound 1R

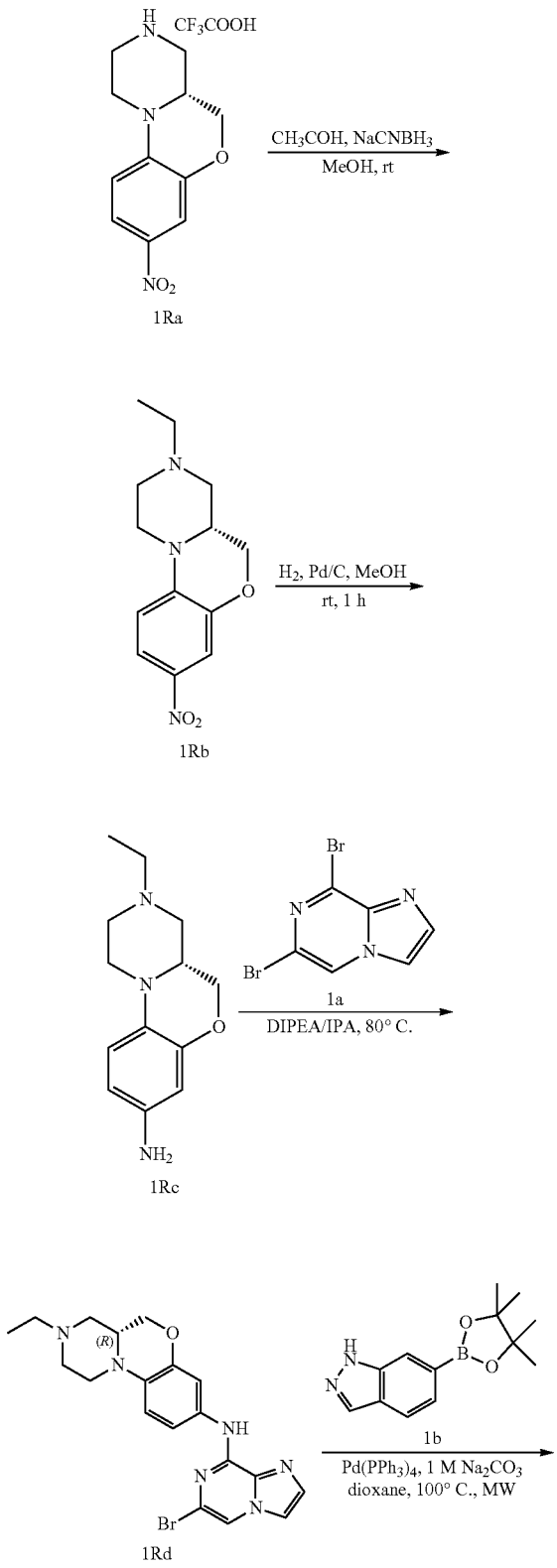

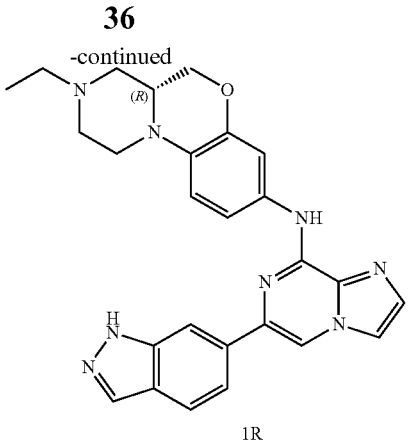

The trifluoroacetic acid salt of compound 1Ra (590 mg, 1.69 mmol) and acetaldehyde (1.30 g, 29.45 mmol) were dissolved in methanol (30 ml). Under stirring, sodium cyanoborohydride (678 mg, 10.79 mmol) was added in batches, and the temperature was controlled at below 10° C. The reaction was stirred at room temperature for 1 hour, TLC monitoring showed that the reaction was completed, then the solvent was removed under reduced pressure at room temperature. The residue was dispersed in a saturated sodium carbonate solution and extracted with ethyl acetate (25 ml×3). The combined organic layers were washed with brine and dried over anhydrous sodium sulfate. The crude product obtained by concentrating the filtrate under reduced pressure was separated by silica gel column (dichloromethane/methanol=50/1 solvent mixture elution) to obtain a yellow solid compound 1Rb (430 mg, yield 97%). $^1$H NMR (CDCl$_3$, 400 MHz) δ 7.80 (dd, J=9.2 Hz, 2.8 Hz, 1 H), 7.65 (d, J=2.8 Hz, 1 H), 674 (d, J=9.2 Hz, 1 H), 4.26 (dd, J=108 Hz, 2.8 Hz, 1 H), 4.00 (dd, J=10.8 Hz, 8,4 Hz, 1 H), 3.80-3,74 (m, 1l1), 3.43-3.36 (m, 1 H), 3.08-2.90 (m, 3H), 2.50-2.46 (m, 2 H), 2.21-2.14 (m, 1 H), 1.81 (dd, J=7.6 Hz, 7.2 Hz, 1 H), 1.13 (t, J=7.2 Hz, 3H); MS m/z 264.2 [M+H]$^+$.

Compound 1Rb (408 mg, 1.55 mmol) was placed in a 50 ml single-necked flask, dissolved in methanol (3 ml), and then Pd/C (10%, 40 mg) was added. The air in the bottle was replaced with hydrogen gas, and the reaction was stirred at room temperature for 1 hour wider a hydrogen atmosphere (one atmosphere). TLC monitoring showed that the reaction was completed, the reaction mixture was filtered, and the filtrate was concentrated under reduced pressure to give a brown solid compound 1Rc (361 mg, yield 99%). The compound was used in the next step without purification.

Compound 1Rc (33 mg, 0.142 mmol) was suspended in isopropanol (2 ml), and DIPEA (55 mg, 0.426 mmol) and 6,8-dibromo-imidazole [1,2-α] pyrazine (Compound 1a, 39 mg, 0.142 mmol) was added, then the reaction mixture was heated to 80° C. to react for 16 hours, The reaction mixture was cooled to room temperature and concentrated under reduced pressure. The crude product was purified by preparative thin chromatographed (dichloromethane/methanol=40/1 mixed solvent elution) to obtain pale yellow solid compound 1Rd (28 mg, 46% yield). MS m/z 429.0 [M+H]$^+$, 431.0 [M+H]$^+$.

Compound 1Rd (28 mg, 0.065 mmol), Compound 1b (21 mg, 0.085 mmol) and sodium. Carbonate (21 mg, 0.196 mmol) were dissolved in 1,4-dioxane/water (2 ml/0.4 ml), and then Pd(PPh$_3$)$_4$(8 mg, 0.007 mmol) was added. The reaction system was replaced with argon for 3 times, then the reaction mixture was heated in a microwave reactor to 100° C. and stirred for 30 minutes. The reaction liquid was cooled to room temperature, and then poured into water and extracted with ethyl acetate (10 ml×3). The combined organic layer was washed with brine, then dried over anhydrous sodium sulfate and filtered. The crude product obtained by concentrating the filtrate under reduced pressure was purified by preparative chromatography (methylene chloride/methanol=15/1 mixed solvent elution) to obtain pale yellow solid compound 1R (6 mg, yield 20%), $^1$H NMR (DMSO-$_6$, 400 MHz) δ 13.22 (s, 1 H), 9.44 (s, 1 H), 8.64 (s, 1 H), 8.14 (s, 1 H), 8.09 (s, 1 H), 7.98 (s, 1 H), 7.84 (d, 8.4 Hz, 11-1.), 7.74-7.67 (m, 2 H), 7.63 (s, 1 H), 7.57 (d, J=2.0 Hz, 1 H), 6.88 (d, J=8.8 Hz, 1 H), 4,27 (dd, J=10.4 Hz/=2.0 Hz, 1 H), 3.94 (dd, J=9.8 Hz, 9.8 Hz, 3.72 (d, J=11.2 Hz, 1 H), 3,03-2,97 (m, 2 H), 2.92 (d, J=10.4 Hz, 2.67-2.58 (m, 1 H), 2.43-2.32 (m, 2 H), 2.14-2.07 (m, 1 H), 1.70 (dd,=10.8 Hz, 10.4 Hz, 1 H), 1.05 (t, J=7.2 Hz, 3 H); MS m/z 467.2 [M+H]$^+$.

Example 2

Preparation of Compound 2R

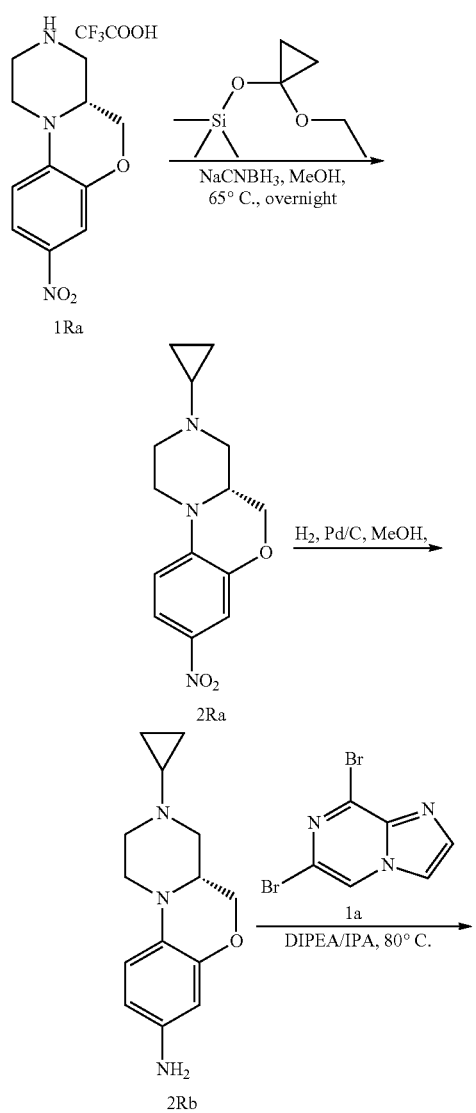

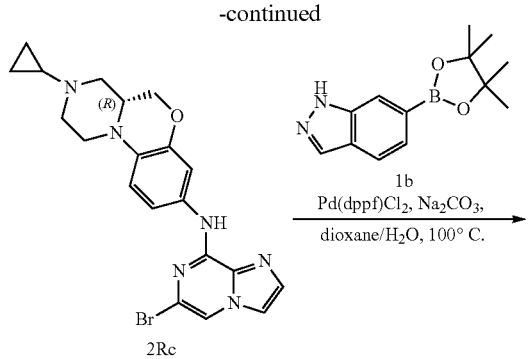

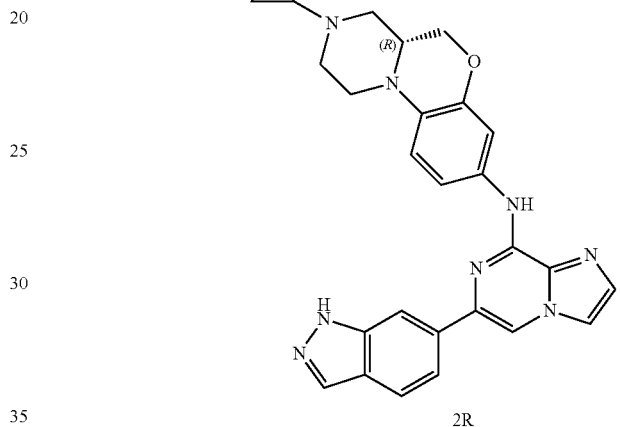

Trifluoroacetic acid salt of compound 1Ra (150 mg, 0.43 mmol) and 1-ethoxy-1-trimethylsiloxycyclopropane (234 mg, 1.34 mmol) were dissolved in methanol (6 ml), and sodium cyanoborohydride (84 mg, 1.34 mmol) was added under stirring. The reaction system was heated to 65° C. and stirred for 16 hours, TLC monitoring shown that the reaction was completed. The reaction system was cooled to room temperature, then poured into saturated sodium carbonate solution (10 ml), and extracted with ethyl acetate (15 ml×3). The combined organic layer was washed with brine (15 ml) and dried over anhydrous sodium sulfate and filtered. The crude product obtained by concentrating the filtrate under reduced pressure was separated by silica gel column (dichloromethane/methanol=60/1 solvent mixture elution) to obtain a yellow solid compound 2Ra (95 mg, yield 80%). $^1$1-4 NMR (CDCl$_3$, 400 MHz) δ 7.79 (dd, J=9.2 Hz, 2.4 Hz, 1 H), 7,65 (d, J=2.8 Hz, 1 H), 6,73 (d, I 9.2 Hz, 11-1), 4.26 (dd, J=10.8 Hz, 3.2 Hz, 1 H), 3.99 (dd,=10.8 Hz, 8.4 Hz, 1 H), 3.79-3.71(m, 1 H), 3.34-3.27 (m, 1 H), 3.15-3.08 (m, 1 H), 3.04-2.88(m, 2 H), 2.47-2.41 (m, 1 H), 2.09 (dd, J=10.4 Hz, 10.0 Hz, 1 H), 1,71-1.65 (m, 1 H), 0.55-0.42 (m, 4H); MS m/z 276.2 [M+H]$^+$.

Compound 2Ra (30 mg, 0.11 mmol) was placed in a 50 ml single-necked flask, dissolved in methanol (3 ml), and then Pd/C (10%, 10 mg) was added. The bottle was replaced with hydrogen, and the reaction was stirred at room temperature for 1 hour under a hydrogen atmosphere (one atmosphere). TLC monitoring showed that the reaction was completed, the reaction mixture was filtered, and the filtrate was spin dried to give a brown solid compound 2Rb (25 mg, yield 94%. The compound was used in the next step without purification.

Compound 2Rb (28 mg, 0.114 mmol), 6,8-dibromo-imidazole[1,2-α]pyrazine (Compound 1a, 34 mg, 0.123 mmol) and N,N-diisopropylethylamine (29 mg, 0.225 mmol) were dissolved in isopropanol (1 ml). The reaction system was heated to 80° C. in a sealing tube and stirred for 16 hours. The reaction liquid was cooled to room temperature, and then poured into water (10 ml) and extracted with ethyl acetate (10 ml×3). The combined organic layer was washed with saturated brine (10 ml), then dried over anhydrous sodium sulfate and filtered. The crude product obtained by concentrating the filtrate under reduced pressure was purified by preparative chromatography (methylene chloride/methanol=50/1 mixed solvent elution) to obtain pale gray solid compound 2Rc (40 mg, yield 79%). MS m/z 441.0 1M+H1 443.0 [M+H]$^+$.

Compound 2Rc (40 mg, 0.091 mmol), Compound 1b (32 mg, 0.131 mmol) and sodium carbonate (24 mg, 0.226 mmol) were dissolved in 1,4-dioxane/water (1 ml/0.2 ml), and then Pd(PPh$_2$)$_2$ (5 mg, 0.007 mmol) was added. The reaction system was replaced with argon for 3 times, then the reaction system was heated in a microwave reactor to 100° C. and stirred for 2 hours. The reaction liquid was cooled to room temperature, and then poured into water (10 ml) and extracted with ethyl acetate (10 ml×3). The combined organic layer was washed with brine (10 ml), then dried over anhydrous sodium sulfate and filtered. The crude product obtained by concentrating the filtrate under reduced pressure was purified by preparative chromatography (methylene chloride/methanol=20/1 mixed solvent elution) to obtain yellow solid compound 2R (17 mg, yield 39%). $^1$H NMR (DMSO-d$_6$, 400 MHz) δ 13.22 (s, 1 H), 9.45 (s, 1 H), 8.83 (s, 1 H), 8.13 (s, 1 H), 8.10-8.08 (m, 1 H), 7.98 (d, J=0.8 Hz, 1 H), 7.87-7.82 (m, 1 H), 7.73-7.67 (m, 2 H), 7.63 (d,=0.8 Hz, 1 H), 7.57 (d, J=2.4 Hz, 1 H), 688 (d/=8.8 Hz, 1 H), 4.30-4.24 (m, 1 H), 3.95 (dd, J=10.4 Hz, 9.2 Hz, 1 H), 3.75-3.67 (m, 1 H), 3.06-2.90 (m, 3 H), 2.59-2.37 (m, 2 H), 2.04-1.98 (m, 1 H), 1.71-1.63 (m, 1 H), 0.49-0.43 (m, 2 H), 0.40-0.35 (m, 2 H); MS 479.2 [M+H]$^+$.

Example 3

Preparation of Compound 3R

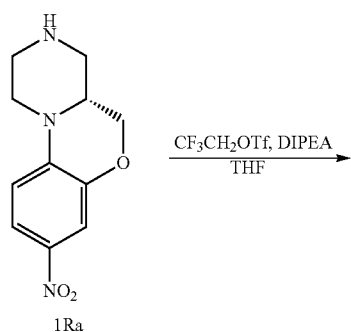

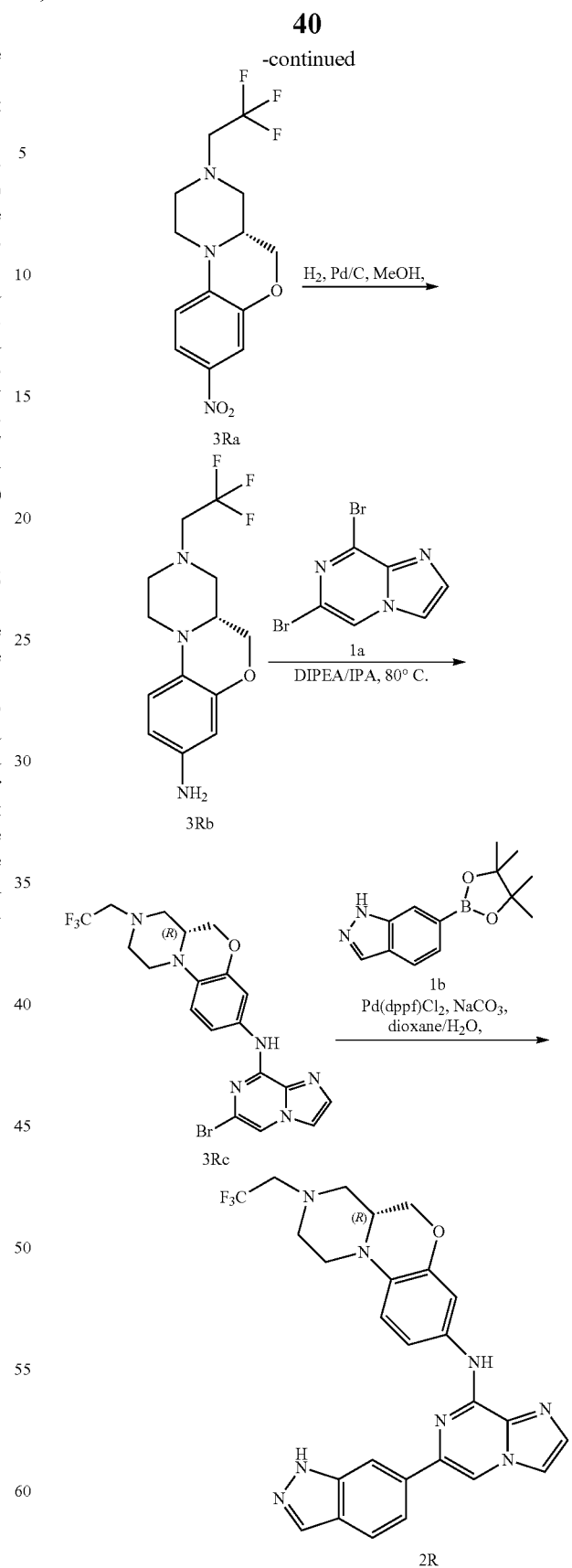

Compound 1Ra (430 mg, 1.83 mmol) and N,N-diisopropylethylamine (706 mg, 5.46 mmol) were dissolved in dry tetrahydrofuran (8 ml), and 2,2,2-trifluoroethyl trifluoromethanesulfonate (551 mg, 2.37 mmol) was added under stirring. The reaction system was heated to 60° C. and stirred for 16 hours, TLC monitoring shown that the reaction was completed. The reaction system was poured into water, and extracted with ethyl acetate (15 ml×3). The combined organic layer was washed with saturated brine (15 ml) and dried over anhydrous sodium sulfate and filtered. The crude product obtained by concentrating the filtrate under reduced pressure was separated by silica gel column (dichloromethane/methanol=3/1 solvent mixture elution) to obtain a yellow solid compound 3Ra (550 mg, yield 95%). $^1$H NMR (CDCl$_3$, 400 MHz) δ 7.80 (dd, J=9.2 Hz, 2.8 Hz, 1 H), 7,66 (d/=2.8 Hz, 1 H), 6.75 (d, J=9.2 Hz, 1 H), 4.25 (dd, J=10.8 Hz, 2.8 Hz, 1 H), 3.99 (dd, J=11.2 Hz, 8.4 Hz, 1 H), 3.81-3.75 (m, H), 3.48-3.41 (m, 1 H), 3.10-2.95 (m, 5 H), 2.70-2.63 (m, 1 H), 2.31 (dd, J=10.8 Hz, 10.8Hz, 1 H); MS m/z 318.2 [M+H]$^+$.

Compound 3Ra (300 mg, 0.95 mmol) was placed in a 50 ml single-necked flask, dissolved in methanol (15 ml), and then Pd/C (10%, 50 mg) was added. The bottle was replaced with hydrogen, and the reaction was stirred at room temperature for 1 hour under a hydrogen atmosphere (one atmosphere). TLC monitoring showed that the reaction was completed, the reaction mixture was filtered, and the filtrate was concentrated under reduced pressure to give a brown solid compound 3Rb (250 mg, yield 92%).

Compound 3Rb (35 mg, 0.122 mmol), 6,8-dibromoimidazole[1,2-α]pyrazine (Compound 1a, 41 mg, 0.148 mmol) and N,N-diisopropylethylamine (31 mg, 0.240 mmol) were dissolved in isopropanol (1 ml). The reaction system was heated to 80° C. in a sealing tube and stirred for 16 hours. The reaction liquid was cooled to room temperature, and then poured into water and extracted with ethyl acetate (10 ml×3). The combined organic layer was washed with brine (10 ml), then dried over anhydrous sodium sulfate and filtered. The crude product obtained by concentrating the filtrate under reduced pressure was purified by preparative chromatography (methylene chloride/methanol=70/1 mixed solvent elution) to obtain gray solid compound 3Rc (45 mg, yield 76%). MS m/z 483.0 [M+H]$^+$, 485.0 [M+H]$^+$.

Compound 3Rc (45 mg, 0.093 mmol), 1b (34 mg, 0.139 mmol) and sodium carbonate (24 mg, 0.236 mmol) were dissolved in 1,4-dioxane/water (1 ml/0.2 ml), and then Pd(PPh$_2$)$_2$ (5 mg, 0.007 mmol) was added. The reaction system was replaced with argon for 3 times, then the reaction system was heated in a sealing tube to 100° C. and stirred for 16 hours. The reaction liquid was cooled to room temperature, and then poured into water (10 ml) and extracted with ethyl acetate (10 ml×3). The combined organic layer was washed with saturated brine (10 ml), then dried over anhydrous sodium sulfate and filtered. The crude product obtained by concentrating the filtrate under reduced pressure was purified by preparative chromatography (methylene chloride/methanol=15/1 mixed solvent elution) to obtain yellow solid compound 3R (25 mg, yield 52%). $^1$H NMR (DMSO-1$_6$, 400 MHz) δ 13.22 (s, 1 H), 9.47 (s, 1 H), 8.64 (s, 1 H), 8.13 (s, 1 H), 8.09 (s, 1 H), 7.98 (s, 1 H), 7.87-7.82 (m, 1 H), 7.73-7.67 (m, 2 H), 7.63 (d, J=0.8 Hz, 1 H), 7.59 (d, J=2.4 Hz, 1 H), 6.90 (d, J=8.8 Hz, 1 H), 4.30-4.22 (m, 1 H), 3.97-3.89 (m, 1 H), 3.77-3.70 (m, 1 H), 3.33-3.24 (m, 2 H), 3.08-2.94 (m, 3 H), 2.70-2.56 (m, 2 H), 2.24-2.18 (m, 1 H); MS m/z 521.2 [M+H]$^+$.

Example 4

Preparation of Compound 4R

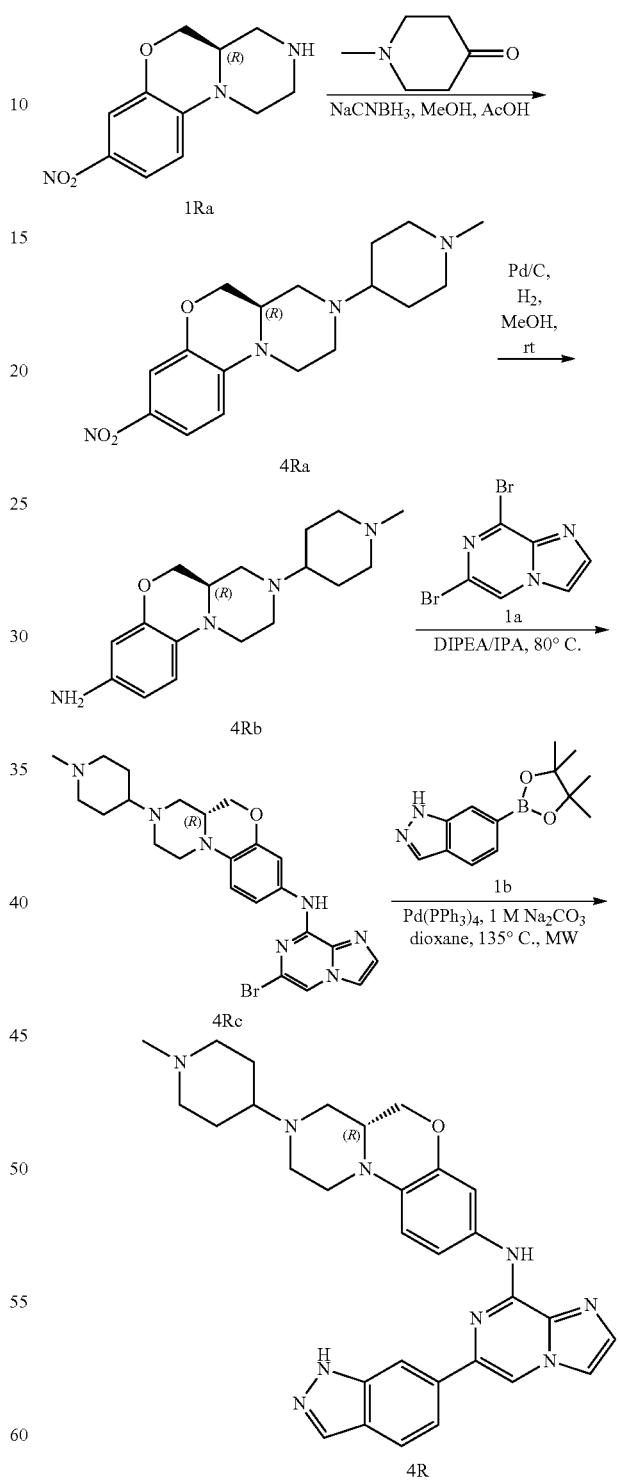

Compound 1Ra (970 mg, 4.12 mmol) and N-methyl-4-piperidone (933 mg, 8.24 mmol were dissolved in methanol (35 ml), and acetic acid (247 mg, 4.12 mmol) was added under stirring, and then sodium cyanoborohydride (776 mg, 12.35 mmol) was added in batches. The temperature was controlled below 10° C. The reaction system was stirred at room temperature for 16 hour, TLC monitoring showed that the reaction was completed, then the solvent was removed under reduced pressure at room temperature. The residue was dispersed in a saturated sodium carbonate solution and extracted with ethyl acetate (25 ml×3). The combined organic layer was washed with saturated brine (20 ml) and dried over anhydrous sodium sulfate. The residue obtained by concentrating the filtrate under reduced pressure was separated by silica gel column (dichloromethane/methanol=20/1 solvent mixture elution) to obtain yellow solid compound 4Ra (860 mg, yield 63%). MS m/z 333.2 [M+H]+.

Compound 4Ra (373 mg, 1.12 mmol) was placed in a 50 ml single-necked flask, dissolved in methanol (7 ml), and then Pd/C (10%, 40 mg) was added. The bottle was replaced with hydrogen, and the reaction was stirred at room temperature for 2 hours under a hydrogen atmosphere. TLC monitoring showed that the reaction was completed, then the reaction solution was filtered, and the filtrate was concentrated under reduced pressure to give crude product, which was separated by silica gel column (dichloromethane/methanol/aqueous ammonia=10/1/0.25 mixed solvent elution) to provide brown solid compound 4Rb (150 mg, yield 44%). MS m/z 303.3 [M+H]+.

Compound 4Rb (34 mg, 0.113 mmol) was suspended in isopropanol (2 ml), and DIPEA (9 mg, 0.225 mmol) and 6,8-dibromo-imidazole [1,2-α] pyrazine (31 mg, 0.113 mmol) was added, then the reaction mixture was heated to 80 °C to react for 4 hours. The reaction mixture was cooled to room temperature. The residue obtained by concentration under reduced pressure was purified by preparative thin chromatographe (dichloromethane/methanol=15/1 mixed solvent elution) to obtain brown solid compound 4Rc (28 mg, 50% yield). MS m/z 498.0 [M+H]+, 500.0 [M+H]+.

Compound 4Rc (28 mg, 0.056 mmol), compound 1b (27 mg, 0.112 mmol) and sodium carbonate (18 mg, 0.169 mmol) were dissolved in 1,4-dioxane/water (1 ml/0.2 ml), and then Pd(PPh$_3$)$_4$ was added (6 mg, 0.006 mmol). The reaction system was replaced with argon for 3 times, then the reaction mixture was heated in a microwave reactor to 135° C. and stirred for 1 hour. The reaction liquid was cooled to room temperature, and then poured into water (10 ml) and extracted with ethyl acetate (10 ml×3). The combined organic layer was washed with saturated brine (10 ml), then dried over anhydrous sodium sulfate and filtered. The crude product obtained by concentrating the filtrate under reduced pressure was purified by preparative chromatography (methylene chloride/methanol=5/1 mixed solvent elution) to obtain pale yellow solid compound 4R (7 mg, yield 23%). $^1$H NMR (DMSO-d$_6$, 400 MHz) δ 13.22 (s, 1 H), 9.44 (s, 1 H), 8.64 (s, 1 H), 8.13 (s, 1 H), 8.09 (s, 1 H), 7.98 (d, J=0.8 Hz, 1 H), 7.84 (d, J=8.4 Hz, 1 H), 7.73-7.67 (m, 2 H), 7,63 (d, J=0.8 Hz, 1 H), 7,57 (d, J=2.0 Hz, 1 H), 6.87 (d, J=8.8 Hz, 1 H), 4.26 (dd, J=10.4 Hz, J=2.4 Hz, 1 H), 3.94 (dd, J=10.4Hz, 9.2 Hz, 1 H), 3.72 (d, J=11.6 Hz, 1 H), 3.04-2.90 (m, 3 H), 2.86-2.78 (m, 2 H), 2.63-2.55 (m, 1 H), 2.38-2.28 (m, 214), 2.23-2.11 (m, 4 H), 1.95-1.85 (m, 2 H), 1.80-1.71 (m, 2 H), 1.49-1.38 (m, 2 H); MS m/z 536.4 1[M+H]+.

Example 5

Preparation of Compound 5R

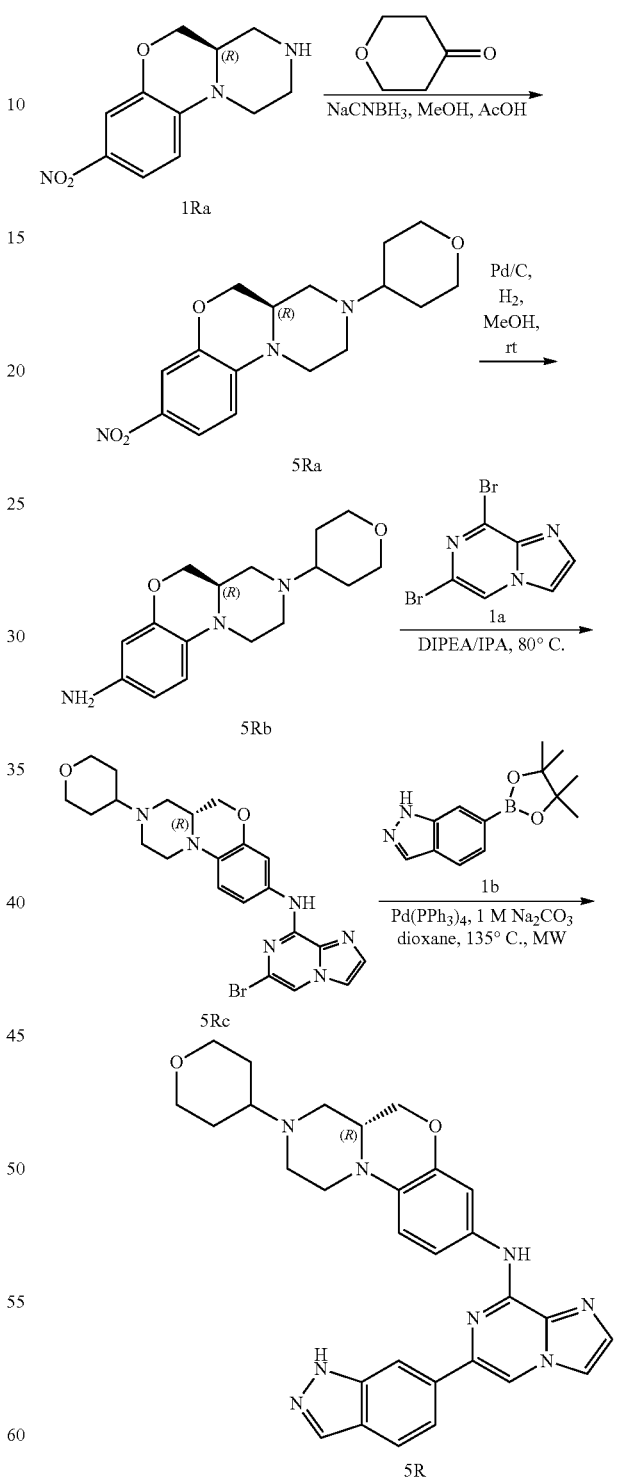

Compound 1Ra (600 mg, 2.55 mmol) and tetrahydropyrone (511 mg, 5.10 mmol) were dissolved in methanol (25 ml), and acetic acid (153 mg, 2.55 mmol) was added under stirring, and then sodium cyanoborohydride (481 mg, 7.65 mmol) was added in batches. The temperature was controlled below 10° C. The reaction system was stirred at room temperature overnight, TLC monitoring showed that the reaction was completed, then the solvent was removed under reduced pressure at room temperature. The residue was dispersed in a saturated sodium carbonate solution and extracted with ethyl acetate (20 ml×3). The combined organic layer was washed with saturated brine (20 ml) and dried over anhydrous sodium sulfate. The residue obtained by concentrating the filtrate was separated by silica gel column (dichloromethane/methanol=30/1 solvent mixture elution) to obtain yellow solid compound 5Ra (800 mg, yield 98%). MS m/z 320.2 [M+H]$^+$.

Compound 4Ra (200 mg, 0.63 mmol) was placed in 50 ml single-necked flask, dissolved in methanol (5 ml), and then Pd/C (10%, 30 mg) was added. The bottle was replaced with hydrogen, and the reaction was stirred at room temperature for 1 hour under a hydrogen atmosphere. TLC monitoring showed that the reaction was completed, then the reaction solution was filtered, and the filtrate was concentrated under reduced pressure to give crude product, which was separated by silica gel column (dichloromethane/methanol=30/1 mixed solvent elution) to provide brown solid compound 5Rb (80 mg, yield 44%). MS m/z 290.2 [M+H]$^+$.

Compound 5Rb (30 mg, 0.104 mmol) was suspended in isopropanol (2 ml), and DIPEA (27 mg, 0.208 mmol) and 6,8-dibromo-imidazole pyrazine (29 mg, 0.104 mmol) was added, then the reaction mixture was heated to 80° C. to react for 16 hours. The reaction mixture was cooled to room temperature. The residue obtained by concentration under reduced pressure was purified by preparative thin chromatography (dichloromethane/methanol=15/1 mixed solvent elution) to obtain pale yellow solid compound 5Rc (43 mg, 86% yield). MS m/z 485.1 [M+H]$^+$, 487.1 [M+H]$^+$.

Compound 5Rc (43 mg, 0.089 mmol), compound 1b (43 mg, 0.178 mmol) and sodium carbonate (28 mg, 0.267 mmol) were dissolved in 1,4-dioxane/water (1 ml/0.2 ml), and then Pd(PPh$_s$)$_4$ was added (10 mg, 0.009 mmol). The reaction system was replaced with argon for 3 times, then the reaction mixture was heated in a microwave reactor to 135° C. and stirred for 1 hour. The reaction liquid was cooled to room temperature, and then poured into water (10 ml) and extracted with ethyl acetate (10 ml×3). The combined organic layer was washed with saturated brine (10 ml), then dried over anhydrous sodium sulfate and filtered. The residue obtained by concentrating the filtrate under reduced pressure was purified by preparative chromatography (methylene chloride/methanol=15/1 mixed solvent elution) to obtain pale yellow solid compound 5R (21 mg, yield 45%). $^1$H NMR (DMSO-d$_6$, 400 MHz) δ 13.22 (s, 9.45 (s, 8.64 (s, 1 H), 8.14 (s, 1 H), 8.09 (s, 1 H), 7.98 (d,=0.8 Hz, 1 H), 7.84 (d, J=8.4 Hz, 1 H), 7.73-7.66 (m, 2 H), 7.63 (d, J=0.8 Hz, 1 H), 7.57 (d,=2.4 Hz, 1 H), 6.88 (d, J=9.2 Hz, 1 H), 4.27 (dd, J=10.4 Hz, 2.0 Hz, 1 H), 3.98-3.87 (m, 3 H), 3.73 (d, J=11.2 Hz, 1 H), 3.30-3.24 (m, 2 H), 3.06-2.91 (m, 3 H), 2.63-2.55 (m, 1 H), 2.47-2.39 (m, 1 H), 2.36-2.28 (m, 1 H), 1.90 (dd, J=11.2 Hz, 11.2 Hz, 1 H), 1.77-1.72 (m, 2 H), 1.49-1.37 (m, 2 H); MS m/z 523.2 [M+H]$^+$.

Example 6

Preparation of Compound 6

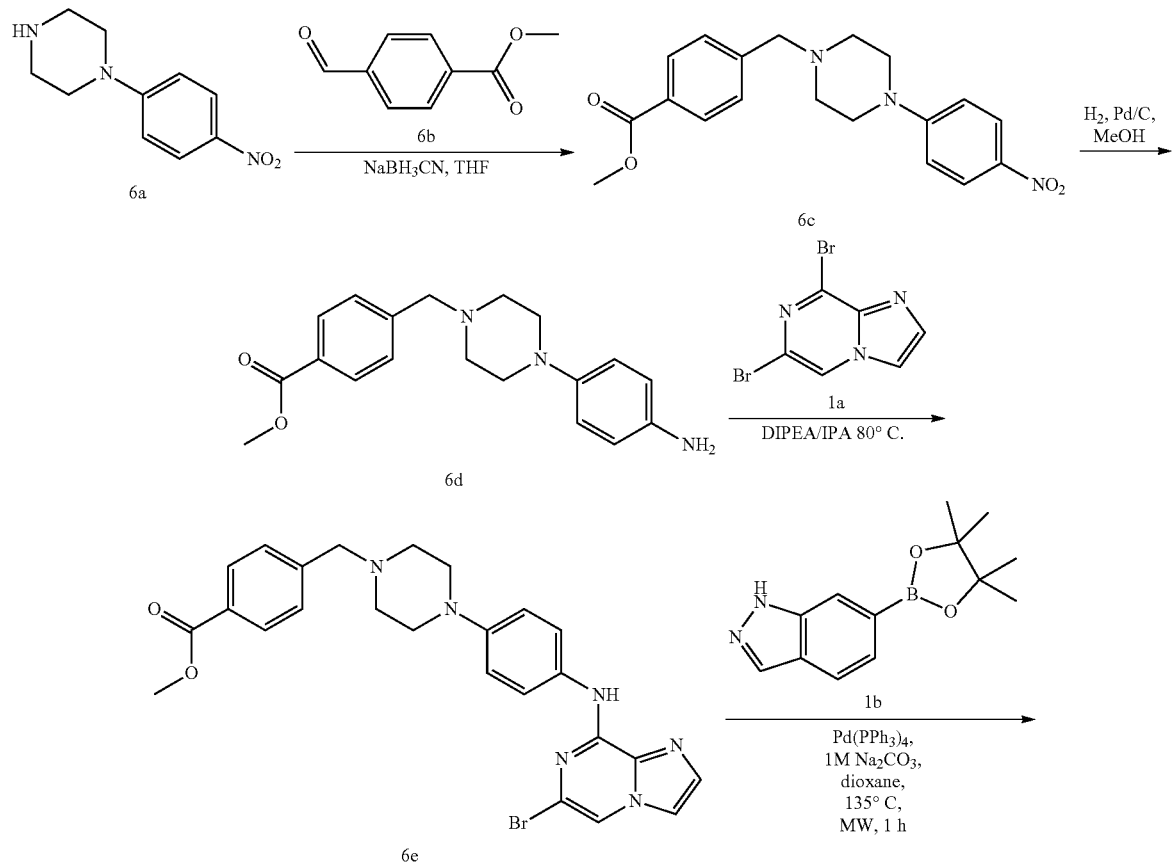

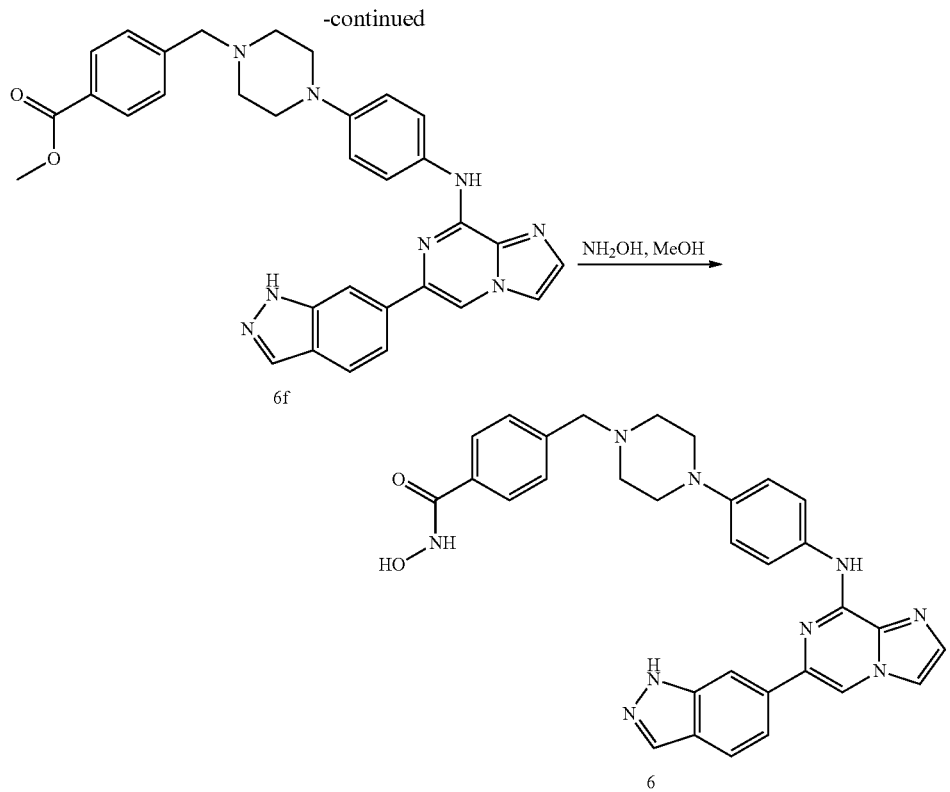

Compound 6a (300 mg, 1.45 rumor) and 6b (356 mg, 2.17 mmol) were dissolved in tetrahydrofuran (10 ml). The reaction was stirred at room temperature 4 hours, then NaBH$_3$CN (273 mg, 4.34 mmol) was added to the reaction system in batches. The reaction system was stirred at room temperature in sealed state for 16 hours. LCMS monitored that the reaction was completed, then the reaction mixture was poured into water (30 ml), and extracted with ethyl acetate (15 ml×3), and then washed with saturated brine (10 ml×2). The ethyle acetate layer was dried over anhydrous sodium sulfate and filtered, and the residue obtained by concentrating the filtrate under reduced pressure was purified by column chromatography (petroleum ether/ethyl acetate=10/1 to 4/1) to give a yellow solid compound 6c (170 mg, yield 33%). $^1$H NMR (CDCl$_3$, 400 MHz) δ 8.14-8.10 (m, 1 H), 8.03-8.00 (m, 1 H), 7.45-7.42 (m, 2 H), 6.81 (dd, J=7.2 Hz, 2.0 Hz, 2 H), 3.92. (s, 3 H), 3.62 (s, 2 H), 343 (t, J=5.2 Hz, 4 H), 2.60 (t, J=5.2 Hz, 4H); MS m/z 356.3 [M+H]$^+$.

Compound 6c (150 mg, 0.42 mmol) was dissolved in methanol (5 ml), then Pd/C (10%, 50 mg) was carefully added to the reaction system, and then replaced with hydrogen for three times. The reaction solution was stirred under room temperature to react for 16 hours. After LCMS detected that the reaction was completed, the mixture was filtered through celite, washed with anhydrous methanol, and the filtrate was concentrated under reduced pressure to provide pale yellow solid compound 6d (100 mg, yield 73%). MS m/z 326.3 [M+H]$^+$.

Compound 1a (170 mg, 0.62 mmol), 6d (100 mg, 0.31 mmol) and D PEA (80 mg, 0.62 mmol) were added to isopropanol (4 ml). The reaction system was heated to 80° C. and stirred to react in a sealed system for 16 hours. LCMS monitored that the reaction was completed, then the reaction mixture was poured into water (10 ml), and extracted with ethyl acetate (10 ml×3), and then washed with saturated brine (5 ml×2). The ethyl acetate layer was dried over anhydrous sodium sulfate and filtered., and the residue obtained by concentrating the filtrate under reduced pressure was purified by column chromatography (petroleum ether/ethyl acetate=10/1 to 2/1 solvent mixture) to give a brown solid compound 6e (150 mg, yield 47%), $^1$H NMR (CDCl$_3$, 400 MHz) δ 8.03-7.99 (m, 3 H), 7.71 (d, J=8.8 Hz, 2 H), 7.67 (s, 1 H), 7.53 (d, J=0.8 Hz, 1 H), 7.49 (d, J=0.8 Hz, 1 H), 7.45 (d, J=8.0 Hz, 2 H), 6.97 (d, J=9.2 Hz, 2 H), 3.92 (s, 3H), 3.62 (s, 2 H), 3.21-3.17 (m, 4 H), 2.65-2.61 (m, 4H); MS m/z 521.2 [M+H]$^+$; 523.2 [M+H]$^+$.

Compound 6e (140 mg, 0.27 mmol), 1b (132 mg, 0.54 mmol), Pd(PPh$_3$)$_4$ (31 mg, 0.027 mmol) and Na$_2$CO$_3$ (67 mg, 0.54 mmol) were added into dioxane/water (4 ml/0.4 ml). The reaction solution was heated by microwave condition to 135° C. and stirred to react for 1 hours. LCMS monitored that the reaction was completed, then the reaction mixture was poured into water (10 ml), and extracted with ethyl acetate (10 ml×3), and then washed with saturated brine (5 ml ×2). The ethyl acetate layer was dried over anhydrous sodium sulfate and filtered, and the residue obtained by concentrating the filtrate under reduced pressure was purified by preparative thin layer chromatography (petroleum ether/ethyl acetate=1/1 solvent mixture) to give a brown solid compound 6f (80 mg, yield 53%). MS m/z 559.3 [M+H]$^+$.

Compound 6f (35 mg, 0.063 mmol) was added to methanol (0.5 mL), and then aqueous hydroxylamine solution (2 ml) was added into the reaction solution. The reaction solution was heated to 30° C. and stirred to react for 4 hours. LCMS monitored that the reaction was completed, then the reaction mixture was poured into water (5 ml), and extracted with ethyl acetate (5 ml×3), and then washed with saturated brine (2 ml×2). The ethyl acetate layer was dried over anhydrous sodium sulfate and filtered, and the residue obtained by concentrating the filtrate under reduced pressure was purified by preparative thin layer chromatography (CH$_2$Cl$_2$/MeOH=10/1 solvent mixture) to give a gray solid compound 6 (10 mg, yield 28%). $^1$H NMR (DMSO-6, 400 MHz) δ 13.19 (s, 1 H), 11.19 (s, 1+1), 9.52 (s, 1 H), 9.02 (s, 1 H), 8.67 (s, 1 H), 8.18 (s, 1 H), 8.09 (s, 1 H), 8.02-7.98 (m, 3 H), 7.83 (d, J=8.8 Hz, 1 H), 7.75-7.70 (m, 3 H), 7.64 (s, 1 H), 7.43 (d, J=8.0 Hz, 2 H), 6.99 (d, J=9.2 Hz, 2 H), 3.59 (s, 2 H), 3.18-3.11 (m, 4 H), 2.58-2.50 (m, 4 H); MS m/z 560.3 [M+H]$^+$.

Example 7

Preparation of Compound 7

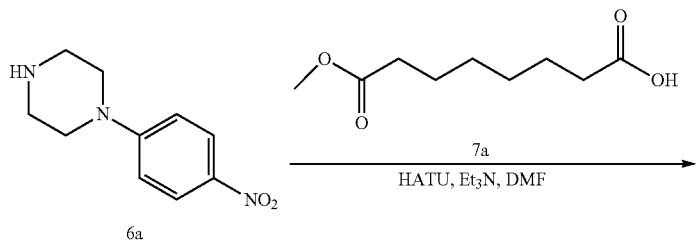

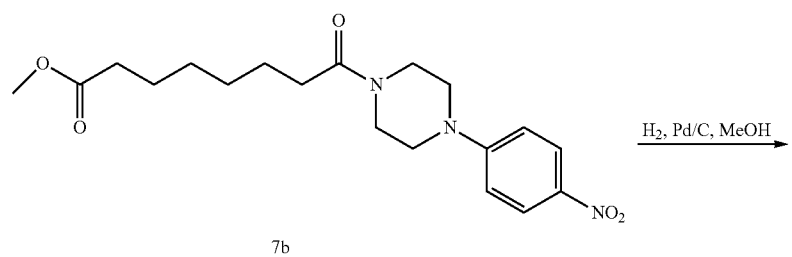

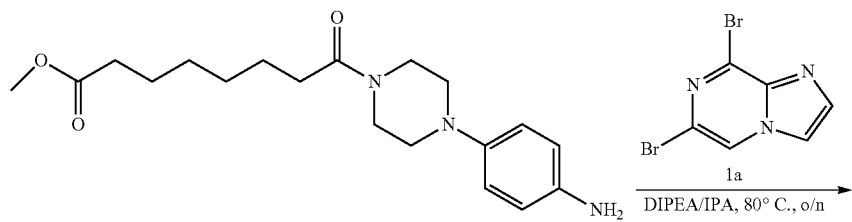

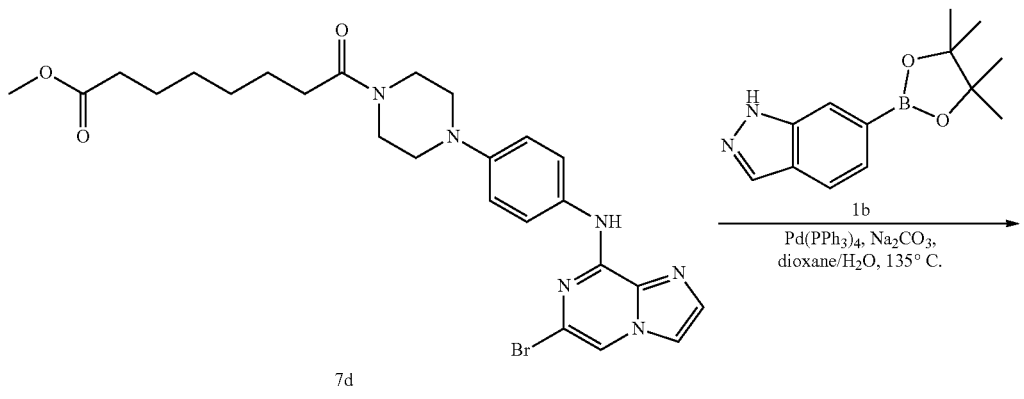

-continued
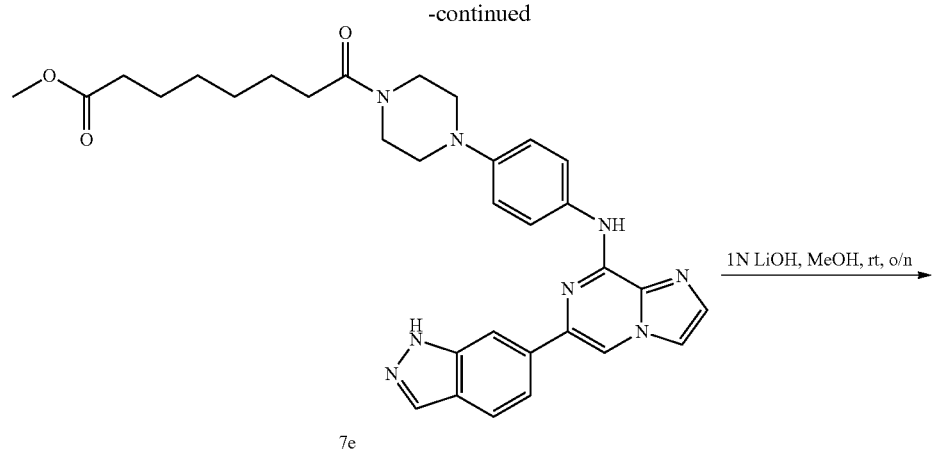
7e
1N LiOH, MeOH, rt, o/n →
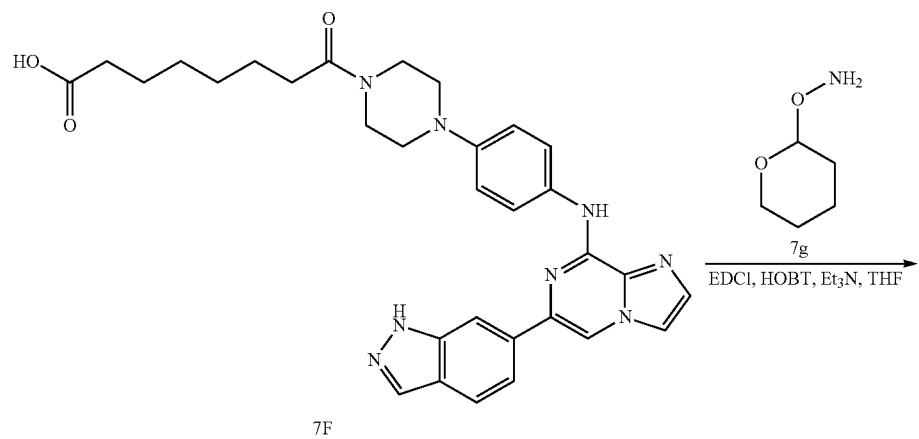
7F
7g
EDCl, HOBT, Et₃N, THF →
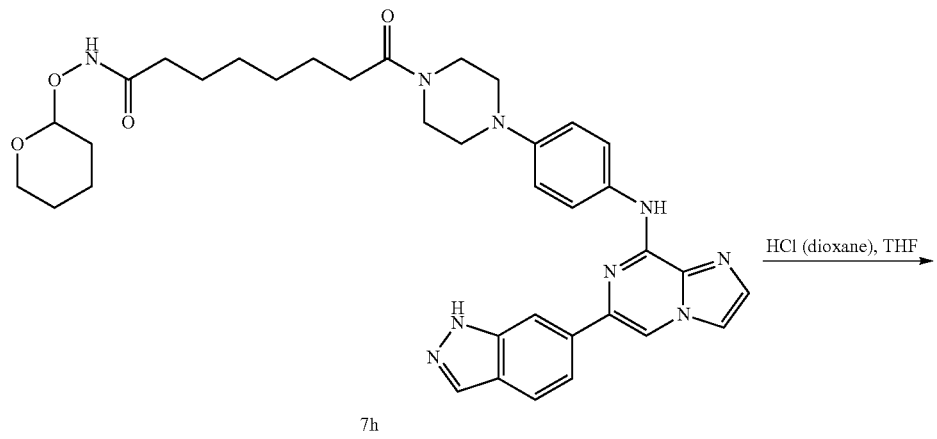
7h
HCl (dioxane), THF →

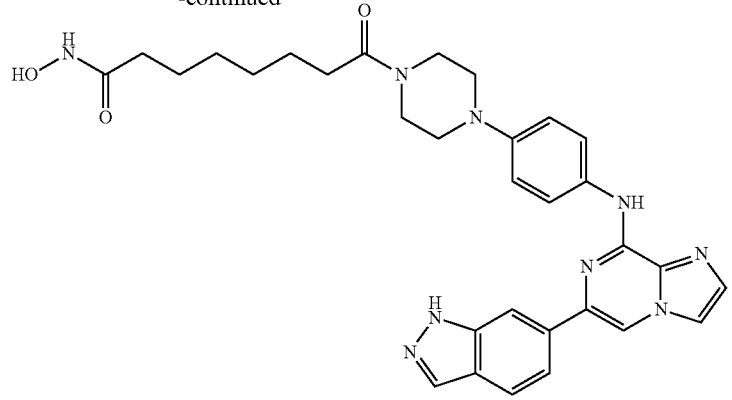

7

Compound 6a (250 mg, 1.20 mmol), 7a (339 mg, 1.80 mmol), HATU (913 mg, 2.40 mmol) and triethylamine (364 mg, 3.60 mmol) were added to N,N-dimethylformamide (10 ml), and the reaction mixture was stirred at room temperature for 4 hours. LCMS monitored that the reaction was completed, then the reaction mixture was poured into water (30 ml), and extracted with ethyl acetate (15 ml×4), and then washed with saturated brine (20 ml). The organic phase was dried with anhydrous sodium sulfate and filtered. The filtrate was concentrated under reduced pressure to afford yellow liquid compound 7b (350 mg, yield 77%), MS m/z 378.2 [M+H]$^+$.

Compound 7b (340 mg, 0.90 mmol) was dissolved in methanol (10 ml), then Pd/C (100 mg) was carefully added to the reaction system, and then replaced with hydrogen for three times. The reaction solution was stirred under room temperature to react for 2 hours. After LCMS detected that the reaction was completed, the filter cake was filtered through celite, washed with anhydrous methanol, and the organic layer was concentrated under reduced pressure to provide pale yellow solid compound 7c (250 mg, yield 80%). MS m/z 348.3 [M+H]$^+$.

Compound 1a (200 mg, 0.72 mmol), 7c (201 mg, 0.59 mmol) and DIPEA (153 mg, 1.18 mmol) were added to isopropanol (8 ml). The reaction mixture was heated to 80° C. in sealed tube and stirred to react overnight. LCMS monitored that the reaction was completed, then the reaction mixture was poured into water (20 ml), and extracted with ethyl acetate (15 ml×3), and then washed with saturated brine (10 ml×2). The organic layer was dried over anhydrous sodium sulfate and filtered, and the residue obtained by concentrating the filtrate under reduced pressure was purified by column chromatography (petroleum ether/ethyl acetate=10/1 to 3/1 solvent mixture) to give a brown liquid compound 7d (200 mg, yield 51%). $^1$H NMR (CDCl$_3$, 400 MHz) δ 8.03 (s, 1 H), 7.74 (d, J=9.2 Hz, 2 H), 7.69 (s, 1 H), 7.54 (d, J=0.8 Hz, 1 H), 7.50 (d, J=1.2 Hz, 1 H), 6.97 (d,=9.2 Hz, 2 H), 3.81-3.76 (m, 214), 3.67 (s, 3 H), 3.66-3.60 (m, 2 H), 3.19-3.10 (m, 4H), 2.37 (t, J=8.0 Hz, 2 H), 2.32 (t, J=7.6 Hz, 2 H), 1.69-1.60 (m, 2 H), 1.50-1.42 (m, 4 H), 1.40-1.32 (m, 2 H); MS m/z 543.3 [M+H]$^+$, 545.3 [M+H]$^+$.

Compound 7d (200 mg, 0.37 mmol), 1b (180 mg, 0.74), Pd(PPh$_3$)$_4$ (43 mg, 0.037 mmol) and sodium carbonate (78 mg, 0.74 mmol) were added to dioxane/water (8 ml/1 ml). The reaction mixture was heated by microwave condition to 135° C. and stirred to react for 1 hour. LCMS monitored that the reaction was completed, then the reaction mixture was poured into water (15 ml), and extracted with ethyl acetate (10 ml×3), and then washed with saturated brine (10 ml×2). The organic layer was dried over anhydrous sodium sulfate and filtered, and the residue obtained by concentrating the filtrate under reduced pressure was purified by preparative thin layer chromatography (petroleum ether/ethyl acetate=1/1 solvent mixture) to give gray liquid compound 7e (75 mg, yield 35%). MS m/z 581.2 [M+H]$^+$.

Compound 7e (50 mg, 0.086 mmol) was dissolved in methanol (2 ml), and aqueous lithium hydroxide solution (1 N, 1 ml) was added dropwise, and the reaction mixture was stirred at room temperature to react for 16 hrs. LCMS monitored that the reaction was completed, then the reaction mixture was poured into water (4 ml), and extracted with ethyl acetate (5 ml×6), and then washed with saturated brine (3 ml×2). The organic phase was dried over anhydrous sodium sulfate and filtered. The filtrate was concentrated under reduced pressure to afford brown solid compound 7f (50 mg). The compound was used in the next step reaction without further purification. MS m/z 567.4 [M+H]$^+$.

Compound 7f (50 mg, 0.086 mmol), 7g (21 mg, 0.18 mmol), EDCI (34 mg, 0.18 mmol), HOBT(24 mg, 0.18 mmol) and triethylamine (18 mg, 0.18 mmol) were added to tetrahydrofuran (3 ml). The reaction mixture was stirred at room temperature to react for 2 days. LCMS monitored that the reaction was completed, then the reaction mixture was poured into water (6 ml), and extracted with ethyl acetate (5 ml×5), and then washed with saturated brine (10 ml×2). The organic layer was dried over anhydrous sodium sulfate and filtered, and the residue obtained by concentrating the filtrate under reduced pressure was purified by preparative thin layer chromatography (petroleum ether/ethyl acetate=2/1 solvent mixture) to give a brown solid compound 7h (45 mg, yield of two steps was 69%), $^1$H NMR (DMSO-6, 400 MHz) δ 13.19 (s, 1 H), 10.90 (s, 1 H), 9.56 (s, 1 H), 8.67 (s, 1 H), 8.19 (s, 1 H), 8.09 (s, 1 H), 8.04 (d, J=8.8 Hz, 2 H), 7.99 (d, J=1.2 Hz, 1 H), 7.84 (d, J=8.8 Hz, 1 H), 7.72 (dd/=8.8 Hz, 0.8 Hz, 1 H), 7.64 (d, J=0.8 Hz, 1 H), 7.02 (d/=9.2 Hz, 2 H), 4.82-4.78 (s, 1 H), 3.94-3.87 (m, 1 H), 3.65-3.59 (m, 4 H), 3.51-3.45 (m, 1 H), 3.18-3.05(m, 4 H), 2.35 (t, J=7.4 Hz, 2 H), 1.98 (t, 7.4 Hz, 2 H), 1.70-1.58 (m, 3 H), 1.57-1.43 (m, 7 H), 1.31-1.20 (m, 4 H).

The compound 7h (40 mg, 0.06 mmol) was dissolved in tetrahydrofuran (1 ml), and then 4 N HCl dioxane solution (1 ml) was slowly added dropwise at room temperature. The reaction mixture was stirred under room temperature to react for 2 hours. LCMS monitored that the reaction was completed, then the reaction mixture was concentrated under reduced pressure. The crude product was pulped and washed with acetonitrile and diethyl ether. The product was dissolved in DMSO and added to deionized water, and lyophilized to give a brown solid compound 7 (25.6 mg, yield 73%). $^1$H NMR (DMSO-d$_6$, 400 MHz) δ 10.61 (br s, 1 H), 10.37 (br s, 1 H), 8.88 (s, 1 H), 8.27-8.20 (m, 3 H), 8.19-8.09 (m, 4 H), 7,91 (d, J=8.4 Hz, 7.75 (d, J=8.4 Hz, 1 H), 7.43-7.30 (m, 2 H), 5.20-6.20 (br, 1 H), 3.82-3.70 (m, 4 H), 3.36-3.22 (m, 4 H), 2.37 (t, J=7.6 Hz, 2 H), 1.95 (t, J=7.2 Hz, 2 H), 1.56-1.43 (m, 4H), 1.34-1.20 (m, 4 H); MS m/z 582.2 [M+H]$^+$.

Example 8

Preparation of Compound 8R

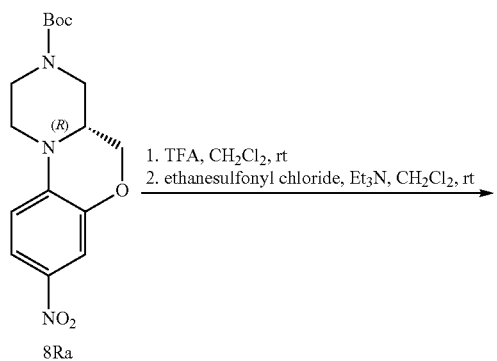

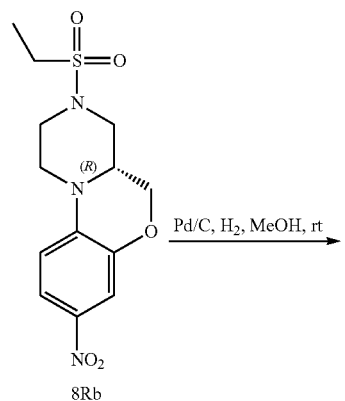

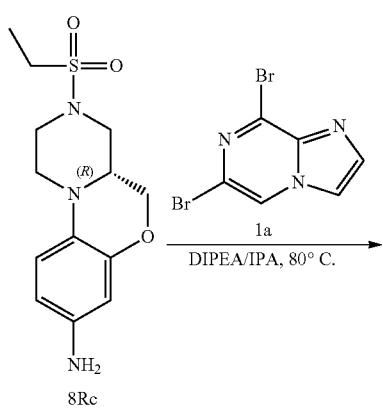

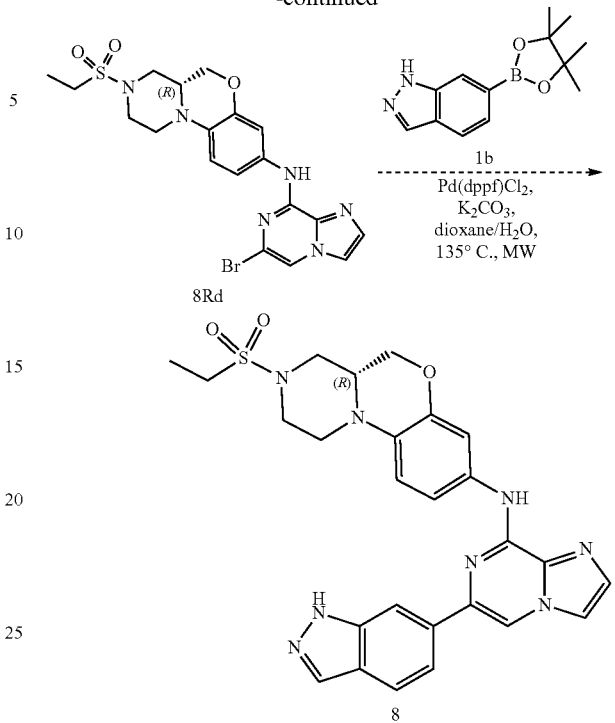

Compound 8Ra (200 mg, 0.60 mmol) was dissolved in dichloromethane (10 ml), and trifluoroacetic acid was added to the reaction system (1.5 ml) and stirred at room temperature for 2 hours. Under 40° C., the mixture was concentrated under reduced pressure to remove trifluoroacetic acid. The residue obtained was dissolved in dichloromethane (10 ml), and ethyl sulfonyl chloride (116 mg 0.90 mmol) and triethylamine (121 mg, 1.20 mmol) was added thereto, and stirred at room temperature for 16 hours. The reaction mixture was washed with water (10 ml×2), then the organic phase was dried over anhydrous magnesium sulfate, filtered, and the filtrate is concentrated under reduced pressure to obtain the filtrate, which was purified by normal phase silica gel column chromatography (dichloromethane/ethyl acetate=1:1) to provide yellow solid 8Rb (150 mg, yield 77%). MS m/z 328.0 [M+H]$^+$.

Compound 8Rb (150 mg, 0.46 mmol) was dissolved in methanol (10 ml), and Pd/C (10%, 25 mg) was subsequently added. The reaction mixture was stirred at room temperature for 2 hours, filtered and the filtrate was collected, and washed with dichloromethane/methanol (10:1) until the product was completely eluted. The combined filtrate was concentrated under reduced pressure to give gray solid compound 8Rc (100 mg, yield 73%), $^1$H NMR (DMSO-d$_6$, 400 MHz) δ 6.61 (d, J=8.4 Hz, 1 H), 6.09 (dd, J=8.4 Hz, 2.0 Hz, 1 H), 6.03 (d, J=2.4 Hz, 1 H), 4.56 (br s, 2 H), 4.22 (dd, J=10.4 Hz, 2.4 Hz, 1 H), 3.82 (dd, J=10.4 Hz, 9.2 Hz, 1 H), 3.70 (d, J=12.4 Hz, 1 H), 3.59 (dd, J=10.0H, 10 Hz, 2 H), 3.10 (q, J=7.2 Hz, 2 H), 3.01-2.95 (m, 1.H), 2.91-2.82 (m, 1 H), 2.70-2.55 (m, 2 H), 1.22 (t, J=7.2 Hz, 3H); MS m/z 298.0 [M+H]$^+$.

Compound 1a (110 mg, 0.40 mmol), 8Rc (80 mg, 0.27 mmol) and DIPEA (70 mg, 0.54 mmol) were added into isopropanol (3 ml). The reaction mixture was heated in a sealed tube to 80° C. and stirred to react for 16 hrs. LCMS monitored that the reaction was completed, then the reaction mixture was poured into water (8 ml), and extracted with ethyl acetate (5 ml×4). The combined organic layers were washed with saturated brine (50 ml×2), dried over anhydrous sodium sulfate and filtered. The residue obtained by concentrating the filtrate was purified by preparative thin layer chromatography (CH$_2$Cl$_2$/MeOH=20/1) to give pale yellow solid compound 8Rd (80 mg, yield 40%). MS m/z 493.1 [M+H]$^+$, 495.1 [M+H]$^+$.

Compound 8Rd (20 mg, 0.038 mmol), 1b (19 mg, 0.076 mmol), Pd(dppf)Cl$_2$(2.8 mg, 0.0038 mmol) and potassium carbonate (11 mg, 0.076 mmol) were added to dioxane/water (1 ml/0.1 ml). The reaction mixture was heated under microwave conditions to 135 and stirred to react for 1 hour. Then 1b (9.3 mg, 0.038 mmol), Pd(dppf)Cl$_2$ (2.8 mg, 0.0038 mmol) and potassium carbonate (5.3 mg, 0.038 mmol) were added, and the reaction was heated under microwave conditions to 135° C. and stirred to react for 1 hour. LCMS monitored that the reaction was completed, then the reaction liquid was poured into water (4 ml), and extracted with ethyl acetate (3 ml×5), and then washed with saturated brine (2 ml×2), dried over anhydrous sodium sulfate and filtered. The residue obtained by concentrating the filtrate was purified by preparative thin layer chromatography (dichloromethane/ethyl acetate=2/1 to give the product, and then pulped with methanol and diethyl ether for two times to provide brown solid compound 8R (5.9 mg, yield 27%). $^1$H NMR (DMSO-d$_6$, 400 MHz) δ 13.23 (s, 1 H), 9.51 (s, 1 H), 8.65 (s, 1 H), 8.13 (s, 1 H), 8.10 (s, 1 H), 7.99 (s, 1 H), 7.85 (d, J=8.4 Hz, 1 H), 7.74-7.70 (m, 2 H), 7.66-7.60 (m, 2 H), 6.95 (d, J=8.8 Hz, 1 H), 4.39-4.34 (m, 1 H), 3.99-3.89 (m, 2 H), 3.72-3.63 (m, 2 H), 3.18-2.99 (m, 4H), 2.74-2.65 (m, 2 H), 1.24 (t, J=7.2 Hz, 3H). MS m/z 531.2 [M+H]$^+$.

Example 9

Preparation of Compound 9R

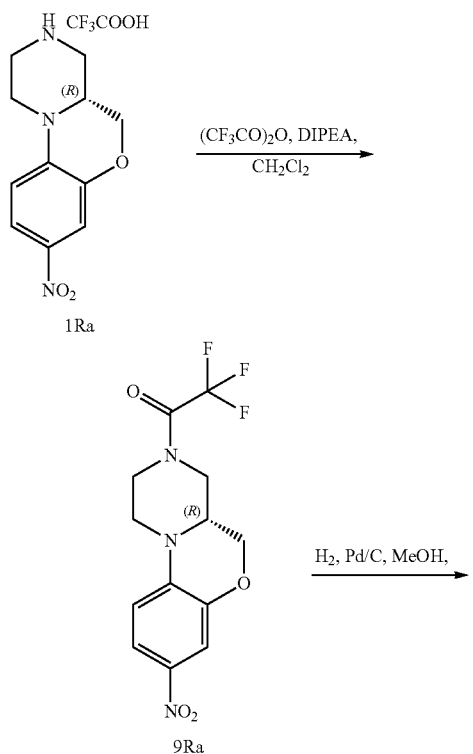

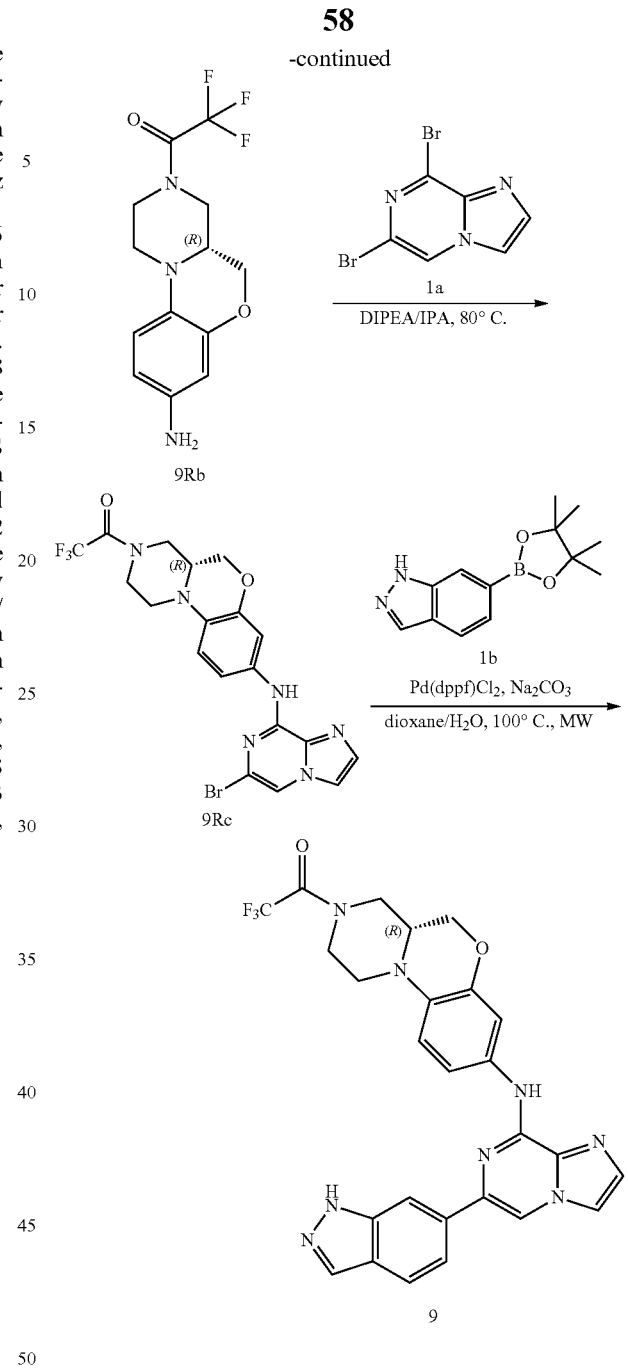

Compound 1Ra trifluoroacetate (500 mg, 1.43 mmol) and DIPEA (554 mg, 4.29 mmol) were added to dichloromethane (20 ml), and then trifluoroacetic anhydride (601 mg, 2.86 mmol) was added slowly at room temperature. The reaction mixture was stirred at room temperature for 2 hours. LCMS monitored that the reaction was completed, then the reaction mixture was poured into water (50 ml), and extracted with dichloromethane (20 ml×4). The combined organic phase was washed with saturated brine (10 ml×2), dried with anhydrous sodium sulfate, filtered, the filtrate was concentrated under reduced pressure. The residue was separated and purified by preparative thin layer chromatography (petroleum ether/ethyl acetate=2/1) to provide yellow solid compound 9Ra (320 mg, yield 68%). $^1$H NMR(CDCl$_3$, 400 MHz) δ 7.86-7.80 (m, 1 H), 7.70 (d, J=2.4 Hz, 1 H), 6.82 and 6.78 (two d, J=9.2 Hz, 8.8 Hz, 1 H), 4.71-4.65 and 4.60-4.55

(two m, 1 H), 4.39-4.33(m, 1 H), 4.19-3.90 (m, 3 H), 3.52-3.36 (m, 2 H), 3.19-3.00 (m, 2 H), 2; MS m/z 332.2 [M+H]⁺.

Compound 9Ra (200 mg, 0.60 mmol) was dissolved in methanol (6 ml), then Pd/C (10%, 100 mg) was carefully added to the reaction system and replaced with hydrogen for three times. The reaction mixture was stirred to react at room temperature for 2 hours. After LCMS detected that the reaction was completed, the mixture was filtered through celite, and the filter cake was washed with anhydrous methanol. The combined organic layer was concentrated under reduced pressure to provide brown solid compound 9Rb (170 mg, yield 93%). MS 302.3 [M+H]⁺.

Compound 1a (291 mg, 1.06 mmol), 9Rb (160 mg, 0.53 mmol) and DIPEA (137 mg, 1.06 mmol) were added to isopropanol (8 ml), and the reaction mixture was heated in a sealed tube to 80° C. and stirred to react for 4 hrs. LCMS monitored that the reaction was completed, then the reaction mixture was poured into water (20 ml), and extracted with ethyl acetate (10 ml×3). The combined organic layer was washed with saturated brine (5 ml×2), dried over anhydrous sodium sulfate and filtered. The residue obtained by concentrating the filtrate under reduced pressure was purified by preparative thin layer chromatography (dichloromethane/methanol=10/1) to give a brown solid compound 9Rc (120 mg, yield 45%). MS m/z 497.2 [M+H]⁺, 499.2 [M+H]⁺.

Compound 9Rc (27 mg, 0.054 mmol), 1b (26 mg, 0.108), Pd(dppf)Cl₂ (4 mg, 0.0054 mmol) and sodium carbonate (13 mg, 0.108 mmol) were added to dioxane/water (1 ml/0.1 ml). The reaction mixture was heated by microwave condition to 100° C. and stirred to react for 1 hour. LCMS monitored that the reaction was completed, then the reaction mixture was poured into water (3 ml), and extracted with ethyl acetate (2 ml×3). The combined organic layer was washed with saturated brine (2 ml×2), dried over anhydrous sodium sulfate and filtered. The residue obtained by concentrating the filtrate under reduced pressure was purified by preparative thin layer chromatography (dichloromethane/methanol=1/1) to give pale yellow solid compound 9 (2 mg, yield 7%). ¹H NMR (DMSO-d₆, 400 MHz) δ 13.24 (s, 11i), 9.53 (s, 1 H), 8.65 (s, 1 H), 8.13 (s, 1 H), 8.10 (s, 1 H), 7.99 (s, 7.85 (d, J=8.4 Hz, 1 H), 7.76-7.68 (m, 2 H), 7.66-7.61 (m, 2 H), 7.00-6.90 (m, 1 H), 4.46-4.33 (m, 2 H), 4.05-3.90 (m, 3 H), 3.25-3.10 (m, 211), 2.85-2.64 (m, 2 H), MS m/z 535.2 [M+H]⁺.

Example 10

Preparation of Compound 10

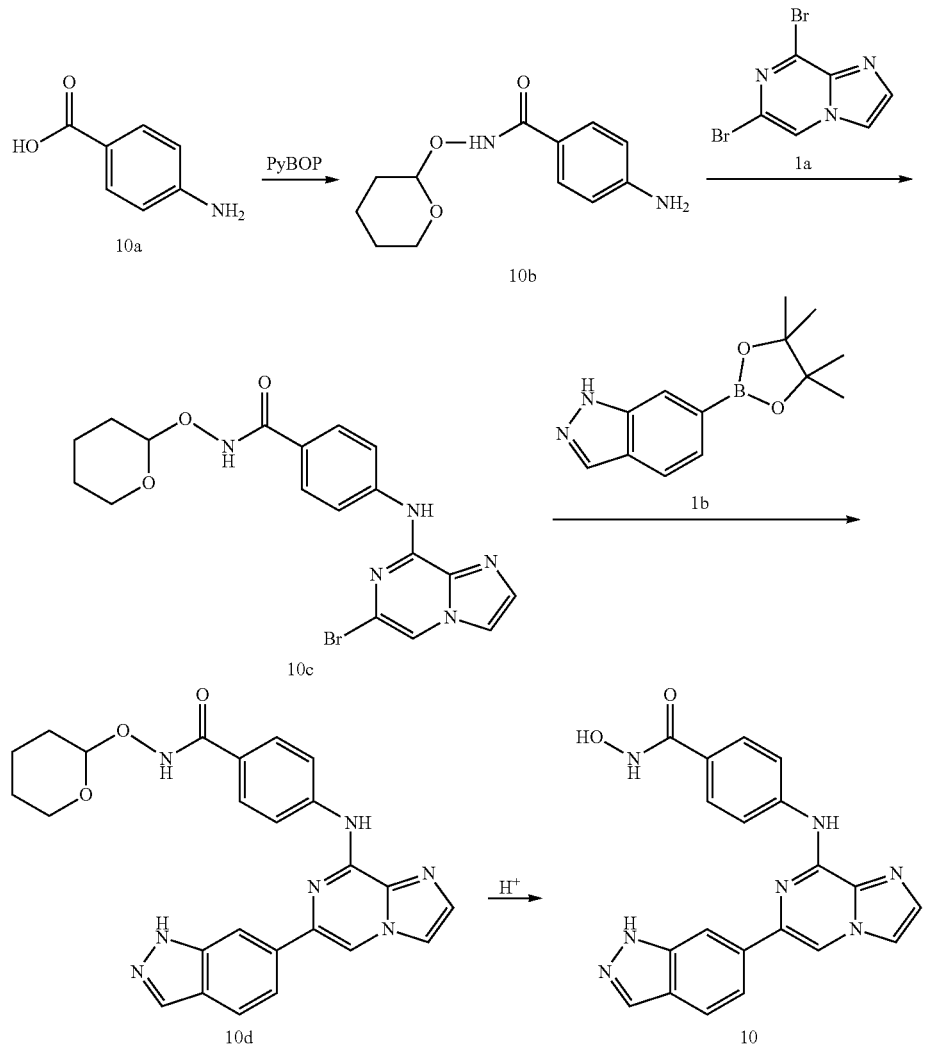

6-Bromoindazole (0.5 g, 2.54 mmol). bis(pinacolato)diboron (0.7 g, 2.79 mmol) and potassium acetate (0.7 g, 7.62 mmol) were dissolved in dimethyl sulfoxide (15 mL). After replaced with nitrogen for three times, Pd(dppf)Cl$_2$DCM (310 mg, 0.38 mmol) was added to the system, and heated to 90° C. under nitrogen atmosphere to reflux for 16 hours. TLC monitored that the raw material disappeared, and product was formed. The reaction was cooled to room temperature, and ethyl acetate (25 ml) and water (25 ml) were added to dilute the reaction solution and filtered. The filter cake was soaked with ethyl acetate (15 mL) and discarded. The filtrate was separated, and the combined organic layer was concentrated to dry to provide crude product. The crude product was purified by silica gel column chromatography (ethyl acetate/hexane=1/50 to 30) to give an off-white solid compound 1b (384 mg, purity 96.8%, yield 62.0%). MS m/z 245.1 [M+H]$^+$.

10a (0.2 g, 1.46 mmol), PyBOP (0.8 g, 1.60 mmol) and triethylamine (0.3 mL) were dissolved in N,N-dimethylformamide (3.6 mL), after replaced with nitrogen for 3 times, O-(tetrahydro-2 H-pyran-2-yl)hydroxylamine (0.2 g, 1.75 mmol) was added and reacted at 15 to 25° C. for 5 hours. HPLC showed that the compound 10a was consumed, water (7.2 ml) was added, the aqueous phase was extracted with ethyl acetate (20 ml×3), and the combined organic phase was concentrated to dry to give the crude product. The crude product was purified by silica gel column chromatography (methanol/dichloromethanol=1/100 to 30) to give an off-white solid 1b (213 mg, purity 91.5%, yield 61.6%). MS m/z 153.0 [M−THP+H]$^+$.

1a (0.5 g, 1.80 mmol), 10b (0.5 g, 1.98 mmol) were dissolved in isopropyl alcohol (12.5 ml), after replaced with nitrogen for three times, N,N-diisopropylethylamine (0.6 ml) was added, and the mixture was heated to 80 to react for 7 days. The reaction solution was concentrated under reduced pressure to give the crude product. The crude product was purified by preparative thin layer chromatography (methanol/dichloromethane=1/30) to give an off-white solid 10c (46 mg, 86.5% purity). MS m/z 432.1 [M+H]$^+$.

10c (0.5 g, 1.15 mmol), 1b (0.3 g, 1.4 mmol) and potassium carbonate (0.3 g, 2.3 mmol) were dissolved in dioxane (7.5 ml) and water (2.5 ml). After replaced with nitrogen for 3 times, Pd(dppf)Cl$_2$·DCM (95 mg, 0.1 mmol) was added, and after replaced with nitrogen for 3 times, warmed to 90° C. to react for 7 hours. The reaction was cooled to room temperature, and ethyl acetate (50 mL) was added, filtered, and the filtrate was concentrated to dryness. The crude product was purified by silica gel column chromatography (methanol/dichloromethane=1/50), the resulting solid was pulped with methanol (2 ml) to provide off-white solid 10d (120 mg, 91,6% purity). MS m/z 470.4 [M+H]$^+$.

10d (0.1 g, 0.2 mmol) was dissolved in methanol (10 mL), and trifluoroacetic acid (0.5 mL) was added and reacted at 15 to 25° C. for 16 hours. The reaction mixture was concentrated to dryness under reduced pressure, methanol (2 ml) was added to pulp so as to give brown solid 10 (41 mg, 95.6% purity, 50% yield). $^1$H NMR (400 MHz, DMSO-d$_6$): δ 11.12 (s, 1 H), 10.02 (s, 1 H), 8.82 (s, 1 H), 8.26-8.29 (d, J=8.7 Hz, 2 H), 8.22 (s, 1 H), 8.07-8.11 (d, J=15.8 Hz, 2 H), 7.82 (m, 3 H), 7.75 (d, J=8.3 Hz, 2 H). MS m/z 386.3 [M+H]$^+$.

Example 11

Preparation of Compound 11

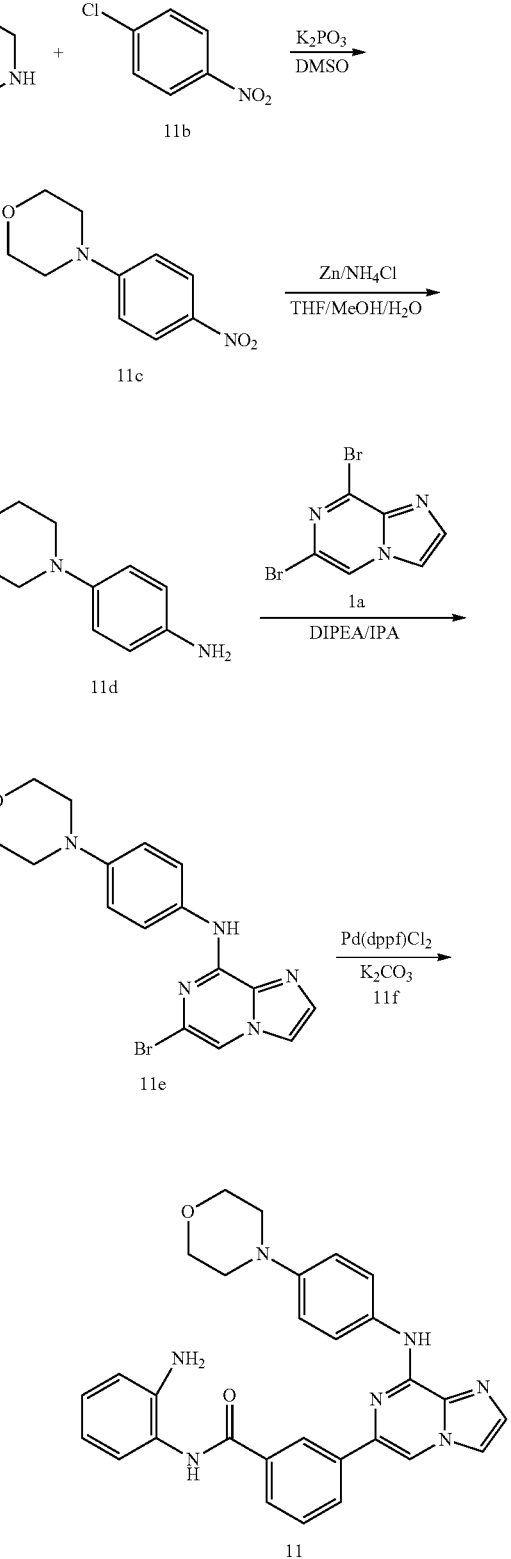

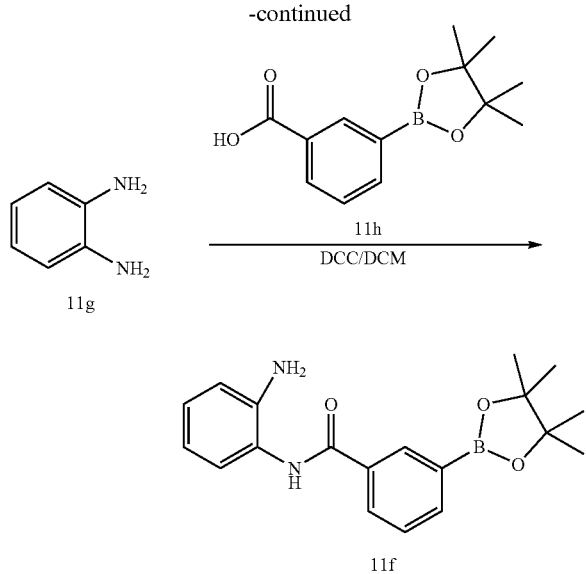

To a 250 ml three-necked bottle, p-chloronitrobenzene (11b, 5.0 g, 31.8 mmol), dimethyl sulfoxide (50.2 ml), morpholine (2.8 g, 38.2 mmol) and potassium carbonate (6.6 g, 47.7 mmol) was added. The system was replaced with nitrogen for three times, and the reaction was heated to 100° C. and stirred to react for 24 hours. The system was cooled to room temperature, and water (150 ml) was added to the reaction mixture, and a large amount of solid was precipitated from the reaction mixture. After filtration, the filter cake was added into ethyl acetate (40 mL) and heated with stirring to make the filter completely dissolved to form a solution. To the resulting solution, petroleum ether (100 ml) was slowly added dropwise within 30 minutes. Then the reaction system was cooled at 0° C. for 1 hour for crystallization. After filtration, the filter cake was dried in a vacuum oven at 60° C. for 6 hours to constant weight to obtain bright yellow solid material 11c (5.6 g, purity 99.4%, yield 84.9%). MS m/z 209.1 [M+H]$^+$.

11c (0.6 g, 2.9 mmol) was dissolved in tetrahydrofuran (12.5 ml), and methanol (12.5 ml) was added and stirred for 5 min. Ammonium chloride (1.5 g, 28.8 mmol) in water (6.5 mL) was added and the mixture was continued to stir for 30 min. Zinc powder (942 mg, 14.4 mmol.) was added to the system and the reaction was continued to stir at 17° C. for 3 hours. The reaction liquid was gradually changed from bright yellow to gray, and the reaction was monitored to have been finished by thin-plate chromatography (methanol/dichloromethane=1:10). After stood for 15 minutes, the reaction was filtered through celite, the cake was rinsed with ethyl acetate (10.5 ml) and the filtrate was concentrated to dryness under reduced pressure. Water was added (5.5 ml) and extracted with ethyl acetate (10 ml×3). The combined organic phase was washed with saturated sodium chloride solution (10.2 mL), dried and concentrated under reduced pressure to give a pale yellow solid lid (500 mg, 99.1% purity, yield 97.4%).

11d (0.5 g, 2.8 mmol), 1a (0.8 g, 2.8 mmol), isopropanol (5.1 ml), and diisopropylethylamine (0.7 g, 5.6 mmol) were added to a 25 ml three-necked flask. The system was replaced with nitrogen for three times under stirring. The system was refluxed for 16 hours in 100° C. oil bath. The system was cooled to 17° C., and concentrated to dryness under reduced pressure, purified by silica gel column chromatography (ethyl acetate/n-hexane=1/10 to 1:3) to give light yellow solid Compound 11e (0.7 g, 99.5% purity, yield 72.6%). MS m/z 374.0 [M+H]$^+$.

11h (0.9 g, 3.7 mmol), 1-hydroxybenzotriazole (0.5 g, 3.7 mmol) and N,N-dimethylformamide (4.1 mL) were sequentially added to a 25 mL single-necked flask. After cooled to 0° C., 1-(3-dimethylaminopropyl)-3-ethylcarbodiimide hydrochloride (0.8 g, 4.4 mmol) and diisopropylethylamine (0.9 g, 7.4 mmol) were added, stirred for 20 minutes and warmed to 13° C. 11g (0.4 g, 3.7 mmol) was added and the reaction was continued to stirred. The reaction was monitored by thin layer chromatography (ethyl acetate:n-hexane=1:1) until the starting material disappeared. After water (8.1 ml) was added to the reaction mixture, the mixture was extracted with ethyl acetate (10 mL×3), the combined organic phase was washed with saturated sodium chloride solution (10.2 ml), and concentrated to dry under reduced pressure. The crude product was purified by silica gel column product (ethyl acetate:n-hexane=4:1) to give a white solid compound 11f (1.0 g, purity 74.4%, yield 79.9%). MS m/z 257.0 [M+H]$^+$.

11e (240 mg, 0.6 mmol), 1,4-dioxane (3.6 ml), potassium carbonate (178 mg, 1.3 mmol), water (1.2 ml), 11f (118 mg, 0.6mmol) and Pd(dppf)Cl$_2$·DCM (46 mg, 0.06 mmol) were added in a 25 ml three-necked flask, and the system was replaced with nitrogen gas for three times. The system was heated to 90° C. so as to reflux for 16 hours. HPLC showed that the reaction was completed, and the reaction mixture was cooled to 17° C. and concentrated to dry under reduced pressure. The crude product was purified by preparative thin-layer chromatography (methanol/dichloromethane=1/15, R$_f$=0.3), and then the silica gel containing the product band was passed through a flash column (550 ml, methanol/dichloromethane=1/10) so as to obtain an off-white solid 11 (35 mg, purity 96.5%). $^1$H NMR (400 MHz, DMSO-d$_6$) δ 9.76 (s, 1 H), 9.56 (s, 1 H), 8.72 (s, 1 H), 8.63 (s, 1 H), 8.20 (d, J=7.8 Hz, 1 H), 8.07-7.88 (m, 4 H), 7.64 (d,=9.7 Hz, 2 H), 7.24 (d, J=7.8 Hz, 1 H), 6.96 (dd, J=21.3, 8.1 Hz, 3 H), 6.81 (d, J=7.9 Hz, 1 H), 6.62 (t, J=7.6 Hz, 1 H), 4.98 (s, 2 H), 3.71 (t, J=4.7 Hz, 4 H), 2,99 (t/=4.7 Hz, 4H). MS m/z 506.4 [M+H]$^+$.

Example 12

Preparation of Compound 12

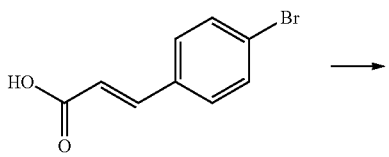

-continued
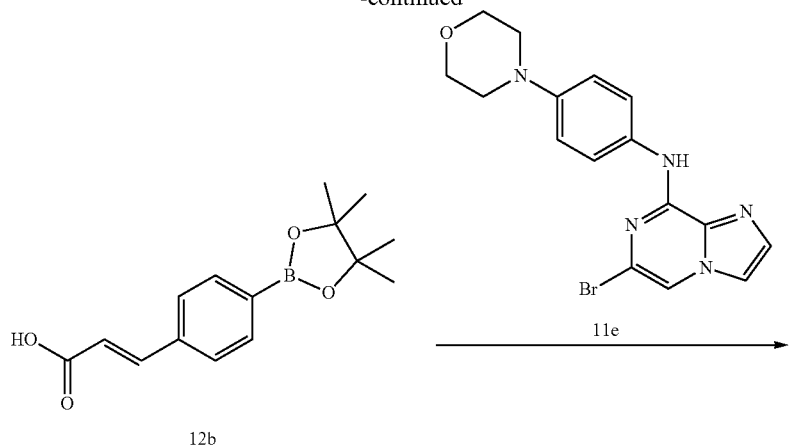
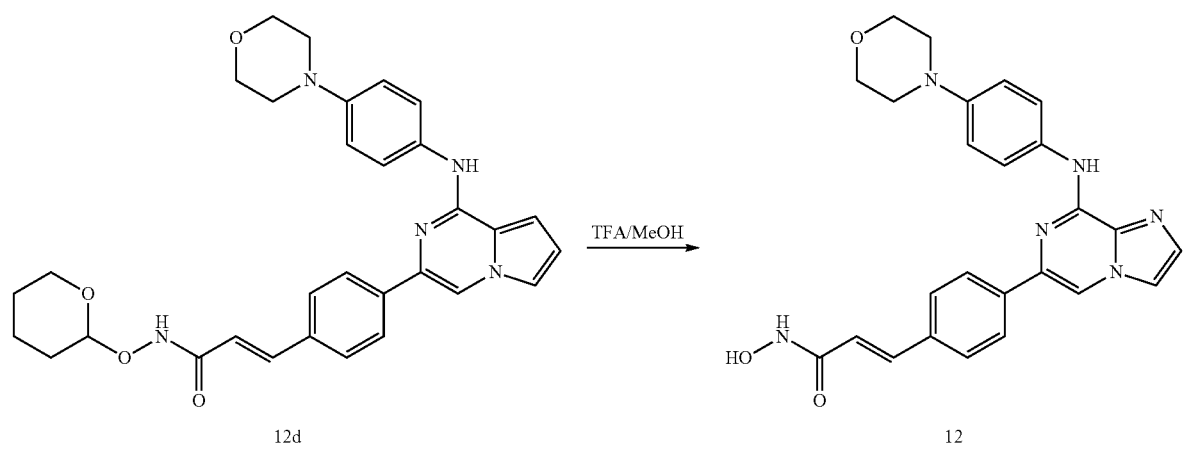

Compound 12b was prepared by compound 12a according to the synthesis of compound 1b. The synthesis method of 12 from 11e and 12b by a multi-step reaction can refer to the synthesis of compound 10. $^1$H NMR (400 MHz, DMSO-$d_6$): δ 10.47 (s, 1 H), 8.82 (s, 1 H), 8.19 (s, 1 H), 8.03-8.09 (m, 5 H), 7.70-7.72 (d, J=8.2 Hz, 1 H), 7.50-7.53 (d, J=15.8 Hz, 1 H), 7.33 (br, 2 H), 6.55-6.58 (d, J=15.8 Hz, 1 H), 3.88 (t, 4 H), 3.29 (t, 4 H). MS m/z 457.6 [M+H]$^+$.
Example 13
Preparation of Compound 13
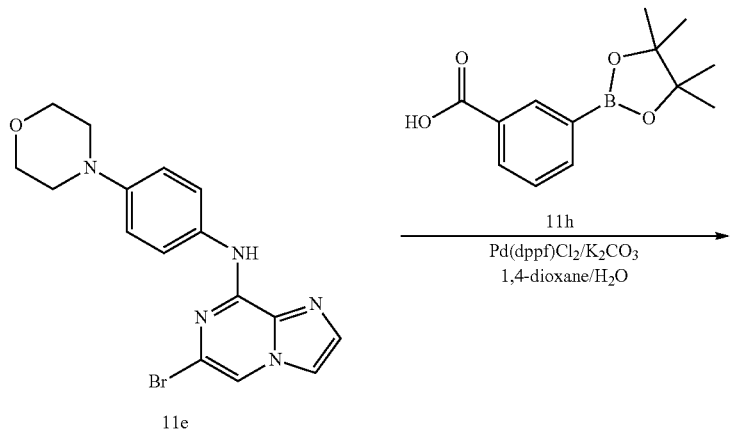
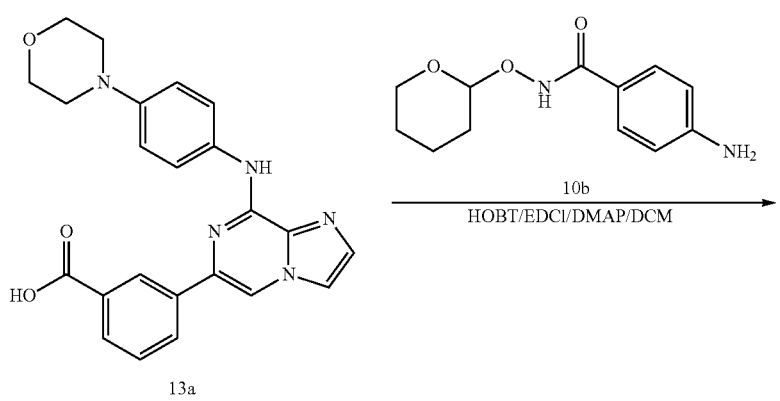
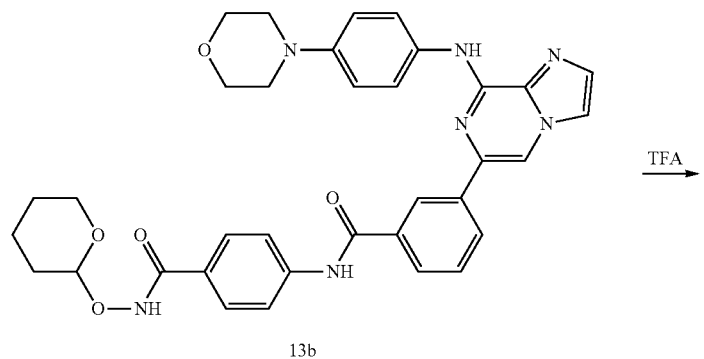

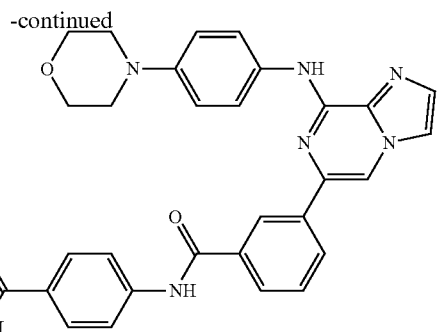

13

11e (3.0 g, 8.1 mmol), 11h (2.4 g, 9.6 mmol), 1,4-dioxane (30 ml), water (6.1 ml), potassium carbonate (2.2 g, 16.1 mmol) and Pd(dppf) Cl$_2$·DCM (164 mg, 0.2 mmol) were added successively into a 100 ml three-necked flask. The system was replaced with nitrogen gas for three times under stirring, and then warmed to 90° C. to reflux for 16 hours. After filtration, the filter cake was soaked with methanol (20 ml×3) and discarded. The combined organic phase was concentrated to dry under reduced pressure, and the resulting solid was washed pulped with n-hexane (3 mL)-dichloromethane (12 ml) under 21° C. for 2 h. After filtration, the filter cake was washed with dichloromethane (12.3 mL) and dried in a blast oven for 16 hours under 40° C. to give light green solid compound 13a (3.3 g, purity 94.2%, yield 98.8%). $^1$H NMR (400 MHz, DMSO-d$_6$) δ 9.40 (s, 1 H), 8.56 (s, 1 H), 8.46 (t, J 1.8 Hz, 1 H), 8.08-7.99 (m, 3H), 7.97-7.80 (m, 4H), 7.61 (s, 1 H), 7.36 (t, J=7.6 Hz, 1 H), 7.27-7.19 (m, 2 H), 6.97 (d, J=8.9 Hz, 2 H), 3.75 (t, J 4.7 Hz, 4H), 3,08 (t, J=4.8 Hz, 4H).

13a (0.2 g, 0.5 mmol) was dissolved in dichloromethane (2.3 ml), and 1-hydroxybenzotriazole (71 mg, 0.5 mmol), 1-(3-dimethylaminopropyl)-3-ethylcarbodiimide hydrochloride (138 mg, 0.7 mmol) and 4-dimethylamine pyridine (118 mg, 0.9 mmol) were added sequentially under stirring. The system was stirred at 25° C. to react for 0.5 hours. 10b (114 mg, 0.5 mmol) was added and the reaction was stirred at 25° C. to react for 16 h. The reaction was concentrated under reduced pressure to dryness, and purified the crude by silica gel column (methanol/dichloromethane=1/200 to 1/75) to give yellow solid 13b (192 mg, purity 78.5%, yield 62.9%).

13b (190 mg, 0.3 mmol) was dissolved in methanol (2.1 mL) and trifluoroacetic acid (216 mg, 1.5 mmol) was added dropwise at 25° C. After the dropwise addition was completed, the system was stirred for 0.5 hours, and then warmed to 40° C. and stirred to react for 20 hours. The reaction solution was cooled to 25° C. After filtration, the filter cake was pulped with isopropanol (3.1 mL) at 85° C. for 1 hour. The system was slowly nature cooled to 25° C. by constant stirring and filtered. The filter cake was dried in a vacuum oven at 40° C. for 16 hours to give a yellow solid 13 (30 mg, purity 90.1%, yield 18.2%). $^1$H NMR (400 MHz, DMSO-d$_6$) δ 11.17 (s, 1 H), 1068 (s, 1 H), 9.65 (s. 1 H), 8.78 (s, 1 H), 8.61 (s, 1 H), 8.22 (d, J=7.5 Hz, 1 H), 8.12-7.60 (m, 11 H), 6.96 (t, J=9.8 Hz, 2 H), 3.70 (d, J=9.1 Hz, 4H), 2.98 (t, J=4.4 Hz, 4H). MS m/z 550.5 [M+H]$^+$.

Example 14

Preparation of Compound 14

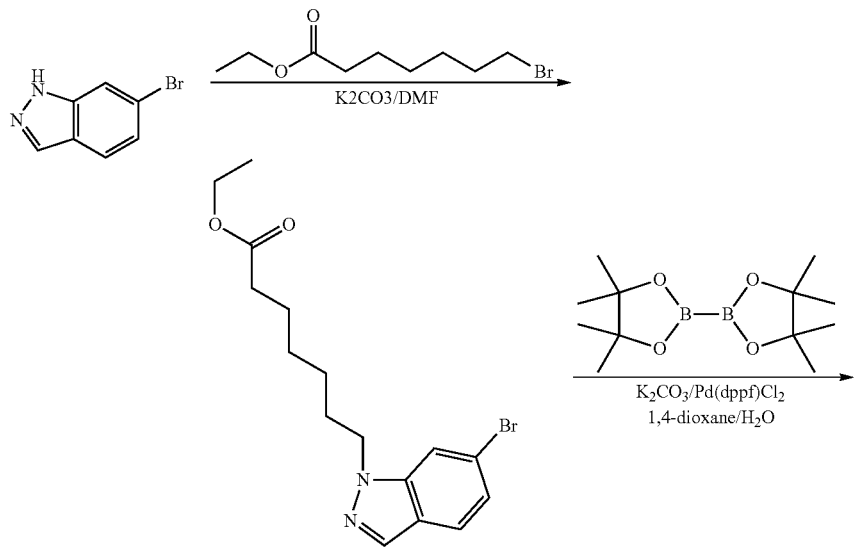

14a

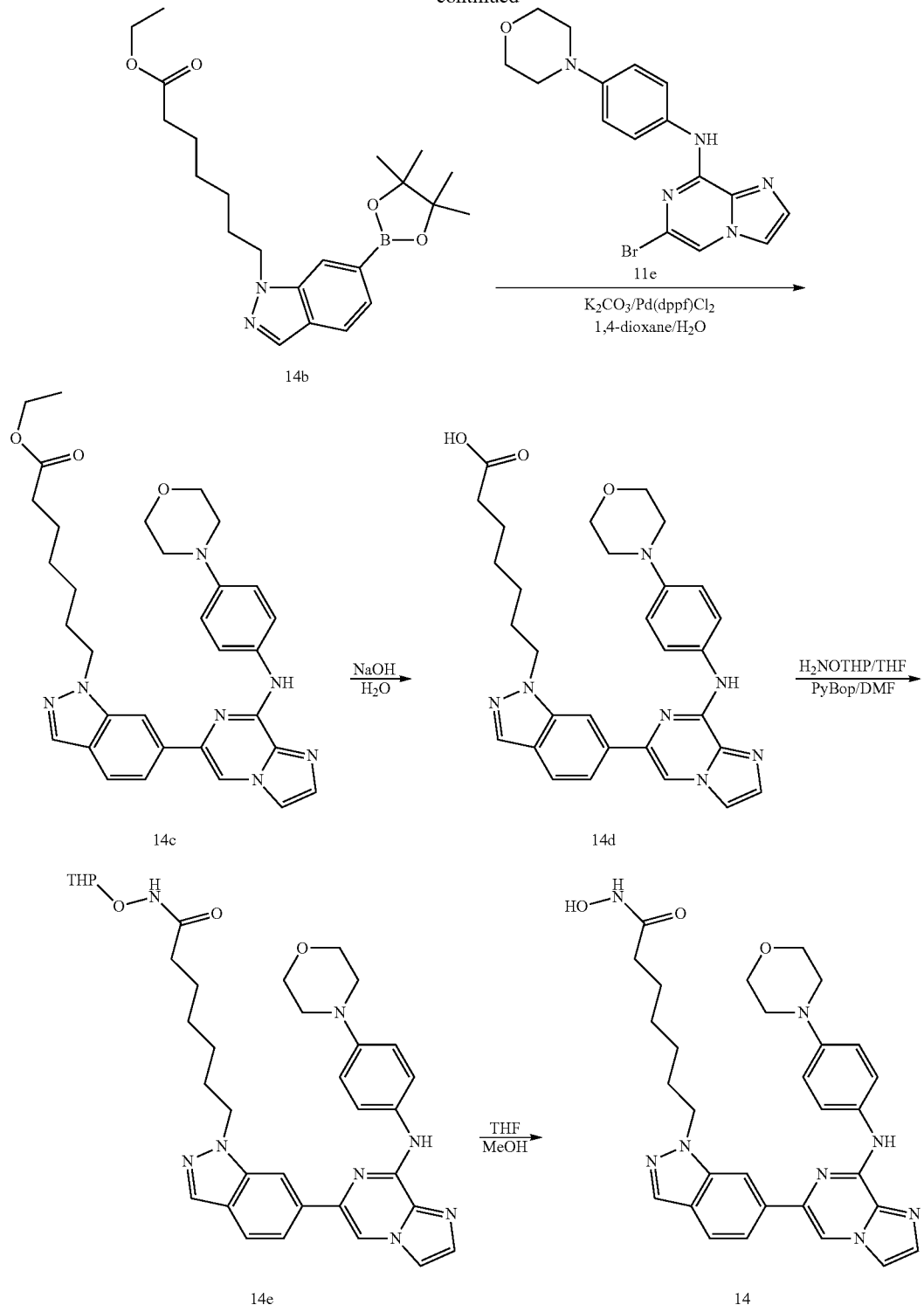

6-Bromocarbazole (6.0 g, 30.6 mmol), methyl 7-bromo-heptanoate (10.8 g, 45.9 mmol), N,N-dimethylformamide (60.5 ml) and potassium carbonate (12.7 g, 91.8 mmol) were sequentially added to a 100 ml three-necked flask. The system was heated to 100° C. and stirred to react for 6.5 hours. The reaction was monitored by thin layer chromatography (ethyl acetate/n-hexane=1/1, UV=254 nm) until the starting material disappeared. Water (120 ml) was added after the reaction mixture was cooled to 17° C., and extracted with ethyl acetate (50 ml×3). The combined organic phases were washed with saturated aqueous solution of sodium chloride (120 mL×3) and dried over anhydrous sodium sulfate. The organic phase was concentrated under reduced pressure to give the crude product, which was purified by silica gel column chromatography (ethyl acetate/ n-hexane=1/20 to 1/5) to give orange-red solid 14a (4.6 g, purity 92.4%, yield 42.7%).

The synthesis of the compound 14 by a multi-step reaction from the compound 14a can be carried out by referring to the synthesis steps of the above compounds 10, 11, and 12. Compound 14: bright yellow solid (purity 91.0%). $^1$H NMR (400 MHz, DMSO-d$_6$) δ 10.30 (s, 1 H), 9.66 (s, 1 H), 8.76 (s, 1 H), 8.27 (s, 1 H), 8.13-7.94 (m, 4 H), 7.90-7.69 (m, 3 H), 7.08 (d, J=8.5 Hz, 2 H), 4.46 (t, J=6.9 Hz, 2 H), 3.80 (t, J=4.7 Hz, 4H), 3.16 (t, J=4.7 Hz, 4 H), 1.90 (t, J=7.2 Hz, 4 H), 1.44 (q, J=7.2 Hz, 2 H), 1.36-1.21 (m, 4 H). MS m/z 555.6 [M+H]$^+$.

Example 15

Preparation of Compound 15

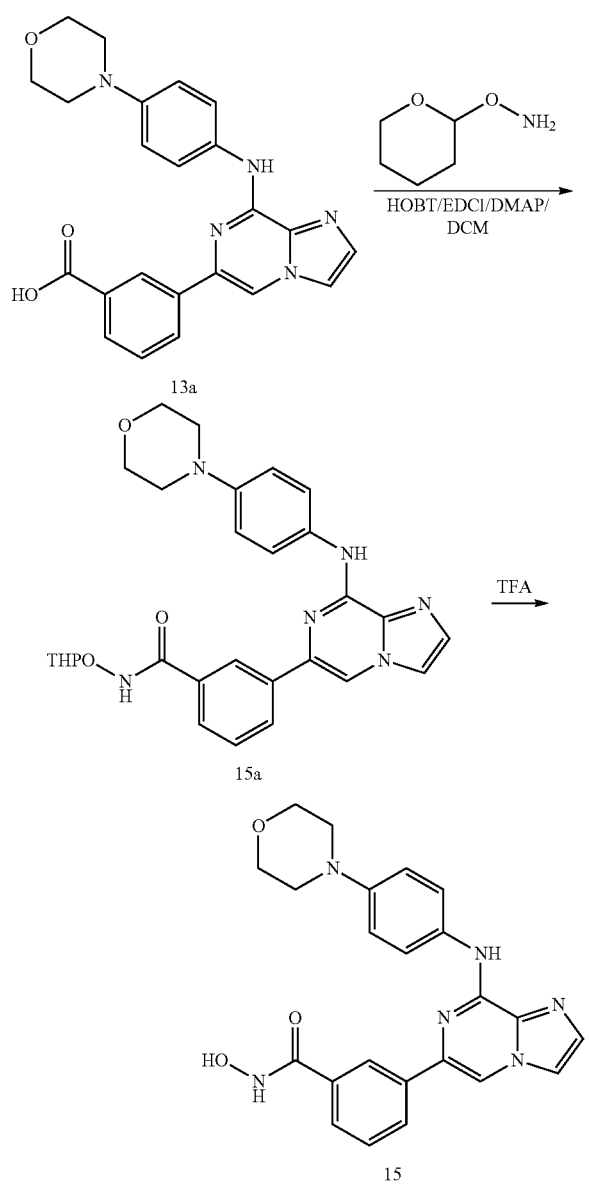

The synthesis procedure of the compound 10b was referred, compound 13 (0.7 g) and O-(tetrahydro-2 H-pyran-2-yl)hydroxylamine was reacted at 21° C. for 5 hours to obtain a pale yellow solid compound 15a (0.6 g, purity 93.6%, yield 62.7%). MS m/z 515.4 [M+H]$^+$.

The synthesis process of compound 10 was referred. 15a (150 mg) and trifluoroacetic acid were reacted at 21° C. for 24 hours to give bright yellow solid 15 (30 mg, purity 95.9%, yield 23.9%). $^1$H NMR (400 MHz, DMSO-d$_6$) δ 11.29 (s, 1 H), 9.52 (s, 1 H), 9.09 (s, 1 H), 8.65 (s, 1 H), 8.49 (s, 1 H), 8.38 (s, 1 H), 8.14 (d, 7.6 Hz, 1 H), 8.01 (d, J=8.6 Hz, 3 H), 7.75-7.53 (m, 3H), 6.97 (d, J=8.6 Hz, 2 H), 3.76 (t, J=4.7 Hz, 4 H), 3.09 (t, J=4.8 Hz, 4 H). MS m/z 431.3 [M+H]$^+$.

Example 16

Preparation of Compound 16

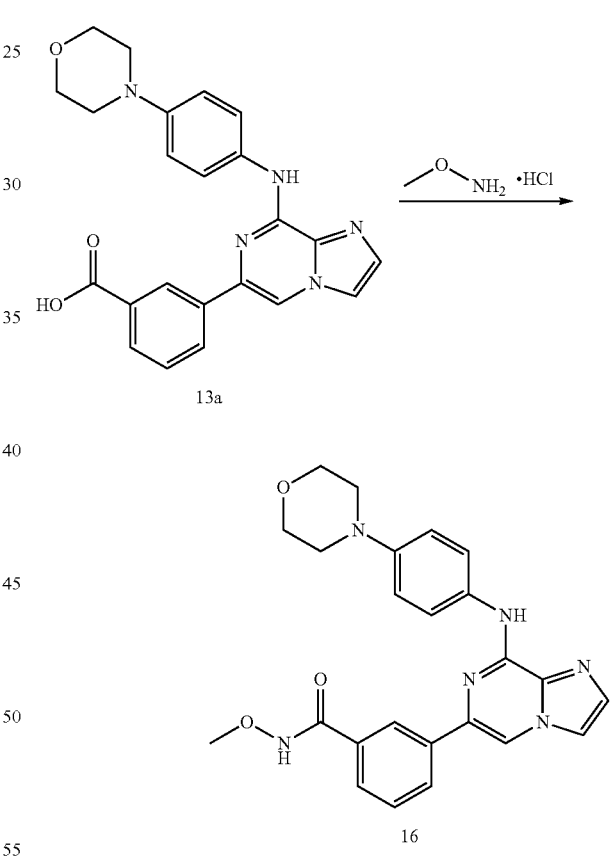

The synthesis procedure of the compound 10b was referred, 13a (200 mg) and O-methylhydroxylamine hydrochloride was reacted to afford white solid compound 16 (46 mg, purity 96.9%, yield 21.4%). $^1$H NMR (400 MHz, DMSO-d$_6$) δ 11.82 (s, 1 H), 9.53 (s, 1 H), 8.66 (s, 1 H), 8.37 (t, 1.8 Hz, 1 H), 8.17 (dt, J=7.8, 1.5 Hz, 1 H), 8.05-7.97 (m, 3 H), 7.72 (dt, J=7.8, 1.3 Hz, 1 H), 7.65 (d, J=1.1 Hz, 1 H), 7.59 (t, J=7.7 Hz, 1 H), 7.01-6.93 (m, 2 H), 3.75 (d, J=4.9 Hz, 7 H), 3.12-3.05 (m, 4 H). MS m/z 445.6 [M+H]$^+$.

Example 17
Preparation of Compound 17
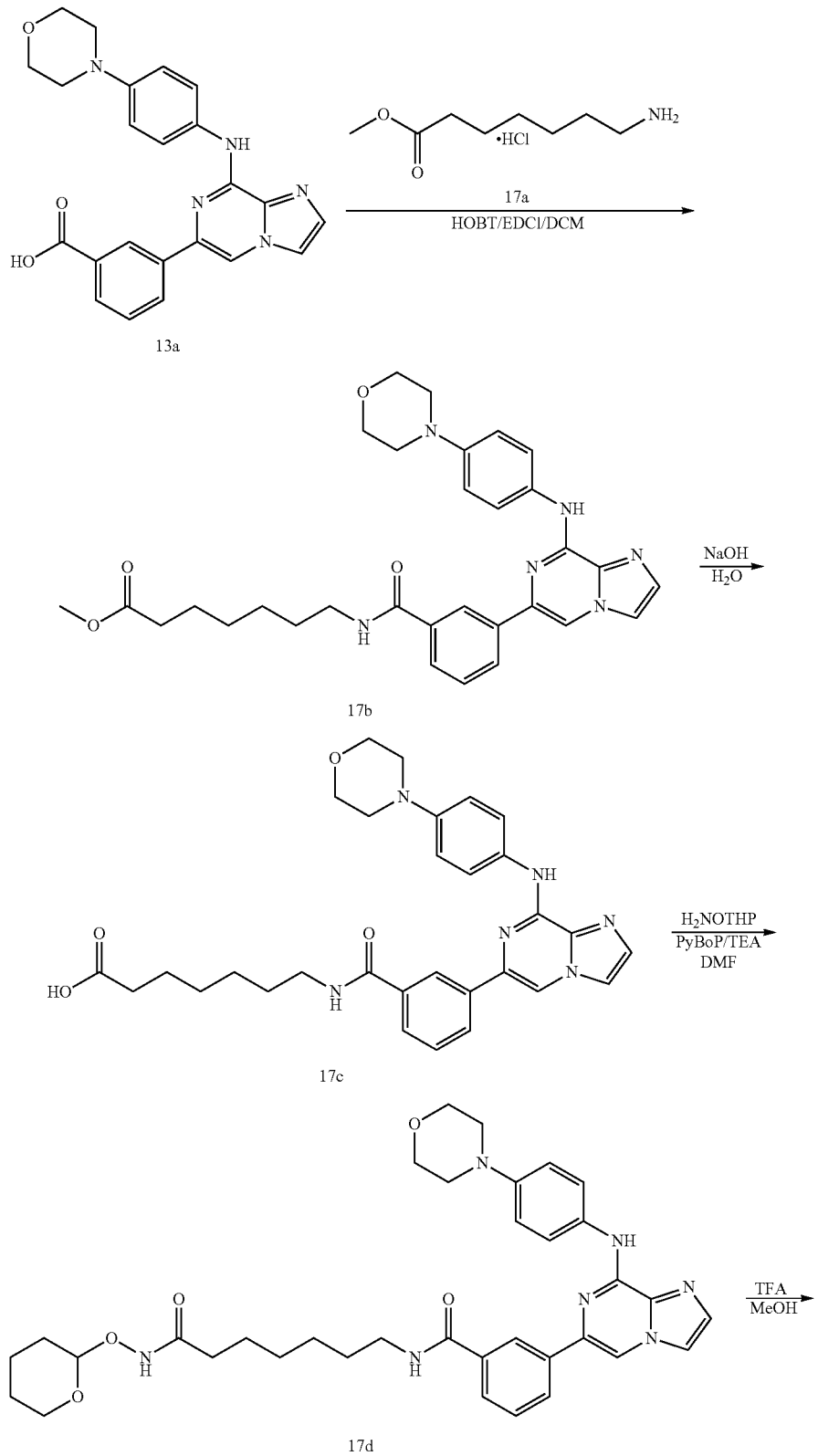

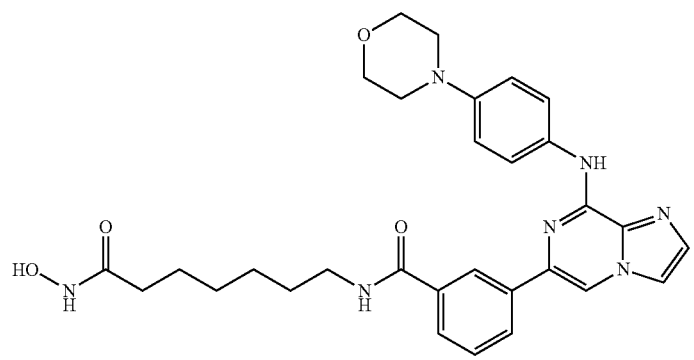
17
Compound 17 was prepared from compound 13a by a multi-step reaction. The specific experimental procedure was according to the synthesis of the above compound 10-13. Compound 17: $^1$H NMR (400 MHz, DMSO-d$_6$) δ 10.35 (s, 1 H), 9.52 (s, 1 H), 8.66 (s, 1 H), 8,56 (t, J=5.6 Hz, 1 H), 8.42 (t, J=1.8 Hz, 1 H), 8.14 (dt, J=7.8, 1.5 Hz, 1 H), 8.08-7.98 (m, 3 H), 7.81 (dt, J=7.8, 1.5 Hz, 1 H), 7.65 (d, J=1.1 Hz, 1 H), 7.57 (t, J=7.8 Hz, 1 H), 7.02-6.94 (m, 2 H), 3.75 (dd, J=5.9, 3.6 Hz, 4H), 3.13-3.04 (m, 4H). MS m/z 559.0 [M+H]$^+$.
Example 18
Preparation of Compound 18
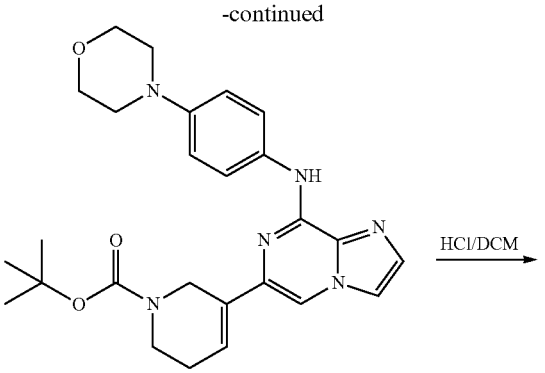
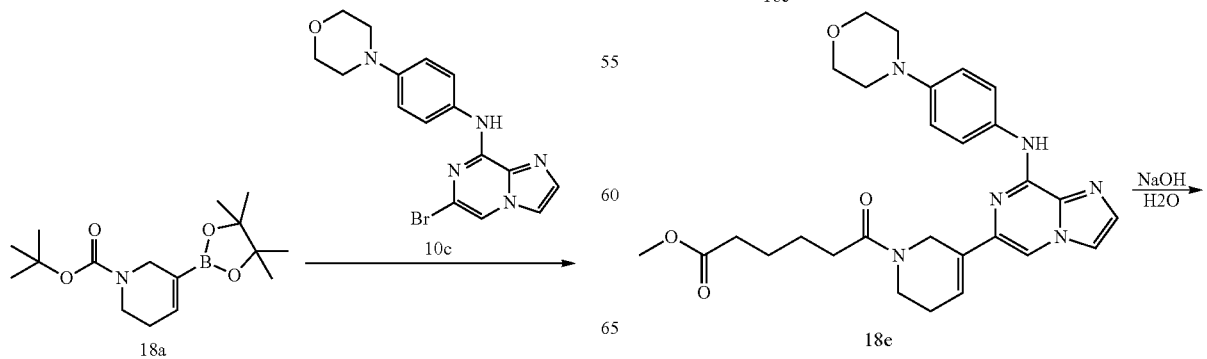

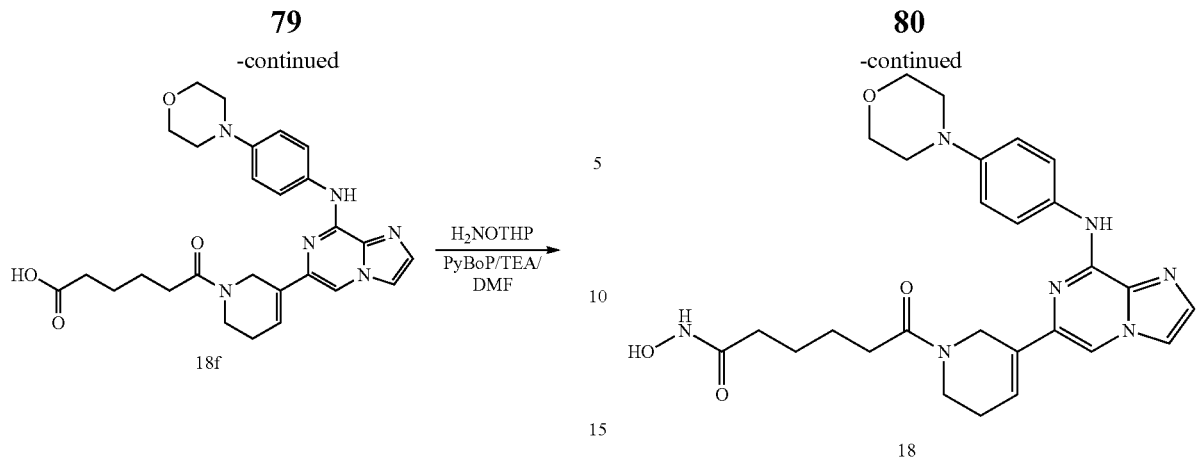
Compound 18 was prepared by a multi-step reaction from compound 18a and compound 10c. The specific experimental procedure was according to the synthesis of the above compound 10-13. Compound 18: $^1$H NMR, (400 MHz, DMSO-$d_6$) δ 10.35 (s, 1 H), 9.37 (d, J=14.6 Hz, 1 H) 8.66 (s, 1 H), 8.08 (d, J=26.4 Hz, 1 H), 7.98-7.85 (m, 3 H), 7.58 (d, 10.2 Hz, 1 H), 6.94 (d, J=8.8 Hz, 2 H), 6.78 (d, J=17.7 Hz, 1 H), 4.37 (s, 2 H), 3.74 (dd, J=6.0, 3.5 Hz, 4 H), 3.61 (dt, J=8.5, 5.8 Hz, 3H), 3.07 (tt, J=5.1, 2.2 Hz, 6H), 2.47-2.23 (m, 4H), 1.97 (d/=6.8 Hz, 2 H), 1.53 (dd, J=7.0, 3.6 Hz, 4 H), 1.24 (t, J=5.9 Hz, 7 H). MS m/z 520.5 [M+H]$^+$.
Example 19
Preparation of Compound 19
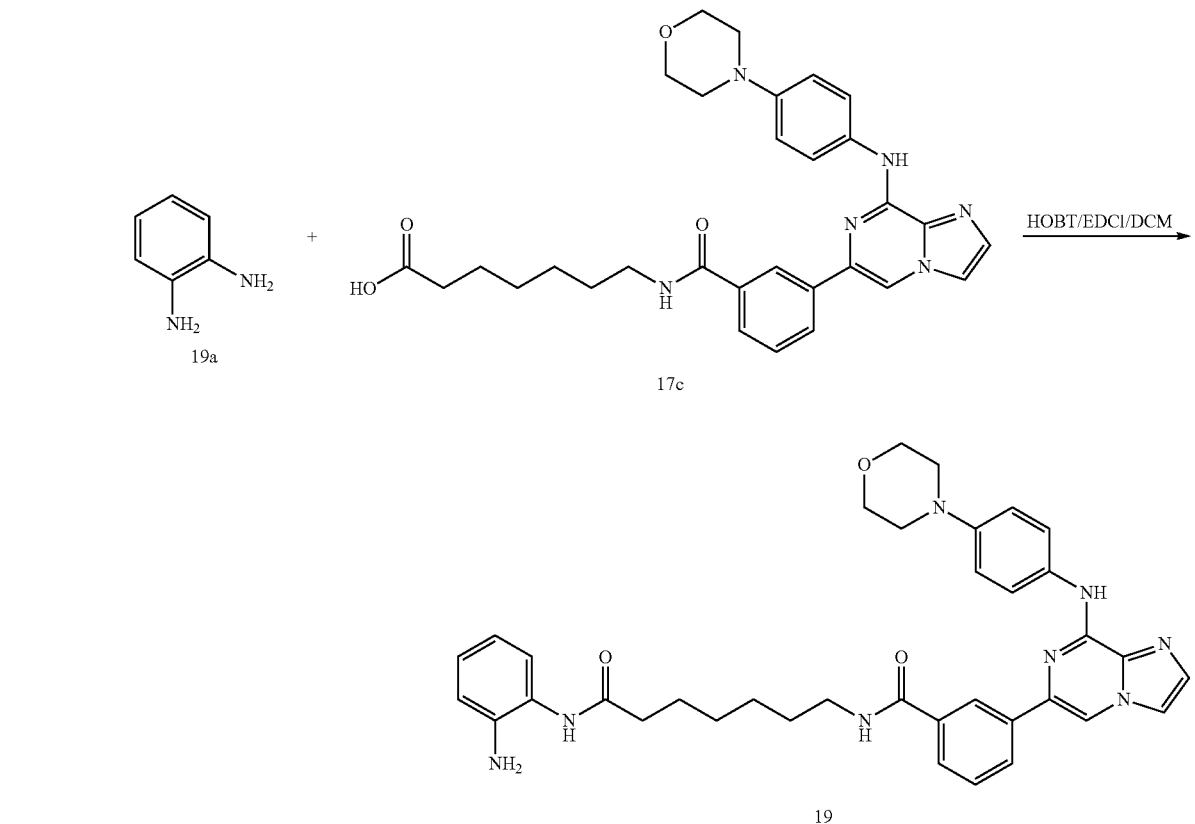

According to the synthetic procedure of the compound 13, 17c (100 mg) and compound 19a were reacted at room temperature for 16 hours, followed by purification to obtain bright yellow solid 19 (50 mg, purity 96.4%, yield 42.9%). $^1$H NMR (400 MHz, DMSO-$d_6$) δ 9.51 (s, 1 H), 9.08 (s, 1 H), 8.64 (s, 1 H), 8.54 (t, J=5.6 Hz, 1 H), 8.41 (t, J=1.8 Hz, 1 H), 8.16-8.09 (m, 1 H), 8.05-7.97 (m, 3 H), 7.81 (dt, J=7.8, 1.4 Hz, 1 H), 7.66-7.51 (m, 2 H), 7.15 (dd, J=7.9, 1.5 Hz, 1 H), 7.01-6.83 (m, 3H), 6.70 (dd, J=7.9, 1.5 Hz, 1 H), 6.56-6.48 (m, 1 H), 4.80 (s, 2 H), 3.75 (dd, J=6.0, 3.7 Hz, 4H), 3.12-3.03 (m, 4H), 2.32 (t, J=7.4 Hz, 2 H), 1.60 (d, J=10.7 Hz, 4H), 1.46-1.19 (m, 61-1). MS m/z 633.9 [M+H]$^+$.
Example 20
Preparation of Compound 20
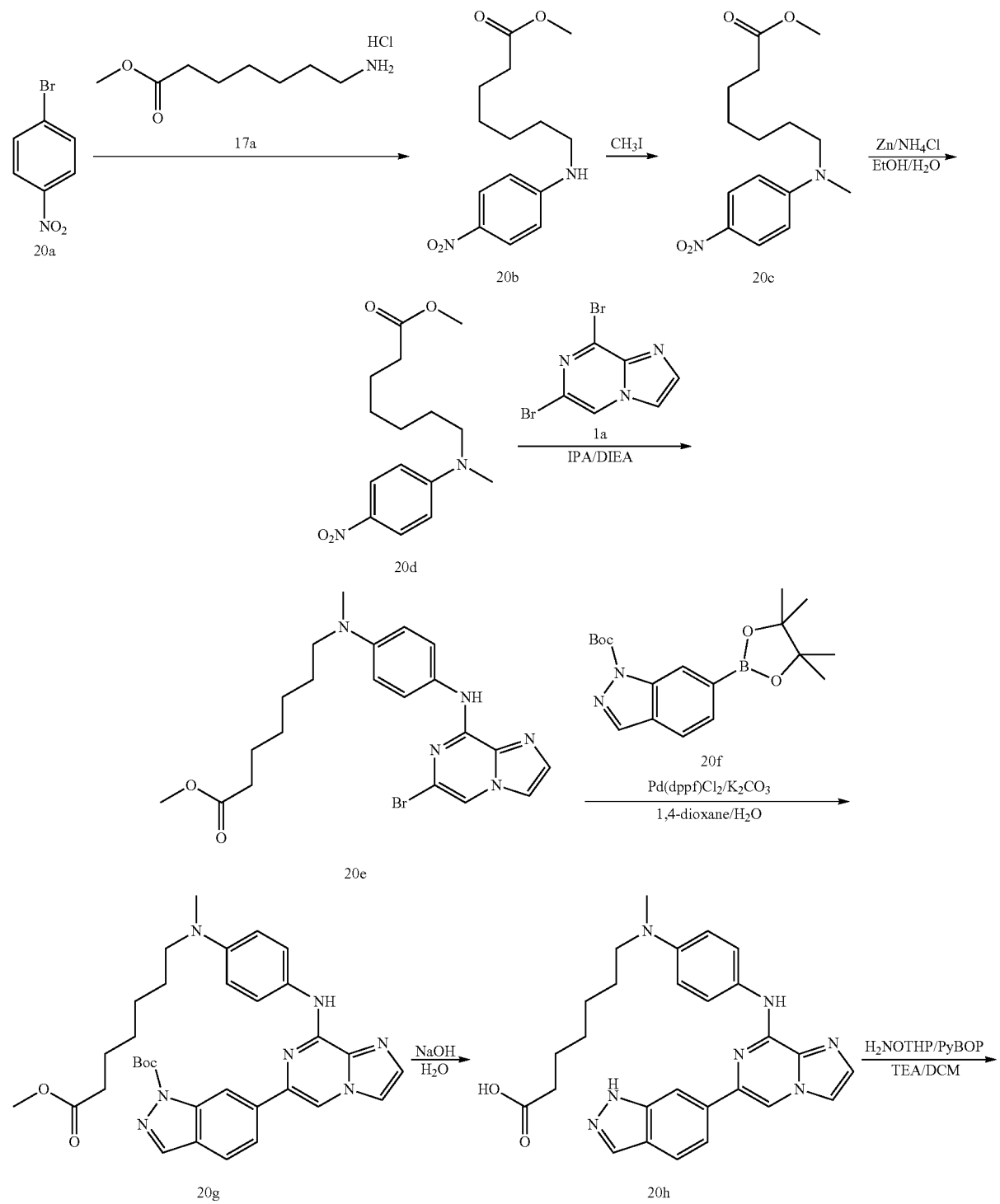

-continued

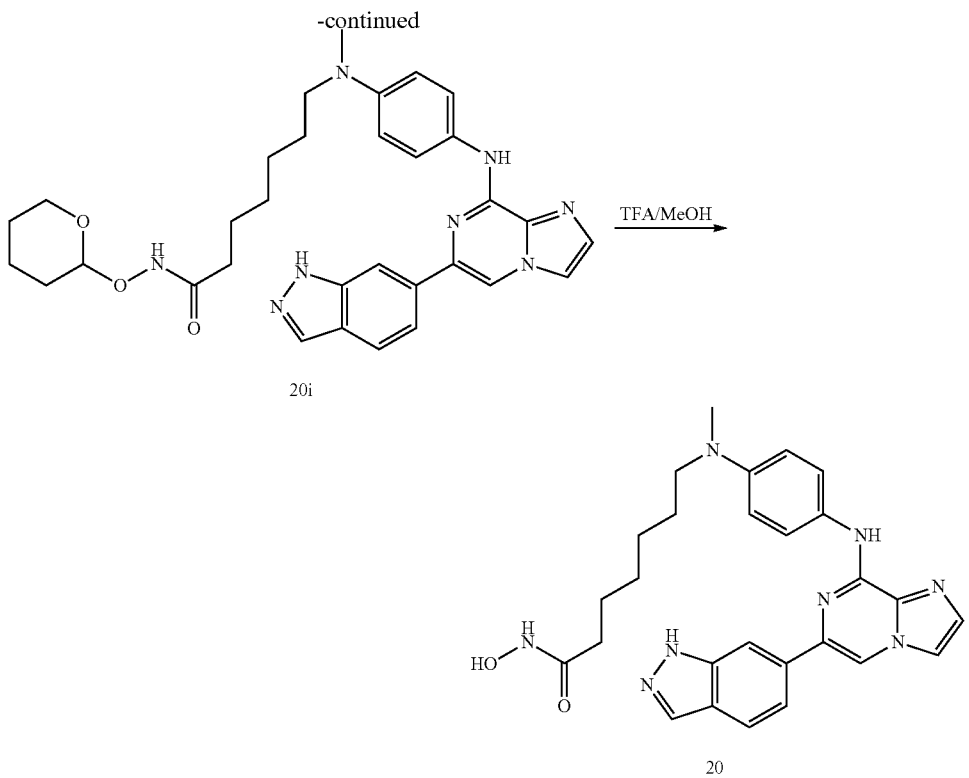

20a (2.1 g, 9.9 mmol), 17a (2.3 g, 11.9 mmol), potassium carbonate (4.1 g, 29.7 mmol), potassium iodide (146 mg, 1.0 mmol), iodine cuprous (0.4 g, 2.0 mmol), L-valine (144 mg, 1.0 mmol) and N,N-dimethylacetamide (20.2 ml) were added to a 50 ml three-necked flask successively. The system was replaced with nitrogen for three times, and stirred to react at 90° C. for 24 hours. Water (40 ml) was added, and the mixture was extracted with ethyl acetate (30 ml×3). The combined organic phase was washed with saturated brine (60 mL), dried, filtered, and concentrated under reduced pressure. The crude product was purified by silica gel column chromatography (hexane:ethyl acetate=10:1) to give yellow solid compound 20b (1.0 g, purity 91.8%, yield 36.1%). MS m/z 280.9 [M+H]$^+$.

20b (0.6 g, 2.1 mmol), sodium hydride (0.1 g, 3.2 mmol), N,N-dimethylformamide (6.1 ml) were added to 50 ml three-necked flask, and the system was replaced with nitrogen for three times. The reaction was stirred for 1 hour after cooled to 0° C., and then with methyl iodide (0.9 g, 6.4 mmol) was added and stirred for 1 hour. Ethyl acetate (35.5 ml) was added to the reaction mixture, and the organic phase was washed with saturated brine (40.5 ml). The organic phase was concentrated to dryness and purified by silica gel column chromatography (hexane:ethyl acetate=10:1) to provide bright yellow oil 20c (1 g, yield 92.1%). MS m/z 295.4 [M+H]$^+$.

20c (0.4 g, 1.4 mmol), zinc powder (0.5 g, 7.1 mmol), ammonium chloride (0.7 g, 14.3 mmol), ethanol (4.2 ml) and water (0.8 ml) were added to a 25 ml three-necked flask. The system was replaced with $N_2$ for three times, and heated to 60° C. and stirred to react for 16 hours. The reaction solution was suction filtered, and the filtrate was concentrated to remove the ethanol, and extracted with ethyl acetate (10 mL) for three times. The combined organic phases were concentrated to give compound 20d (480 mg, 83.9% purity). MS m/z 265.2 [M+H]$^+$.

20d (0.4 g, 1.5 mmol), 1a (0.4 g, 1.5 mmol), N,N-diisopropylethylamine (0.6 g, 4.5 mmol), isopropanol (4.1 mL) were added into reaction flask. The system was replaced with nitrogen for three times, warmed to 90° C. and stirred for 16 hours. The reaction mixture was concentrated to dry and purified by silica gel column chromatography (hexane:ethyl acetate=8:1) to give compound 20e (0.6 g, purity 88.6%, and the yield was 82.6%). MS m/z 460.3 [M+H]$^+$.

20e (0.7 g, 1.5 mmol), 20f (1.6 g, 4.6 mmol), potassium carbonate (0.4 g, 3.1 mmol), Pd(dppf) $Cl_2$ (125 mg, 0.2 mmol), 1,4-dioxane (7.1 ml) and water (1.4 ml) were added to pressure-resistant bottle. After the system was replaced with nitrogen for 3 times, the system was warmed to 110° C. and stirred to react for 16 hours. The reaction solution was filtered, concentrated to dry and purified by silica gel column chromatography (n-hexane:ethyl acetate=2:1) to gave compound 20g (0.5 g, purity 99.8%, yield 63.4%). MS m/z 498.6 [M-Boc+H]$^+$.

20g (0.5 g, 0.9 mmol), sodium hydroxide (0.2 g, 4.8 mmol), methanol (48.2 ml) and water (10.2 ml) were successively added into a reaction flask, and the mixture was warmed to 40° C. and stirred to react for 16 hours. The reaction mixture was adjusted to 3-4 with dilute hydrochloric acid and then concentrated to dry to give Compound 20h (0.3 g, purity 100%). MS m/z 484.4 [M+H]$^+$.

20h (0.6 g, 1.3 mmol), HOBT (0.2 , 1.4 mmol), EDCI (0.3 g, 1.7 mmol), N,N-diisopropylethyl amine (0.3 g, 2.6 mmol) , $H_2$N-OTHP (0.2 g, 1.5 mmol), and N,N-dimethylacetamide (15.2 ml) were added successively into a reaction flask and stirred at room temperature for 6 hours. Water (30.5 ml) was added, and the mixture was extracted with ethyl acetate (150 mL×3). The combined organic phase was washed with saturated sodium chloride (50.5 ml), and the combined organic phase was concentrated to dry and purified by silica gel column chromatography (methanol:dichloromethane=1:50). The solid compound 20i (0.4 g, purity 98.3% yield 56.1%) was obtained. MS m/z 583.7 [M+H]⁺.

20i (0.2 g, 0.3 mmol), methanol (4.1 ml) and trifluoroacetic acid (0.5 g, 3.4 mmol) were successively added into a reaction flask and stirred at room temperature for 24 hours. The reaction solution was filtered, and the filter cake was dried in vacuo to provide compound 20 (50 mg, purity 99.5%, yield 29.2%), $^1$H NMR (400 MHz, DMSO-$d_6$) δ 10.31 (br, 1 H), 9.85 (br, 1 H), 8.74 (s, 1 H), 8.23 (br, 2 H), 8.15 (s, 1 H), 8.11 (d, J=0.9, 1 H), 8.05 (d, J=0.9 , 2 H), 7.85-7.87 (d, J=8.4 Hz, 1 H), 7.74(d, J=1.3 Hz, 1 H),7.72 (d, J=2.7 Hz, 1 H), 7.31 (br, 2 H), 3.45 (t, 2 H), 3.11 (s, 3 H), 1.92 (t, J=7.2 Hz, 2 H), 1.44-1.47 (m, 4 H), 1.22-1.26 (m, 4 H), MS m/z 499.9 [M+H]⁺.

Example 21

Preparation of Compound 21

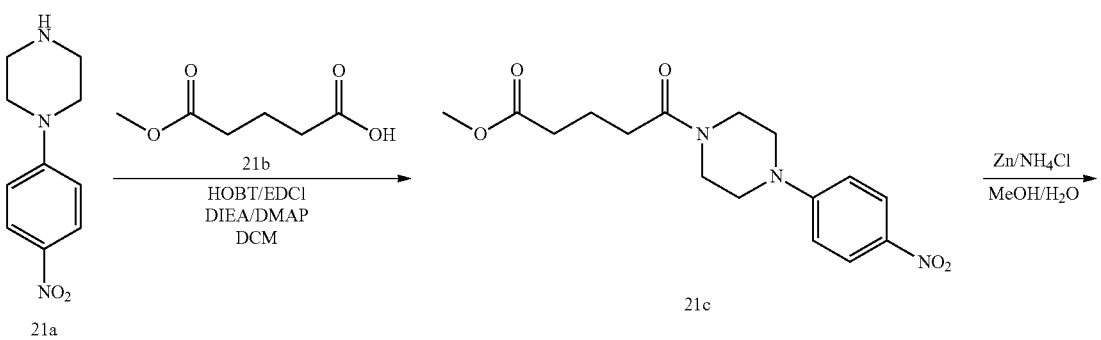

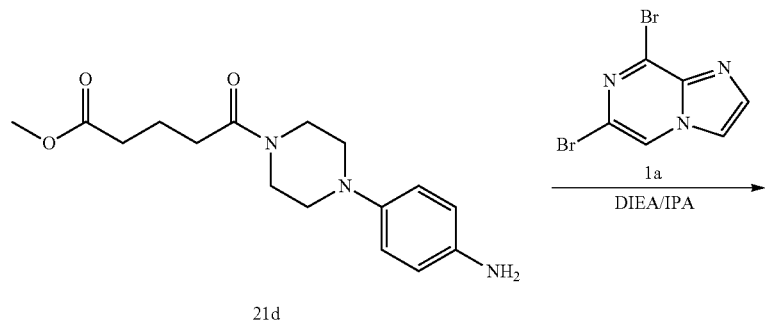

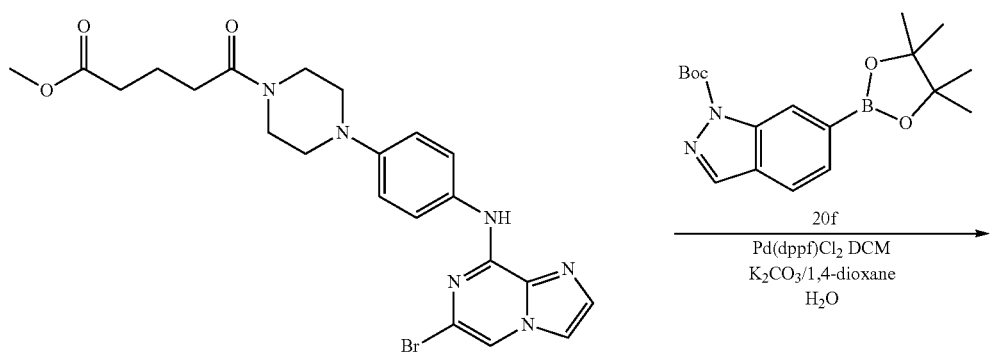

-continued
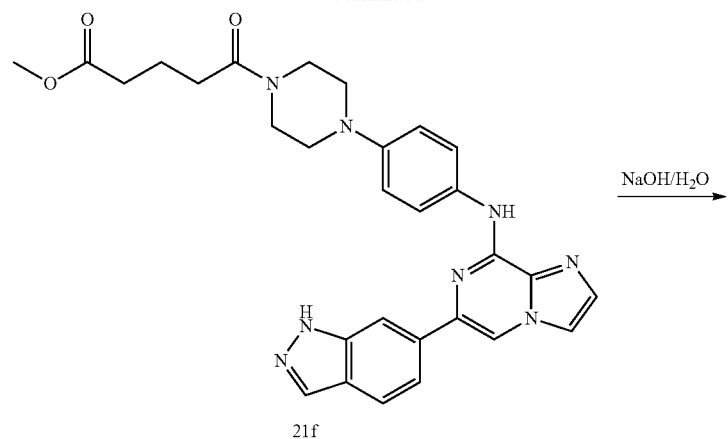
21f
NaOH/H₂O →
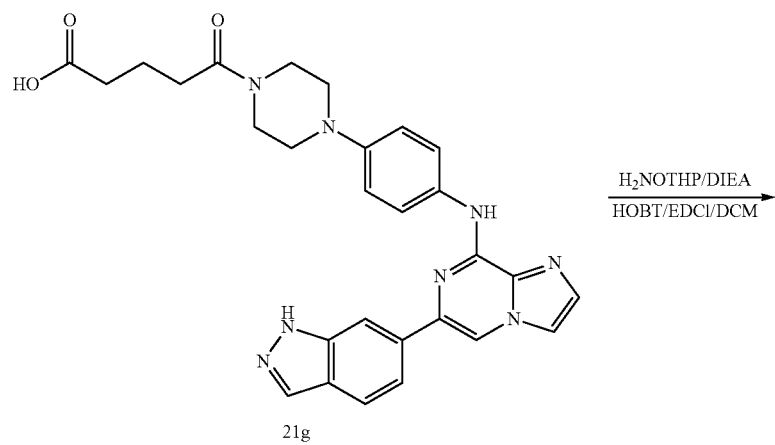
21g
H₂NOTHP/DIEA
HOBT/EDCl/DCM →
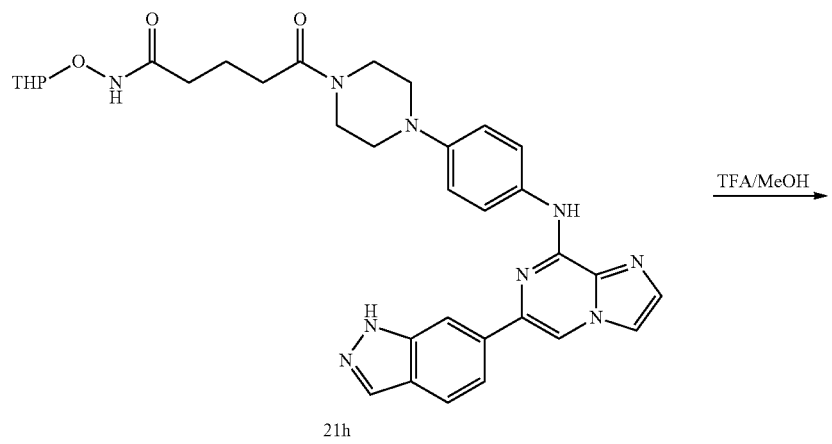
21h
TFA/MeOH →

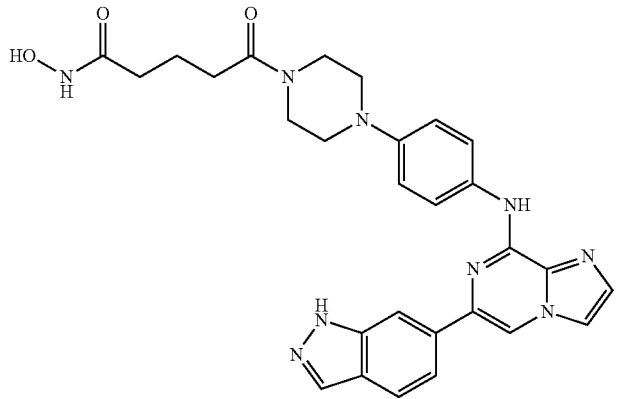

21

21b (1.4 g, 9.6 mmol) was dissolved in dichloromethane (20.5 mL), and 1-hydroxybenzotriazole (1.4 g, 10.6 mmol), EDCI (2.4 g, 12.5 mmol), 4-dimethylaminopyridine (118 mg, 0.9 mmol), N,N-diisopropylethylamine (3.7 g, 28.9 mmol) were successively added to the system. The reaction mixture was stirred at room temperature for half an hour and then 21a (2.0 g, 9.6 mmol) was added, and the mixture was stirred at room temperature overnight. The reaction mixture was washed with water (10.5 ml). After concentrated under reduced pressure, the organic phase was purified by silica gel column chromatography (n-hexane/ethyl acetate=10/1 mixed solvent elution) to give a bright yellow solid Compound 21c (1.7 g, yield 52.6%).

21c (1.7 g, 5.1 mmol) was placed in a 100 ml three-necked flask, and methanol (17.5 ml), ammonium chloride (2.7 g, 50.7 mmol), zinc powder (1.6 g, 25.4 mmol), water (6.2 ml) were sequentially added into the reaction flask. The reaction system was replaced with nitrogen for three times, heated to 60° C., and stirred for 4.5 hours. The reaction liquid was suction filtered to remove solid impurities, and the reaction liquid was concentrated to remove methanol to give crude product 21d (1.6 g).

21d (1.6 g, 5.2 mmol), 1a (1.4 g, 5.2 mmol), N,N-diisopropylethylamine (2.0 g, 15.7 mmol), isopropanol (16.2 mL) were added successively to 50 mL three-necked flask. The reaction system was replaced with nitrogen for three times, warmed to 90° C., and stirred to react for 5 hours. The reaction mixture was concentrated and purified by silica gel column chromatography (hexane/ethyl acetate=20/1) to give a crude product 21e (1.6 g, 60.5% yield).

21e (0.5 g, 1.0 mmol), 20f (1.0 g, 3.0 mmol), Pd(dppf)Cl$_2$·DCM (82 mg, 0.1 mmol), potassium carbonate (276 mg, 2.0 mmol), water (1.1 ml) and 1,4-dioxane (5.2 ml) were successively added to sealed pot, and was blown with nitrogen. After sealing, the reaction system was heated to 110° C. and stirred to react for 6 hours. The reaction solution was suction filtered, and the crude product was purified by silica gel column chromatography (hexane/ethyl acetate=3/1) to afford compound 21f (450 mg, purity 90.9%, yield 83.6%).

21f (0.4 g, 0.8 mmol) was suspended in water (4.5 ml), and sodium hydroxide (0.1 g, 2.5 mmol) was added. The mixture was warmed to 100° C., and the reaction was stirred for 1 hour. After cooled to room temperature, the pH of reaction mixture was adjusted to about 2 to 3 with 37% hydrochloric acid, and the reaction mixture was concentrated to dry to afford crude product 21g (0.6 g, purity 83.8%).

21g (0.6 g, 0.8 mmol) was dissolved in dichloromethane (60.5 mL) and N,N-dimethylacetamide (0.3 g, 2.5 mmol), 1-hydroxybenzene triazole (124 mg, 0.9 mmol EDCI (208 mg, 1.1 mmol) were added dropwise successively under stirring. The mixture was stirred to react at room temperature for 0.5 h, then H$_2$N-OTHP (108 mg, 0.9 mmol) was added and the mixture was stirred at room temperature overnight. Water (30.5 ml) was added to the reaction mixture, and extracted with dichloromethane (20.5 ml). The organic phase was concentrated and purified by silica gel column chromatographe to give yellow-green solid 21h (160 mg, 81.0% purity, 30.6% yield).

21h (160 mg, 0.2 mmol) was dissolved in methanol (3.1 mL), trifluoroacetic acid (185 mg, 1,3 mmol) was added under stirring, and reacted at room temperature for 3.5 hours and then at 40° C. for 4.5 hours, then heated to 60° C. to react for 15 minutes. After the reaction mixture was cooled to room temperature, 70 mg of filter cake was obtained. The filter cake was dissolved in N,N-dimethylformamide (1.1 ml), and purified by preparative liquid phase reverse-phase column chromatography to obtain compound 21 (20 mg, purity 97.8%, yield 14.5%). $^1$H NMR (400 MHz, DMSO-d$_6$) δ 10.35 (br, 1 H), 9.61 (br, 1 H), 8.71 (s, 1 H), 8.18 (s, 1 H),8.09 (d, J=0.9 Hz ,1 H), 8.02-8.04 (m, 3 H), 7.83-7.86 (d, J=8.5, 1 H), 7.73 (d, J=0.9 Hz, 1 H), 7.71(d, J=1.4 Hz, 1 H), 7.09 (d, J=9.1 Hz, 2 H), 3.63 (4 H), 3.13 (4 H), 2.36 (t, J=7.4 Hz, 2 H), 2.01(t/=7.4 1 Hz, 2 H), 1.75(m, 2 H).

Example 22
Preparation of Compound 22
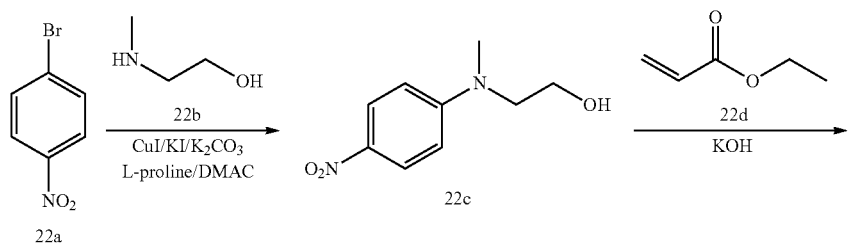
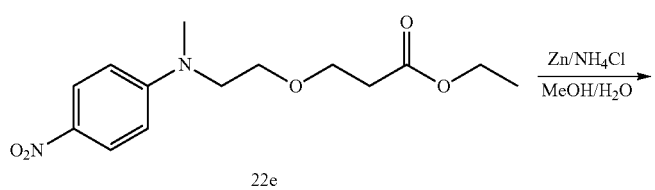
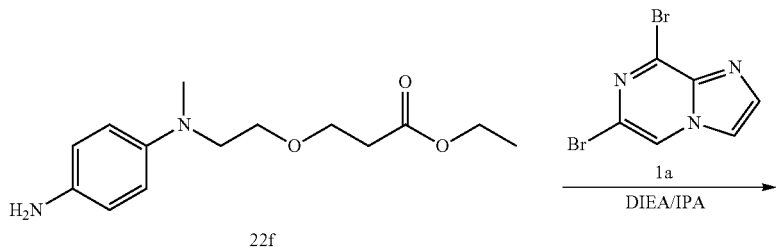
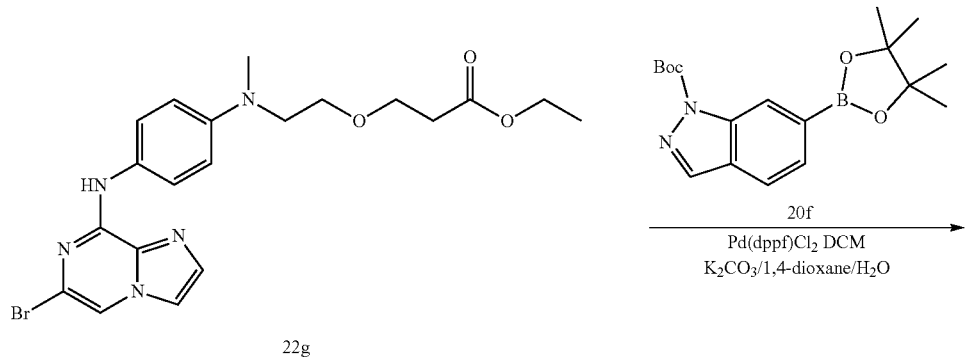
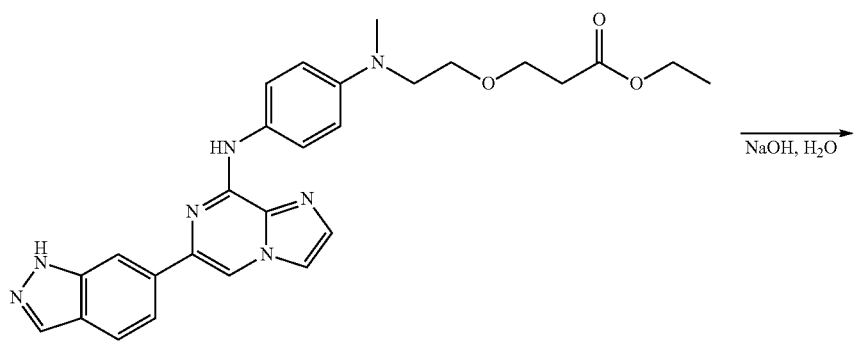

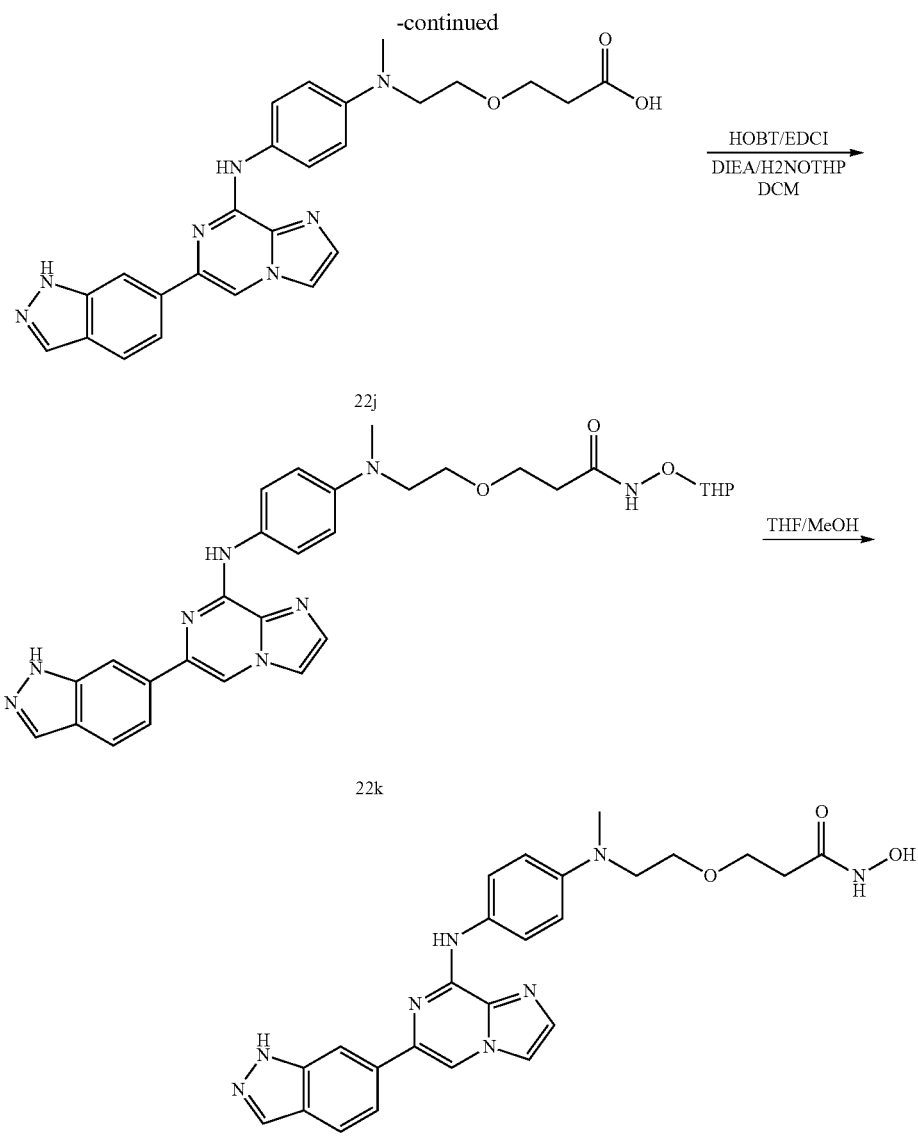

22a (4.0 g, 19.8 mmol) was dissolved in N,N-dimethylacetamide (30.5 mL), then 22b (2.2 g, 29.7 mmol), potassium carbonate (8.2 g, 59.4 mmol), potassium iodide (329 mg, 1.9 mmol), cuprous iodide (377 mg, 1.9 mmol), and L-valine (228 mg, 1.9 mmol) were added successively. The reaction system was replaced with nitrogen for three times, and heated to 120° C. and stirred overnight. Water (160 ml) was added to the reaction mixture and extracted with ethyl acetate (80 ml×3), the extracted organic phase was concentrated, and separated by silica gel column chromatography (hexane/ethyl acetate=10/1) to give 22c (2.9 g, purity 99.9%, yield 76.4%).

22c (500 mg, 2.5 mmol) and 22d (5.0 ml) were added to a tank reactor, and potassium hydroxide (50 mg, 0.7 mmol) was added. The reaction system was blown with nitrogen, and heated to 120° C. and stirred overnight. The reaction solution was concentrated to remove the remaining 22d, and purified by preparative thin-layer chromatography (developing solvent: n-hexane/ethyl acetate=2/1, UV=254 nm, $R_f$=0.6) to provide 22e (400 mg, purity 73.1%, yield 52.9%).

22e (400 mg, 1.3 mmol), zinc powder (441 mg, 6.7 mmol), ammonium chloride (722 mg, 13.5 mmol), methanol (4.1 ml) and water (1.1) were added to a 25 ml three-necked flask.

The reaction system was replaced with nitrogen for three times, then heated to 40° C. to react for 3 hours, and warmed to 50° C. to react for 40 minutes, then warmed to 60° C. to react for 2.5 hours. The reaction solution was suction filtered, and the filtered cake was concentrated to remove methanol and water. Water (30.5 ml) was added and extracted with ethyl acetate (30 ml×3), and the combined organic phases were concentrated under reduced pressure to provide crude product 22f (320 mg, yield 89.0%).

22f (320 mg, 0.9 mmol), 1a (266 mg, 0.9 mmol), N,N-diisopropylethylamine (373 mg, 2.8 mmol), and isopropanol (3.1 mL) were added successively to 50mL three-necked flask. The reaction system was replaced with nitrogen for three times, warmed to 90° C., and stirred to react for 5 hours. The reaction solution was concentrated and purified by preparative thin-layer chromatography (developing solvent: n-hexane/ethyl acetate=1/1, UV=254 nm, $R_f$=0.4) to provide compound 22e (250 mg, purity 97.6%, yield 56.4%).

22g (50 mg, 0.1 mmol), 20f (112 mg, 0.3 mmol), Pd(dppf)Cl$_2$·DCM (9 mg, 0.01 mmol), potassium carbonate (30 mg, 0.2 mmol), water (0.4 ml) and 1,4-dioxane (2.1 ml) were successively added to sealed pot, and was blown with nitrogen. After sealing, the reaction system was heated to 110° C. and stirred to react for 6 hours. The reaction solution was suction filtered, and the crude product obtained by concentrating the filtrate was purified by preparative thin-layer chromatography (developing solvent=dichloromethane/methanol=20/1, UV=254 nm, $R_f$=0.4, $R_f$=0.1) to provide 22i (24 mg, purity 90.9%).

22i (24 mg, 0.05 mmol) was dissolved in dichloromethane (5.1 mL), and N,N-dimethylacetamide (13 mg, 0.1 mmol), 1-hydroxybenzene triazole (8 mg, 0.05 mmol), EDCI (13 mg, 0.06 mmol) were added dropwise successively under stirring. The mixture was stirred to react at room temperature for 0.5 h, then H$_2$N-OTHP (7 mg, 0.06 mmol) was added and the mixture was stirred at room temperature overnight. Water (10 ml) and dichloromethane (10 ml) were added to the reaction mixture, and the organic phase was concentrated and purified by preparative thin-layer chromatography (developing solvent: n-hexane/ethyl acetate=1/1, UV=254 nm, $R_f$=0.4) to provide product 22j (14 mg, purity 97.9%, yield 48.2%).

22j (14 mg, 0.02 mmol) was dissolved in methanol (3.1 mL), and trifluoroacetic acid (14 mg, 0.1 mmol) was added under stirring, and stirred at room temperature overnight, then warmed to 40° C. to react for 5.5 hours. The reaction solution was filtered, and the filter cake was dried overnight at 30° C. in a vacuum oven to give pale yellow 22 (1.9 mg, purity 95.4%, yield 14.5%). MS m/z 487.1 [M+H]$^+$.

Example 23

Preparation of Compound 23

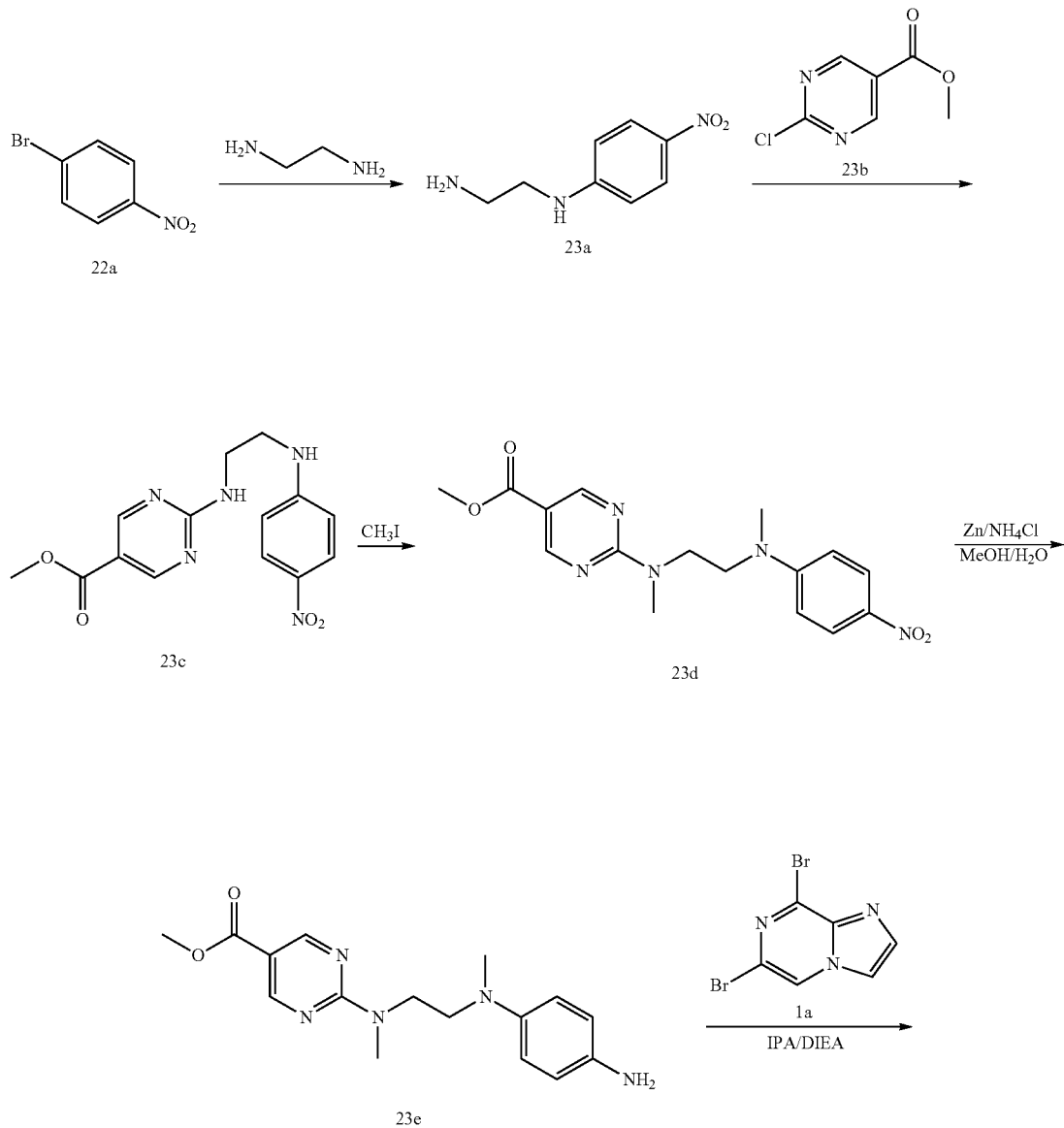

-continued
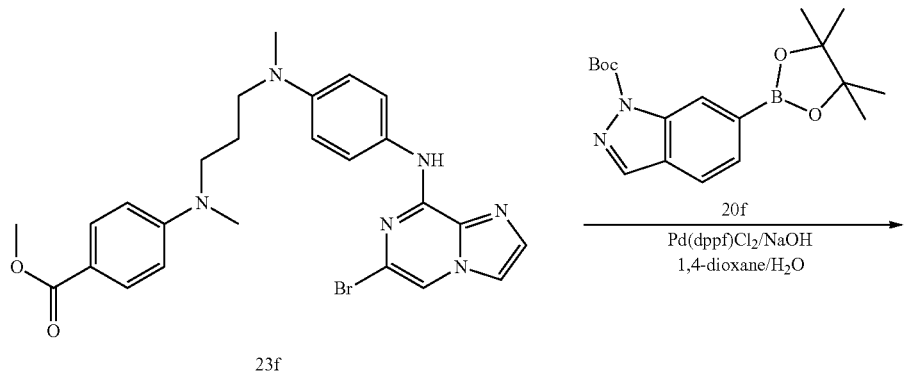
23f
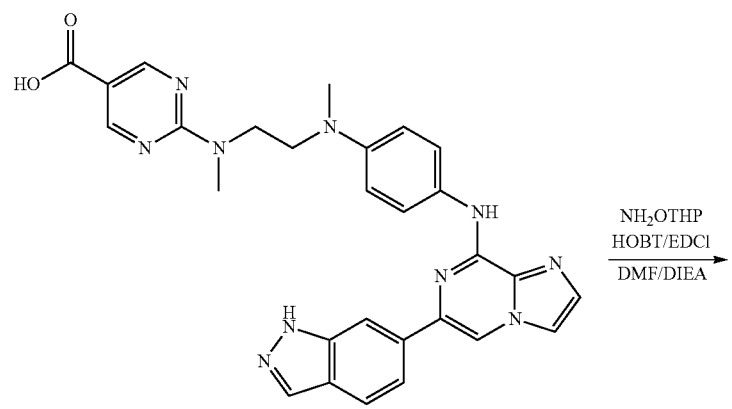
23g
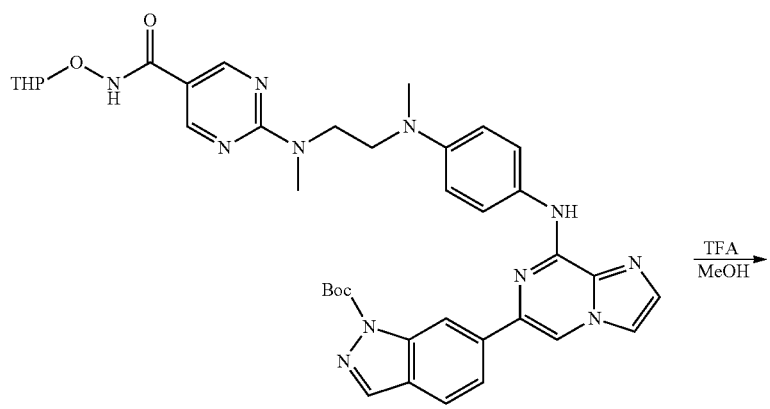
23h

-continued

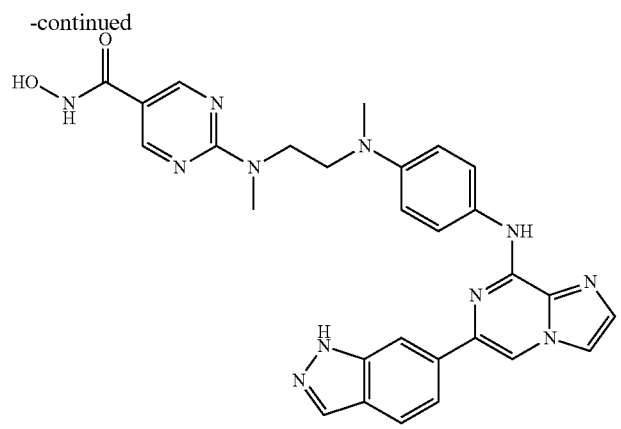

23

22a (5.1 g, 31.7 mmol) and ethylenediamine (20.1 ml) were added to a reaction flask, and the air in the system was replaced with $N_2$ gas for three times, and then (the mixture) heated to 120° C. to react for 2 hours. The raw material was detected to been consumed by thin layer chromatography (ethyl acetate/n-hexane=1/3). The reaction was cooled to room temperature and concentrated under reduced pressure. Water (25 mL) was then added and pulped at 100° C. for 1 hour. After filtration, the filter cake was transferred to a watch glass and placed in a forced air oven at 60° C. for drying. After drying, a bright yellow solid 23a (5.5 g, yield 95.7%) was obtained.

23a (3.6 g, 26,1 mmol), 23b (3.4 g, 26.0 mmol), and triethylamine (4.0 g, 52.1 mmol) were dissolved in methanol (50.5 ml) and reacted at room temperature for 16 hours. The reaction was monitored by thin layer chromatography (methanol/dichloromethane=1/5) until the starting material point ($R_f$=0.6) disappeared and a new spot was formed ($R_f$=0.8). The reaction mixture was concentrated under reduced pressure to give a bright yellow solid compound 23c (4.6 g, purity 86.2%, yield 55.6%).

23c (4.6 g, 14.5 mmol) was dissolved in N,N-dimethylformamide (50 mL) to reduce the system temperature to below 0° C. Sodium hydride (1.7 g, 43.5 mmol) was slowly added portionwise, during which the temperature was kept below 0° C., and then stirred for 1 hour to react after the addition. Methyl iodide (12.5 g, 87.0 mmol) was added slowly, and the reaction was carried out at 0° C. for 2 hours. The raw material was detected to been consumed by thin layer chromatography (ethyl acetate/n-hexane=1/1). Water (50.1 ml) was added to the reaction mixture, and extracted with ethyl acetate (50 mL×3). The combined organic phase was dried, filtered, and concentrated under reduced pressure. The crude product was purified by silica gel column chromatography (hexane:ethyl acetate=8:1 solvent mixture elution) to give yellow solid compound 23d (1.9 g, purity 88.5%, yield 41.5%). MS m/z 346.3 [M+H]$^+$.

23d (1.9 g, 5.5 mmol), ammonium chloride (2.9 g, 55.0 mmol), zinc powder (1.8 g, 27.5 mmol), and water (4.1 ml) were dissolved in methanol (19.2 ml). The reaction system was replaced with nitrogen for three times and heated to 50 to react for 4 hours. The reaction mixture was filtered after thin layer chromatography (ethyl acetate/n-hexane=1/1) monitor showed that the starting material was consumed. The filtrate was washed with methanol (20.2 ml), and the organic filtrate was combined and concentrated to dryness to give solid compound 23e (810 mg, yield 46.6%).

23e (810 mg, 2.5 mmol), 1a (712 mg, 2.5 mmol), N,N-diisopropylethylamine (996 mg, 7.7 mmol) were dissolved in isopropyl alcohol (8.1 mL). The reaction system was replaced with nitrogen for three times, and warmed to 90° C. and stirred to react overnight. The raw material was detected to been consumed by thin layer chromatography (ethyl acetate/n-hexane=1/1). The reaction was concentrated under reduced pressure, the obtained crude product was purified by silica gel column chromatography (hexane/ethyl acetate=5/1 mixed solvent elution) to provide yellow solid compound 23f (908 mg, purity 96.0%, yield 69.1%).

23f (300 mg, 0.6 mmol), C62-9 (606 mg, 1.7 mmol), sodium hydroxide (188 mg, 4.7 mmol), Pd(dppf)Cl$_2$·DCM (144 mg, 0.2 mmol) were dissolved in 1,4-dioxane (3.2 ml). The reaction system was replaced with nitrogen for three times, and the mixture was warmed to 110° C. and stirred to react overnight. The reactant was cooled to room temperature, and dilute hydrochloric acid was added to the reaction mixture to adjust the pH to 4 to 5. The reaction mixture became cloudy and yellow solid was formed. Ethyl acetate (10 ml) was added to the mixture and stirred for 0.5 hr. Filtered to give a crude yellow solid, and purified by preparative thin layer chromatography to provide yellow solid 23g (270 mg, yield 86.1%). MS m/z 535.6 [M+H]$^+$.

23g (150 mg, 0.3 mmol), 1-hydroxybenzotriazole (42 mg, 0.3 mmol), carbodiimide hydrochloride (70 mg, 0.4 mmol), N,N-diisopropyl ethylamine (73 mg, 0.5 mmol) were dissolved in N,N-dimethylformamide (1.5 ml), stirred at room temperature for 30 min, and NH$_2$ OTHP (45.7 mg, 0.4 mmol) was added and stirred to react overnight. The reaction was cooled to room temperature, and the crude product was purified by preparative thin-layer chromatography to provide green solid compound 23h (62 mg, 88.6% purity, 41.4% yield), MS m/z 634.7 [M-Boc-+H]$^+$.

23h (62 mg, 0.1 mmol) was dissolved in methanol (15.2 ml), trifluoroacetic acid (177 mg, 1.5 mmol) was added, and the system was warmed to 60° C. to react for 4 hours. The insolubles appeared in the reaction mixture was the product. Thin layer chromatography (dichloromethane:methanol=1: 10) monitored that the starting material was consumed. After filtration, the filter cake was dried in a vacuum oven at 40° C. to obtain bright yellow solid 23 (20 mg, purity 95.4%, yield 35.5%). $^1$H NMR (400 MHz, DMSO-d$_6$) δ 13.19 (s, 1

H), 11.06 (s, 1 H), 9.45 (s, 1 H), 8.68 (d, J=14.9 He, 3H), 8.16 (s, 1 H), 8.10 (s, 1 H), 8.01 (s, 1 H), 7.95 (d, J=8.5 Hz, 2 H), 7.85 (d, J=8.5 Hz, 1 H), 7.75-7.68 (m, 2 H), 6.88 (d, J=8.1 Hz, 2 H), 3.82 (t, J=6.7 Hz, 2 H), 3.60 (t, J=6.7 Hz, 2 H), 2.97 (s, 3 H). MS m/z 550.5 [M+H]$^+$.

Example 24

1. Syk Kinase Activity Inhibitiory Experiment

Measure of SYK protein kinase activity was carried out by using the Caliper mobility shift assay. The compound was dissolved with DMSO and diluted with kinase buffer (20 mM HEPES pH 7.5, 0.01% Triton X-100, 5 mM MgCl$_2$, 1 mM MnCl$_2$, 2 mM DTT), and 5 μl of 5 times the final concentration of the compounds (10% DMSO) were added to 384 well plate. 10 μl of 2.5 fold enzyme (with SYK) solution was added and incubated at room temperature for 10 minutes, then 10 of 2.5 fold substrate (Peptide FAM-P22) and ATP) solution was added. The mixture was incubated for 30 minutes under 28° C., and 25 μl of stop buffer (100 mM HEPES pH 7.5, 0.015% Brij-35, 0.2% Coating Reagent #3, 50 mM EDTA) was added to terminate the reaction. Conversion rate data was read by Caliper EZ Reader II (Caliper Life Sciences). Conversion rate was converted to inhibition rate data (% inhibition rate=(max−conversion rate)/(max−min)*100). The max refers to the conversion rate of the DMSO control, and min refers to the conversion rate of the enzyme-free control. The curve was drawn with the compound concentration and inhibition rate as the horizontal and vertical coordinates, and the curve was fitted with the XLFit excel add-in version 4.3.1 Software, and IC$_{50}$ was calculated.

The results indicate that the IC$_{50}$ of majority of the tested compounds of the present invention was 10-1000 nM, and the IC$_{50}$ of preferred compound was lower than 20 nM. The activities of some representative compounds are shown in Table 1.

TABLE 1

Inhibition of Syk kinase activity

| Compound | Syk (IC$_{50}$, nM) |
|---|---|
| 1R | <10 |
| 2R | <10 |
| 3R | <500 |
| 4R | <10 |
| 5R | <10 |
| 6 | <10 |
| 7 | <10 |
| 8R | <10 |
| 9R | <100 |
| 11 | <500 |
| 12 | <100 |
| 13 | <100 |
| 14 | <500 |
| 17 | <1000 |
| 18 | <500 |
| 19 | <1000 |
| 20 | <50 |
| 21 | <10 |
| 22 | <50 |
| 23 | <50 |

2. HDAC-1 and HDAC-6 Activity Inhibition Experiment

HDAC activity was measured by the Synergy MX Multi-Function Microplate Reader. The compounds were dissolved with DMSO, and transferred to a 384 well test plate using an Echo non-contact nanoscale sonic pipetting system. 15 μl of enzyme (HDAC1/HDAC6, respectively) solvent was added, and incubated at room temperature for 15 minutes, then 10 μl of substrate (trypsin and Ac-peptide) solution was added. Fluorescence intensity signal was read directly on Synergy MX (fluorescence excitation 355 nm, emission fluorescence 460 nm) after cultivated at room temperature for 60 minutes. Fluorescence intensity signal was convented into inhibition rate data (% inhibition rate= (max−fluorescence intensity)/(max−min)*100). The max refers to the fluorescence intensity of the DMSO control, and min refers to the fluorescence intensity of the enzyme-free control. The curve was drawn with the compound concentration and inhibition rate as the horizontal and vertical coordinates, and the curve was fitted with the GraphPad Prism V5.0 Software, and IC$_{50}$ was calculated.

TABLE 2

HDAC activity inhibition

| Compound | HDAC1 (IC$_{50}$, nM) | HDAC6 (IC$_{50}$, nM) |
|---|---|---|
| 6 | <1000 | <50 |
| 7 | <30 | <30 |
| 10 | <2000 | |
| 12 | <200 | |
| 13 | <200 | |
| 14 | <20 | |
| 17 | <50 | |
| 18 | <100 | |
| 19 | <500 | |
| 20 | <20 | |
| 21 | <100 | |
| 22 | <500 | |
| 23 | <30 | |

All literatures mentioned in the present application are incorporated herein by reference, as though each one is individually incorporated by reference. Additionally, it should be understood that after reading the above content, those skilled in the art can make various changes and modifications to the present invention. These equivalents also fall within the scope defined by the appended claims.

The invention claimed is:

1. A compound of formula (I), or the optical isomers, or pharmaceutically acceptable salts thereof:

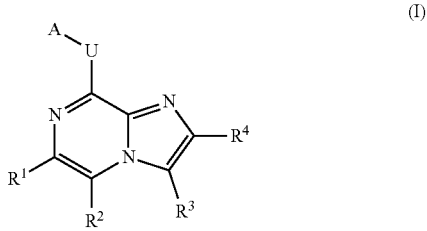

(I)

wherein in the formula (I),
R$^1$ is aryl, heteroaryl or 6-membered monocyclic heterocyclyl (including saturated and unsaturated); aryl, heteroaryl or monocyclic heterocyclyl herein may be optionally and independently substituted by 1-3 substituents each independently selected from the group consisting of: halogen, C$_{1-4}$ alkyl, C$_{1-4}$ halogenated alkyl, C$_{2-4}$ alkenyl, C$_{2-4}$ alkynyl, C$_{3-8}$ cycloalkyl, 3- to 8- membered heterocyclyl, aryl, heteroaryl, CN, NO$_2$, OR$^8$, SR$^8$, NR$^8$R$^9$, C(O)R$^8$, C(O)OR$^8$, C(O)NR$^8$R$^9$, S(O)$_2$R$^8$ and R$^7$.

R$^2$, R$^3$ and R$^4$ are hydrogen;
U is selected from NR$^5$; where R$^5$ is hydrogen;

A is selected from the group consisting of formula (II):

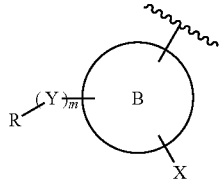
(II)

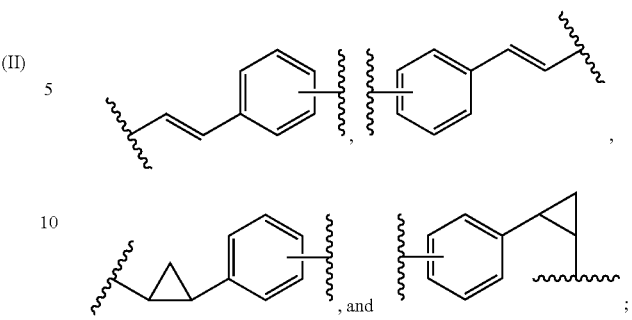
, and
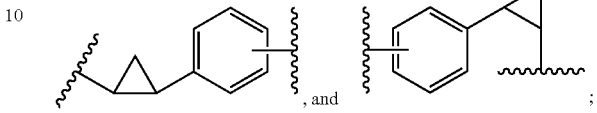
;

wherein:

" $\sim\!\sim\!\sim$ " refers to the connection point of formula (II) to U of the formula (I);

B is a monocyclic aryl or bicyclic aryl group, or a monocyclic heteroaryl or bicyclic heteroaryl group, and at least one of the bicyclic aryl or bicyclic heteroaryl is aromatic, and the other ring is aromatic, saturated or partially saturated ring;

Y is 3- to12-membered monocyclic or polycyclic heterocyclic ring; wherein said heterocyclic ring contains 1-4 heteroatoms each independently selected from N, O and S;

m is 0 or 1;

each X is independently hydrogen, halogen, $C_{1-4}$ alkyl, $C_{3-6}$ cycloalkyl, 3- to 6- membered heterocyclyl, CN, $OR^8$, $SR^8$, $NR^8R^9$, $C(O)R^8$, $C(O)OR^8$, $C(O)NR^8R^9$, or $S(O)_2R^8$;

R is hydrogen, $-(CH_2)_p-V-(CH_2)_qC(O)NH(OH)$, $-V^1-(CH_2)_p-V^2-V-(CH_2)_qC(O)NH(OH)$;

$R^7$ is hydrogen, $-(CH_2)_p-V-(CH_2)_qC(O)NH(OH)$, $-V^1-(CH_2)_p-V^2-V-(CH_2)_qC(O)NH(OH)$, $C(O)NH(OCH_3)$,

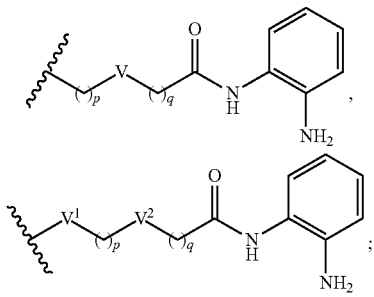

$R^8$ and $R^9$ are each independently hydrogen, $C_{1-4}$ alkyl, $C_{1-4}$ halogenated alkyl, $C_{2-4}$ alkenyl, $C_{2-4}$ alkynyl, $C_{3-8}$ cycloalkyl, 3- to 8-membered heterocyclyl, aryl, or heteroaryl; or $R^8$ and $R^9$ together with the nitrogen atom to which they are attached form a 3- to 9-metacyclic ring comprising 1-2 N atom and 0, 1 or 2 heteroatoms selected from O or S;

V is a divalent group, each of p and q is independently an integer from 0 to 10, and the V is selected from the group consisting of bond, O, S, $NR^{11}$, OC(O), OC(O)O, NHC(O), NHC(O)NH, NHC(O)O, OC(O)NH, NHS$(O)_2$, C(O), C(O)O, C(O)NH, S(O), S(O)$_2$, S(O)$_2$NH, or NHS(O)$_2$NH, CH=CH, C≡C, $CR^{12}R^{13}$, $C_{3-8}$ cycloalkyl, 3- to 12-member heterocyclyl, aryl or heteroaryl, with the prerequisite that V, p and q together form a chemically stable group;

$V^1$ and $V^2$ are divalent groups selected from the group consisting of bond, O, S, $NR^{11}$, and C(O)NH, with the prerequisite that the group formed by V, $V^1$, $V^2$, p and q is chemically stable group;

$R^{11}$ is hydrogen, $C_{1-4}$ alkyl, $C_{3-8}$ cycloalkyl, 3- to 8-membered heterocyclyl, aryl, heteroaryl, $C(O)R^8$ or $S(O)_2R^8$;

$R^{12}$ and $R^{13}$ are each independently hydrogen, halogen, $C_{1-4}$ alkyl, $C_{3-6}$ cycloalkyl, $C_{2-4}$ alkenyl, $C_{2-4}$ alkynyl, 3- to 8-membered heterocyclic, $OR^8$, $SR^8$, $NR^8R^9$, CN, $C(O)R^8$, $C(O)OR^8$, $C(O)NR^8R^9$, $OC(O)R^8$, $NR^8C(O)R^9$, or $S(O)_2R^8$, or $R^{12}$ and $R^{13}$ together with the carbon atoms to which they are attached form 3-8 membered cyclic structure containing 0, 1 or 2 heteroatoms selected from N, O, or S;

with a proviso that when formula (II) is

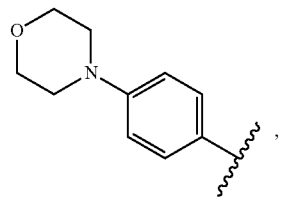 [SMILES: *c1ccc(N2CCOCC2)cc1 ; ","]

then $R^1$ is

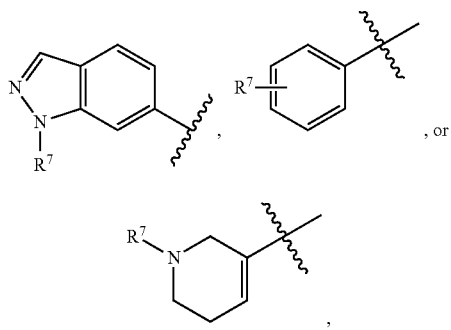

and $R^7$ is other than hydrogen, and the definitions of V, $V^1$, $V^2$, p and q in $R^7$ must ensure that the formed le group is a stable chemical structure;

with another proviso that when R¹ does not comprise structural unit

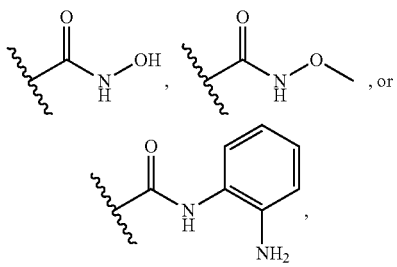

then A is of formula (IIa), wherein R comprises structural unit

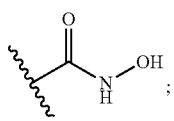

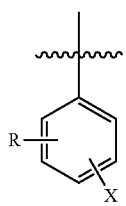
(IIa)

wherein each of the alkyl, alkenyl, alkynyl, cycloalkyl, heterocyclyl, aryl and heteroaryl is each optionally and independently substituted by 1-3 substituents each independently selected from the group consisting of halogen, $C_{1-4}$ alkyl, $C_{1-4}$ halogenated alkyl, $C_{2-4}$ alkenyl, $C_{2-4}$ alkynyl, $C_{3-8}$ cycloalkyl, 3- to 8- heterocyclyl, aryl, heteroaryl, CN, $NO_2$, $OR^8$, $SR^8$, $NR^8R^9$, C(O) $R^8$, $C(O)OR^8$, $C(O)NR^8R^9$ and $S(O)_2R^8$; and the above aryl group is an aryl group having 6 to 12 carbon atoms; and the heteroaryl group is a 5- to 15-membered heteroaryl group.

2. The compound of claim 1, wherein R¹ is

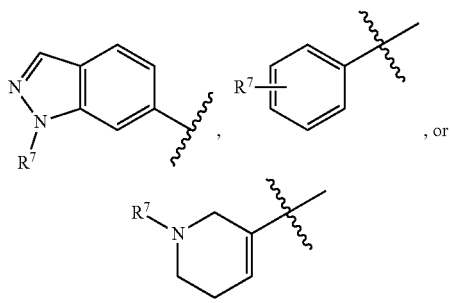

wherein R⁷ is as described in claim 1.

3. The compound of claim 1, or the optical isomers, pharmaceutically acceptable salts thereof, wherein B is phenyl; Y is 6- membered monocyclic heterocyclic ring having 1-2 heteroatoms each independently being N, O or S, or Y is absent.

4. The compound of claim 1, or the optical isomers, pharmaceutically acceptable salts thereof, wherein in the formula (II), is a structure selected from group consisting of:

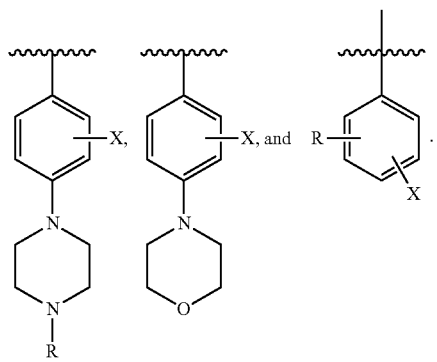

wherein X is hydrogen, halogen, $C_{1-4}$ alkyl, CN, or $OR^5$; R is as described in claim 1.

5. The compound of claim 1, or the optical isomers, pharmaceutically acceptable salts thereof, wherein R is —(CH₂)$_p$—V—(CH₂)$_q$C(O)NH(OH) or —V¹—(CH₂)$_p$—V²—V—(CH₂)$_q$C(O)NH(OH); wherein V is bond, O, NR¹¹, CH=CH, aryl, heteroaryl, OC(O), NHC(O), C(O), S(O)₂; each R¹¹ is independently hydrogen or $C_{1-4}$ alkyl; p is 0, 1, 2, 3, or 4; q is 0, 1, 2, 3, 4, 5, 6, 7, or 8; V¹ and V² are each independently selected from NR¹¹, O, S, or bond; with the proviso that the group formed by V, V¹, and V², p and q together is a stable chemical structure.

6. The compound of claim 5, wherein compound (I) is a structure selected from the group consisting of:

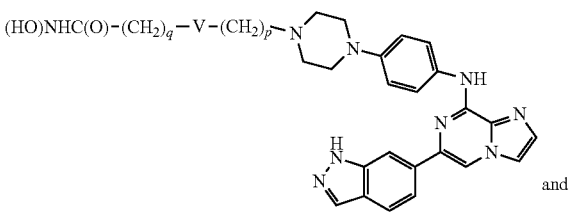

and

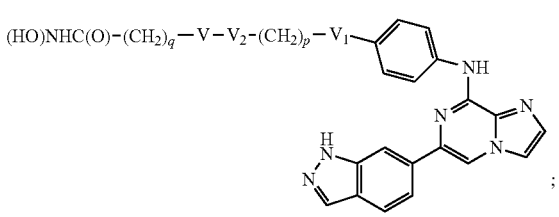

wherein V, V¹, V², p, and q are as defined in claim 5.

7. The compound of claim 1, or the optical isomers, pharmaceutically acceptable salts thereof, wherein the formula (I) is a structure selected from group consisting of:

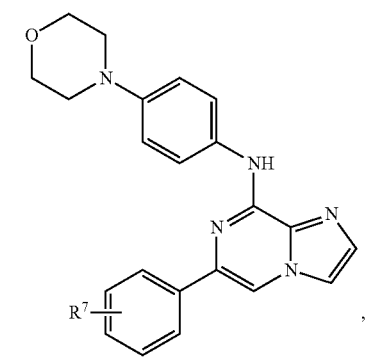

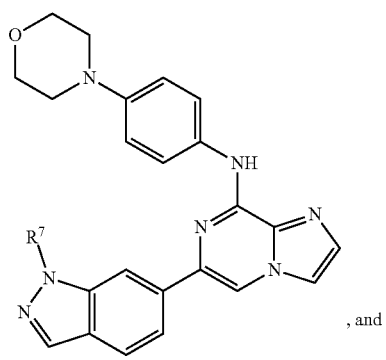
, and

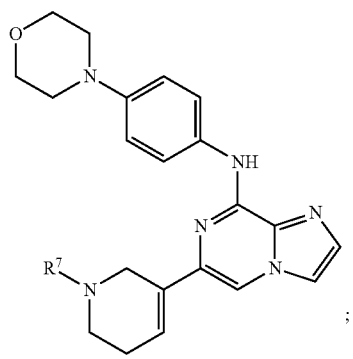
;

wherein R⁷ is —(CH₂)$_p$—V—(CH₂)$_q$C(O)NH(OH) or —V¹—(CH₂)$_p$—V²—V—(CH₂)$_q$C(O)NH(OH); wherein V is bond, O, NR¹¹, CH=CH, aryl, heteroaryl, OC(O), NHC(O), C(O), S(O)₂; each R¹¹ is independently hydrogen or C$_{1-4}$ alkyl; p is 0, 1, 2, 3, or 4; q is 0, 1, 2, 3, 4, 5, 6, 7, or 8; V¹ and V² are each independently selected from NR¹¹, O, S, or bond; with the proviso that the group formed by V, V¹, and V², p and q together is a stable chemical structure.

8. The compound according to claim 1, wherein the compound is selected from the group consisting of:

5

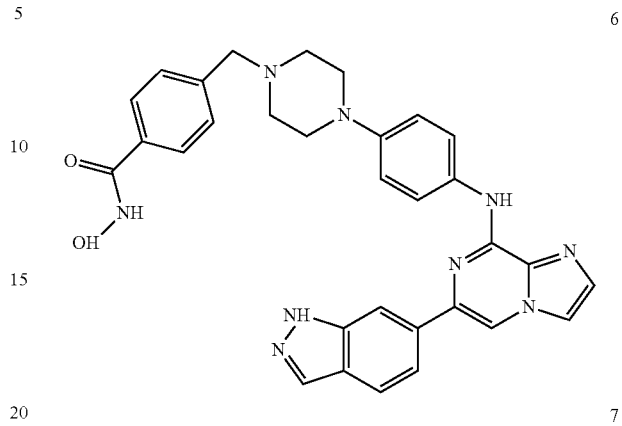

6

7

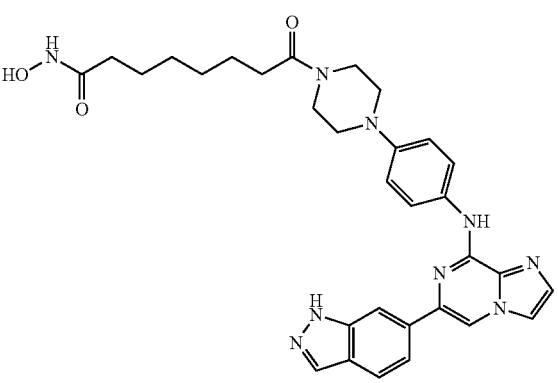

10

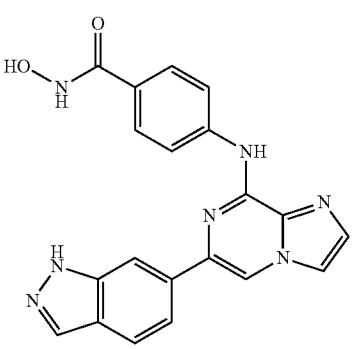

11

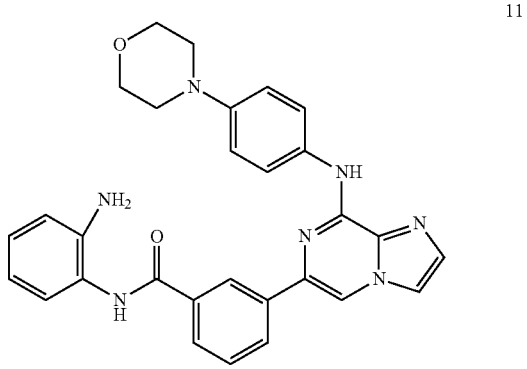

12
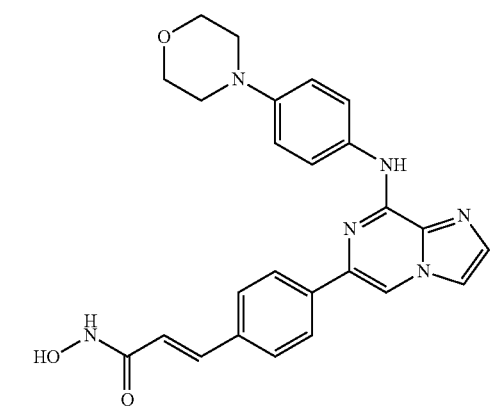
13
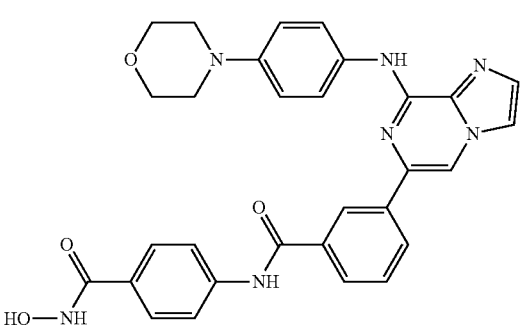
14
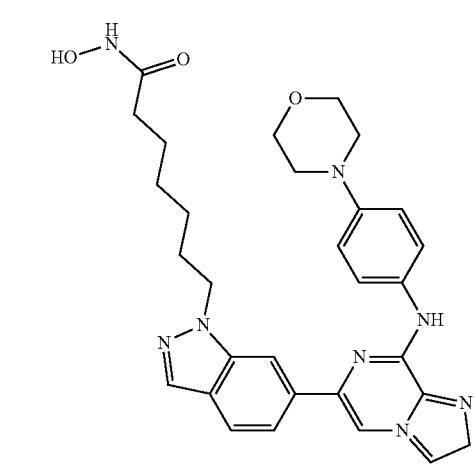
15
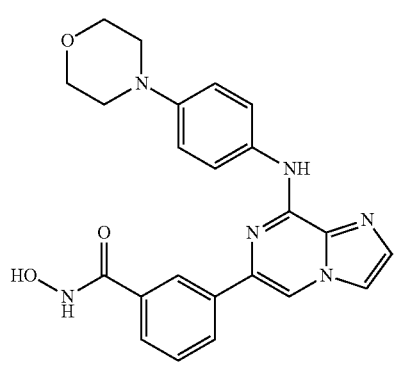
16
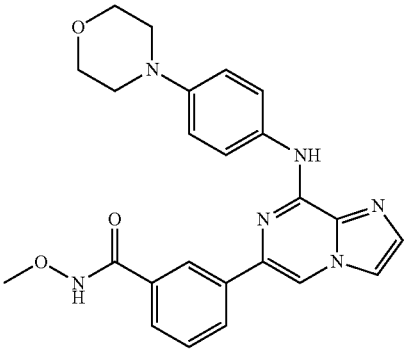
17
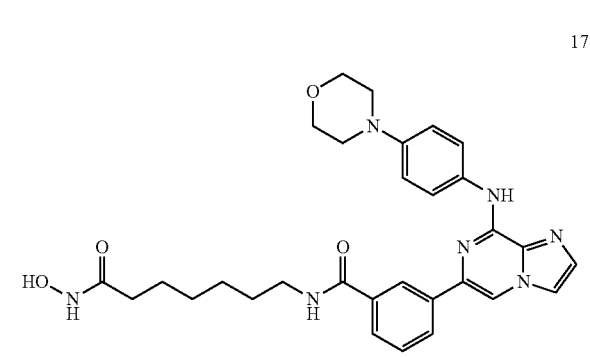
18
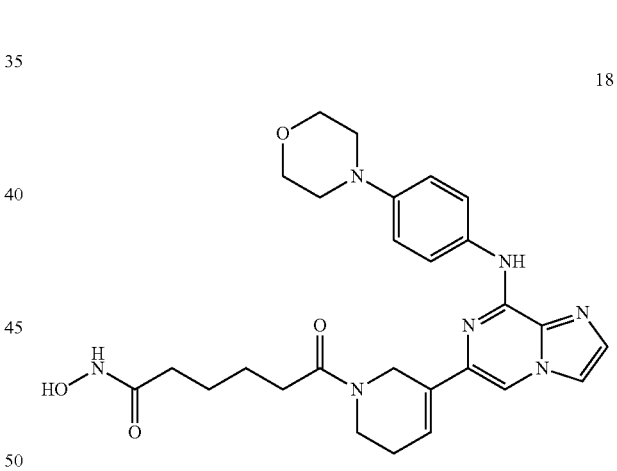
19
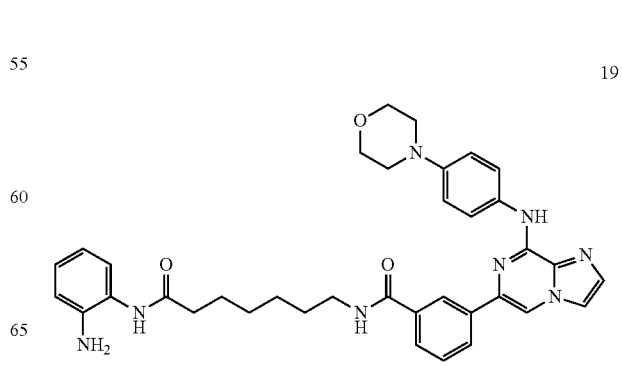

-continued

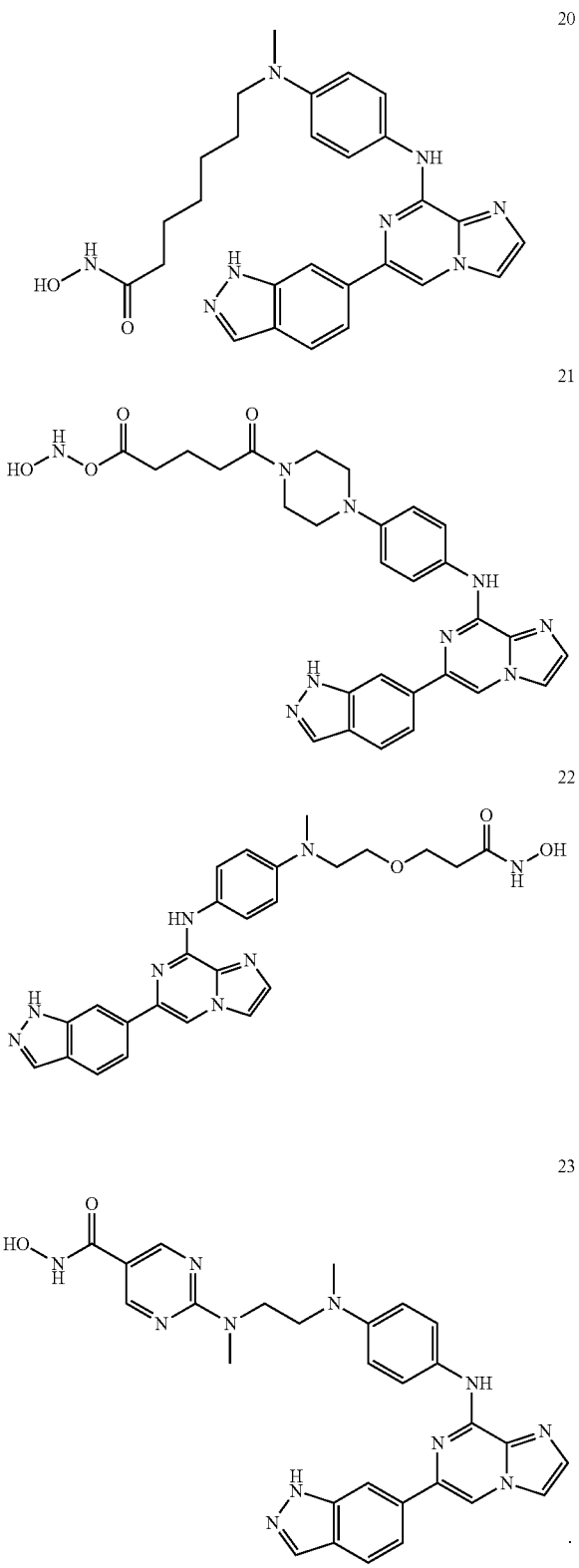

9. A pharmaceutical composition, comprising: (i) an effective amount of a compound of formula (I) according to claim 1, or the optical isomers, pharmaceutically acceptable salts thereof; and (ii) pharmaceutically acceptable carriers.

10. A method for the preparation of compound of claim 1 comprising the following steps:

(1) in an inert solvent, compound Ia reacts with A-NH$_2$ to provide compound Ib;

(2) in an inert solvent, compound Ib reacts with compound R$^1$B(OH)$_2$ to obtain compounds of formula I;

(3) the C(O)NH(OH) group in A or R$^1$ in the compound of formula (I) is prepared from the corresponding carboxylic ester, wherein carboxylic ester Ic or Id is hydrolyzed, and the resulting acid is further reacted with a tetrahydropyran protected hydroxylamine, and finally the tetrahydropyran protecting group is deprotected to give a hydroxyamide Ie or If, and the general schemes are as follows:

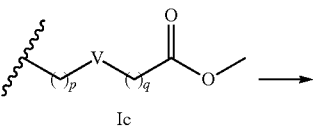

113
-continued
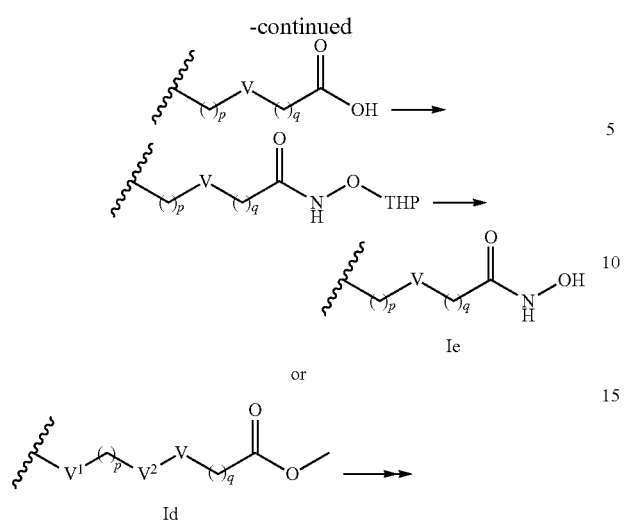
Ie
or
114
-continued
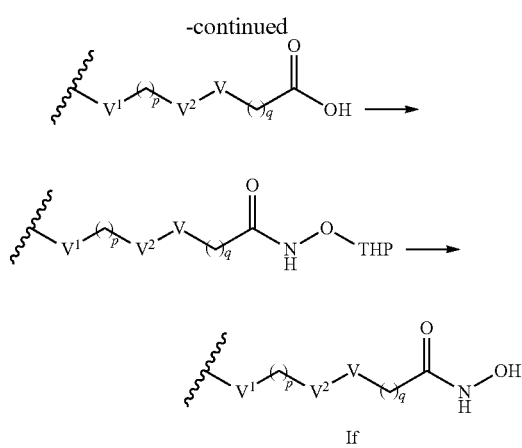
If
wherein each group is defined as in claim 1.
* * * * *